(12) United States Patent
Ly et al.

(10) Patent No.: US 7,960,393 B2
(45) Date of Patent: Jun. 14, 2011

(54) PYRIMIDINE DERIVATIVES USEFUL FOR THE TREATMENT OF DISEASES MEDIATED BY CRTH2

(75) Inventors: Tai-wei Ly, San Diego, CA (US); Yuji Koriyama, Kusatsu (JP); Takashi Yoshino, Saitama (JP); Hiroki Sato, Nara-ken (JP); Kazuho Tanaka, Tokushima (JP); Hiromi Sugimoto, Aichi (JP); Yoshihisa Manabe, Nara (JP); Kevin Bacon, San Diego, CA (US); Klaus Urbahns, Lund (SE); Masanori Seki, Kanagawa-ken (JP); Takuya Shintani, Kyoto (JP)

(73) Assignee: Actimis Pharmaceuticals, Inc., San Diego, CA (US)

( * ) Notice: Subject to any disclaimer, the term of this patent is extended or adjusted under 35 U.S.C. 154(b) by 0 days.

(21) Appl. No.: 12/868,663

(22) Filed: Aug. 25, 2010

(65) Prior Publication Data
US 2010/0322980 A1    Dec. 23, 2010

Related U.S. Application Data

(63) Continuation of application No. 10/554,668, filed as application No. PCT/EP2004/003910 on Apr. 14, 2002, now Pat. No. 7,812,160.

(30) Foreign Application Priority Data

Apr. 25, 2003 (EP) .................................. 03009384

(51) Int. Cl.
| A61K 31/505 | (2006.01) |
| A61K 31/506 | (2006.01) |
| A61P 11/06 | (2006.01) |
| C07D 239/34 | (2006.01) |
| C07D 239/42 | (2006.01) |
| C07D 239/48 | (2006.01) |
| C07D 401/12 | (2006.01) |
| C07D 403/12 | (2006.01) |
| C07D 403/14 | (2006.01) |
| C07D 405/12 | (2006.01) |
| C07D 407/12 | (2006.01) |

(52) U.S. Cl. ......... 514/256; 514/269; 544/324; 544/319
(58) Field of Classification Search .................. 544/324, 544/319; 514/269, 256
See application file for complete search history.

(56) References Cited

U.S. PATENT DOCUMENTS
| 7,812,160 B2 | 10/2010 | Ly et al. |
| 2007/0129355 A1 | 6/2007 | Ly et al. |

FOREIGN PATENT DOCUMENTS
| DE | 42 39 440 A | 6/1993 |
| EP | 1 170 594 A | 1/2002 |
| EP | 1 413 306 A | 4/2004 |
| EP | 1471057 | 10/2004 |
| GB | 1356834 | 6/1974 |
| GB | 2 262 096 A | 3/1992 |
| WO | WO 01/83485 | 11/2001 |
| WO | WO 03/066047 | 8/2003 |
| WO | WO 2004/058164 | 7/2004 |
| WO | WO 2004/096777 A1 | 11/2004 |
| WO | WO 2008/156780 | 12/2008 |
| WO | WO 2008/156781 | 12/2008 |

OTHER PUBLICATIONS

Pettipher R., British Journal of Pharmacology, 153, $191-$199, 2008.*
Hata et al., Pharmacology & Therapeutics 103, 147-166, 2004.*
International Search Report of International Application No. PCT/EP2004/003910 having a Publication No. WO 04/096777.
U.S. Appl. No. 12/665,705, filed Dec. 18, 2009, Tai Wei Ly.
U.S. Appl. No. 12/665,706, filed Dec. 18, 2009, Tai Wei Ly et al.

(Continued)

*Primary Examiner* — Venkataraman Balasubramanian
(74) *Attorney, Agent, or Firm* — Jones Day

(57) ABSTRACT

The present invention relates to a pyrimidine derivative of the formula (I) and salts thereof which is useful as an active ingredient of pharmaceutical preparations. The pyrimidine derivative of the present invention has excellent CRTH2 (G-protein-coupled chemoattractant receptor, expressed on Th2 cells) antagonistic activity and can be used for the prophylaxis and treatment of diseases associated with CRTH2 activity, in particular for the treatment of allergic diseases, such as asthma, allergic rhinitis, atopic dermatitis, and allergic conjunctivitis; eosinophil-related diseases, such as Churg-Strauss syndrome and sinusitis; basophil-related diseases, such as basophilic leukemia, chronic urticaria and basophilic leukocytosis in human and other mammals; and inflammatory diseases characterized by T lymphocytes and profuse leukocyte infiltrates such as psoriasis, eczema, inflammatory bowel disease, ulcerative colitis, Crohn's disease, COPD (chronic obstructive pulmonary disorder) and arthritis.

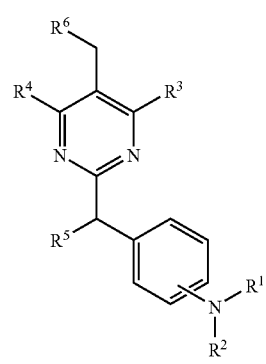

(I)

14 Claims, No Drawings

OTHER PUBLICATIONS

Sugimoto, H., et al, An Orally Bioavailable Small Molecule Antagonist of CRTH2, Ramatroban (Bay U3405), Inhibits Prostaglandin D2-Induced Eosinophil Migration In Vitro, *J. Pharmacology & Experimental Therapeutics*, Am. Soc. for Pharmacology and, U.S., vol. 305, No. 1, pp. 347-352 (2003).

Ulven, T., et al, Novel Selective Orally Active CRTH2 Antagonists for Allergic Inflammation Developed from In Silico Derived Hits, J. Med. Chem., 49, pp. 6638-6641 (2006).

Ordukhanyan, A. A., et al, Khimiko-Farmatsevticheskii Zhurnal, 13(9): 36-40 (1979) (English abstract provided).

Ly, T. W., et al, Small-Molecule CRTH2 Antagonists for the Treatment of Allergic Inflammation: An Overview, Expert Opin. Investig. Drugs, 14(7): 769-773 (2005).

Yamamoto et al., "The orally available spleen tyrosine kinase inhibitor 2-[7-(3,4-dimethoxyphenyl)-imidazo [1,2-c] pyrimidin-5-ylamino]-nicotinamide dihydrochloride (Bay 61-3606) blocks antigen-induced airway inflammation in rodents," *J Pharmacol Exp Therapeutics* 306(3):1174-1181 (2003).

Romagnani, S., "The Th1/Th2 paradigm," *Immunology Today*, vol. 18, pp. 263-266 (2001).

Sanz et al., "IL-4-Induced Eosinophil Accumulation in Rat Skin Is Dependent on Endogenous TNF-α and α4 Integrin/VCAM-1 Adhesion Pathways," *J. Immunol.*, vol. 160, pp. 5637-5634 (1998).

Nagata et al., "CRTH2, an orphan receptor of T-helper-2-cells, is express on basophils and eosinophils and response to mast cell-derived factor(s)," *FEBS Lett.*, vol. 459, pp. 195-199 (1999).

Hirai, H. et al., "Prostaglandin D2 Selectivity Induces Chemotaxis in T Helper Type 2 Cells, Eosinophils, and Basophils via Seven-Transmembrane Receptor CRTH2," *J. Exp. Med.*, vol. 193, pp. 255-261 (2001).

Leath, T.M. et al., *Drug Discovery Today*, vol. 10, pp. 1647-1655 (2005).

Hata, A.N & Breyer, R.M., *Pharmacology & Therapeutics*, vol. 103, pp. 147-166 (2004).

*Inpharma Weekly*, Issue 1236, p. 22, May 6, 2000.

Office Action mailed Dec. 9, 2009 in U.S. Appl. No. 10/554,668.

Notice of Allowance mailed May 25, 2010 in U.S. Appl. No. 10/554,668.

* cited by examiner

PYRIMIDINE DERIVATIVES USEFUL FOR THE TREATMENT OF DISEASES MEDIATED BY CRTH2

This application is a continuation of Ser. No. 10/554,668, filed Feb. 9, 2007, now U.S. Pat. No. 7,812,160, which is the U.S. National Stage of International Patent Application No. PCT/EP2004/003910, filed Apr. 14, 2004, which claims priority to European Patent Application No. 03009384.3, filed Apr. 25, 2003, each of which is incorporated herein by reference in its entirety.

DETAILED DESCRIPTION OF INVENTION

1. Technical Field

The present invention relates to a pyrimidine derivative which is useful as an active ingredient of pharmaceutical preparations. The pyrimidine derivative of the present invention has CRTH2 (G-protein-coupled chemoattractant receptor, expressed on Th2 cells) antagonistic activity and can be used for the prophylaxis and treatment of diseases associated with CRTH2 activity, in particular for the treatment of allergic diseases, such as asthma, allergic rhinitis, atopic dermatitis, and allergic conjunctivitis; eosinophil-related diseases, such as Churg-Strauss syndrome and sinusitis; basophil-related diseases, such as basophilic leukemia, chronic urticaria and basophilic leukocytosis in human and other mammals; and inflammatory diseases characterized by T lymphocytes and profuse leukocyte infiltrates such as psoriasis, eczema, inflammatory bowel disease, ulcerative colitis, Crohn's disease, COPD (chronic obstructive pulmonary disorder) and arthritis.

2. Background Art

CRTH2 is a G-protein-coupled chemoattractant receptor, expressed on Th2 cells (Nagata et al. J. Immunol., 162, 1278-1286, 1999), eosinophils and basophils (Hirai et al., 0.1. Exp. Med., 193, 255-261, 2001).

Th2-polarization has been seen in allergic diseases, such as asthma, allergic rhinitis, atopic dermatitis and allergic conjunctivitis (Romagnani S. Immunology Today, 18, 263-266, 1997; Hammad H. et al., Blood, 98, 1135-1141, 2001). Th2 cells regulate allergic diseases by producing Th2 cytokines, such as IL-4, IL-5 and IL-13 (Oriss et al., J. Immunol., 162, 1999-2007, 1999; Viola et al., Blood, 91, 2223-2230, 1998; Webb et al., J. Immunol., 165, 108-113, 2000; Dumont F. J., Exp. Opin. Ther. Pat., 12, 341-367, 2002). These Th2 cytokines directly or indirectly induce migration, activation, priming and prolonged survival of effector cells, such as eosinophils and basophils, in allergic diseases (Sanz et al., J. Immunol., 160, 5637-5645, 1998; Pope et al., J. Allergy Clin. Immunol., 108, 594-601, 2001; Teran L. M., Clin. Exp. Allergy, 29, 287-290, 1999).

$PGD_2$, a ligand for CRTH2, is produced from mast cells and other important effector cells in allergic diseases (Nagata et al., FEBS Lett. 459, 195-199, 1999; Hirai et al., J. Exp. Med., 193, 255-261, 2001). $PGD_2$ induces migration and activation of Th2 cells, eosinophils, and basophils, in human cells via CRTH2 (Hirai et al., J. Exp. Med., 193, 255-261, 2001; Gervais et al., J. Allergy Clin. Immunol., 108, 982-988, 2001; Sugimoto et al., J. Pharmacol. Exp. Ther., 305, (1), 347-52, 2003).

Therefore, antagonists which inhibit the binding of CRTH2 and $PGD_2$ should be useful for the treatment of allergic diseases, such as asthma, allergic rhinitis, atopic dermatitis and allergic conjunctivitis.

In addition, several lines of experimental evidence have demonstrated the contribution of eosinophils in sinusitis (Hamilos et al., Am. J. Respir. Cell and Mol. Biol., 15, 443-450, 1996; Fan et al., J. Allergy Clin. Immunol., 106, 551-558, 2000), and Churg-Strauss syndrome (Coffin et al., J. Allergy Clin. Immunol., 101, 116-123, 1998; Kurosawa et al., Allergy, 55, 785-787, 2000). In the tissues of these patients, mast cells can be observed to be co-localized with eosinophils (Khan et al., J. Allergy Clin. Immunol., 106, 1096-1101, 2000). It is suggested that $PGD_2$ production from mast cells induces the recruitment of eosinophils. Therefore, CRTH2 antagonists are also useful for the treatment of other eosinophil-related diseases such as Churg-Strauss syndrome and sinusitis. CRTH2 antagonists can also be useful for the treatment of some basophil-related diseases such as basophilic leukemia, chronic urticaria and basophilic leukocytosis, because of high expression of CRTH2 on basophils.

Ordukhanyan, A. A et al. discloses the synthesis of pyrimidine derivative represented by the general formula:

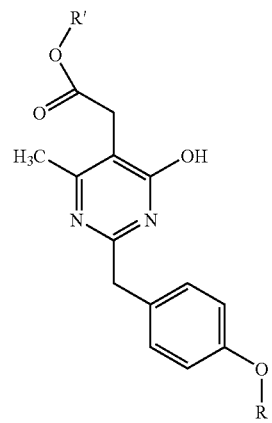

wherein

R=alkyl

R'=H or alkyl as an intermediate for the preparation of antineoplastic agent (Khimiko-Farmatsevticheskii Zhurnal (1979), 13(9), 36-40).

GB2262096 discloses pyrimidine derivative represented by the general formula:

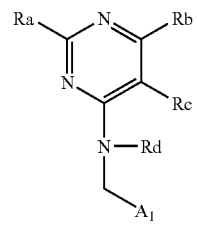

wherein $A_1$, Ra, Rb, Rc, and Rd are defined in the application, as an angiotensin II antagonist.

However, none of the references and other reference discloses pyrimidine derivatives having CRTH2 antagonistic activity.

The development of a compound, which has effective CRTH2 antagonistic activity and can be used for the prophylaxis and treatment of diseases associated with CRTH2 activity, has been desired.

SUMMARY OF THE INVENTION

This invention is to provide a pyrimidine derivative of the formula (I), their tautomeric and stereoisomeric form, or salts, ester or prodrug thereof:

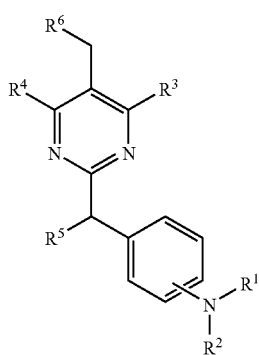

(I)

wherein
R$^1$ represents hydrogen,

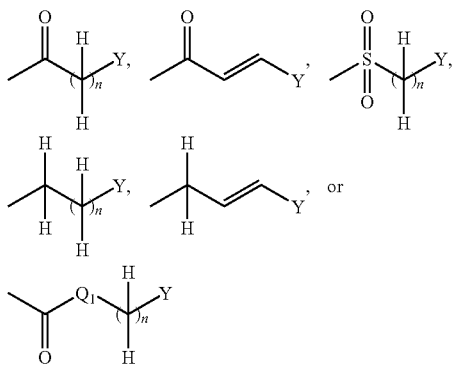

in which
n represents an integer of 0 to 6;
-Q$_1$- represents —NH—, —N(C$_{1-6}$ alkyl)-, or —O—;
Y represents hydrogen, C$_{3-8}$ cycloalkyl optionally substituted by C$_{1-6}$ alkyl, C$_{3-8}$ cycloalkyl fused by benzene, aryl or heteroaryl, wherein said aryl and heteroaryl are optionally substituted at a substitutable position with one or more substituents selected from the group consisting of cyano, halogen, nitro, guanidino, pyrrolyl, sulfamoyl, C$_{1-6}$ alkylaminosulfonyl, di(C$_{1-6}$ alkyl)aminosulfonyl, phenyloxy, phenyl, amino, C$_{1-6}$alkylamino, di(C$_{1-6}$)-alkylamino, C$_{1-6}$alkoxycarbonyl, C$_{1-6}$ alkanoyl, C$_{1-6}$ alkanoylamino, carbamoyl, C$_{1-6}$ alkylcarbamoyl, di-(C$_{1-6}$ alkyl)carbamoyl, C$_{1-6}$ alkyl-sulfonyl, C$_{1-6}$alkyl optionally substituted by mono-, di-, or tri-halogen, C$_{1-6}$ alkoxy optionally substituted by mono-, di-, or tri-halogen and C$_{1-6}$ alkyl-thio optionally substituted by mono-, di-, or tri-halogen,
or aryl fused by 1,3-dioxolane;
R$^2$ represents hydrogen or C$_{1-6}$ alkyl;
R$^3$ represents halogen, C$_{1-6}$ alkoxy optionally substituted by mono-, di-, or tri-halogen,

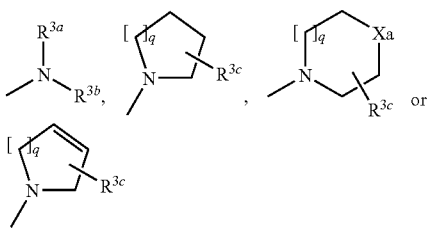

in which
R$^{3a}$ and R$^{3b}$ independently represent C$_{3-8}$ cycloalkyl, or C$_{1-6}$ alkyl which C$_{1-6}$ alkyl optionally substituted by carboxy, C$_{3-8}$ cycloalkyl, carbamoyl, C$_{1-6}$ alkylcarbamoyl, aryl-substituted C$_{1-6}$ alkylcarbamoyl, C$_{1-6}$ alkylcarbamoyl, di(C$_{1-6}$alkyl)carbamoyl, C$_{3-8}$ cycloalkylcarbamoyl, C$_{3-8}$heterocyclocarbonyl, (C$_{1-6}$)alkylamino, di(C$_{1-6}$)alkylamino or C$_{1-6}$ alkoxy,
q represents an integer of 1 to 3;
R$^{3c}$ represents hydrogen, hydroxy, carboxy, or C$_{1-6}$ alkyl optionally substituted by hydroxy, carboxy or (phenyl-substituted C$_{1-6}$ alkyl)carbamoyl;
Xa represents —O—, —S— or —N(R$^{3d}$)—
in which
R$^{3d}$ represents C$_{1-6}$ alkyl;
R$^4$ represents hydrogen, halogen, C$_{1-6}$ alkoxy, di(C$_{1-6}$ alkyl)amino or C$_{1-6}$ alkyl optionally substituted by C$_{1-6}$ alkoxy, or mono-, di-, or tri-halogen;
R$^5$ represents hydrogen, or C$_{1-6}$ alkyl; and
R$^6$ represents carboxy, carboxamide, nitrile or tetrazolyl.
In one embodiment, compounds of the formula (I) are those wherein:
R$^1$ represents

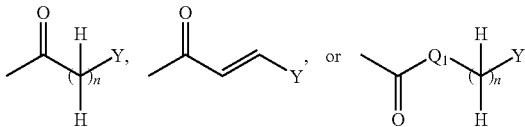

in which
n represents an integer of 0 to 2;
-Q$_1$- represents —NH—, —N(C$_{1-6}$ alkyl)-, or —O—;
Y represents C$_{1-6}$ alkyl, C$_{3-8}$ cycloalkyl optionally substituted by C$_{1-6}$ alkyl, C$_{3-8}$ cycloalkyl fused by benzene selected from the group consisting of indenyl, and tetrahydronaphthyl, aryl selected from the group consisting of phenyl and naphthyl, or heteroaryl selected from the group consisting of indolyl, quinolyl, benzofuranyl, furanyl, chromanyl and pyridyl, wherein said aryl and heteroaryl are optionally substituted at a substitutable position with one or more substituents selected from the group consisting of cyano, halogen, nitro, pyrrolyl, sulfamoyl, C$_{1-6}$ alkylaminasulfonyl, di(C$_{1-6}$ alkyl)aminosulfonyl, phenyloxy, phenyl, C$_{1-6}$alkylamino, di(C$_{1-6}$)-alkylamino, C$_{1-6}$ alkoxycarbonyl, C$_{1-6}$ alkanoylamino, carbamoyl, C$_{1-6}$ alkylcarbamoyl, di-(C$_{1-6}$ alkyl)carbamoyl, C$_{1-6}$ alkylsulfonyl, C$_{1-6}$ alkyl optionally substituted by mono-, di-, or tri-halogen, C$_{1-6}$ alkoxy optionally substituted by mono-, di-, or tri-halogen and C$_{1-6}$ alkylthio optionally substituted by mono-, di-, or tri-halogen; and
R$^2$ represents hydrogen.

In another embodiment, compounds of the formula (I) are those wherein:

$R^3$ represents $C_{1-6}$ alkoxy optionally substituted by mono-, di-, or tri-halogen,

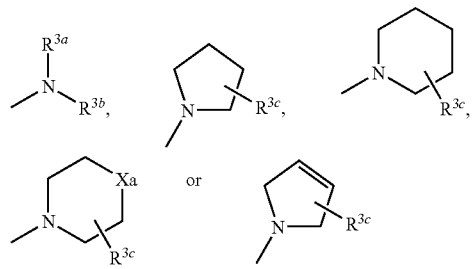

in which $R^{3a}$ and $R^{3b}$ independently represent $C_{1-6}$ alkyl optionally substituted by carboxy, hydroxy, $C_{3-8}$ cycloalkyl, carbamoyl, $C_{1-6}$ alkylcarbamoyl, di($C_{1-6}$ alkyl carbamoyl, $C_{3-8}$ cycloalkylcarbamoyl, $C_{3-8}$ heterocyclocarbonyl, ($C_{1-6}$)-alkylamino, di($C_{1-6}$)alkylamino or $C_{1-6}$ alkoxy, $R^{3c}$ represents hydrogen, hydroxy, carboxy, or $C_{1-6}$ alkyl optionally substituted by hydroxy, carboxy or (phenyl-substituted $C_{1-6}$ alkyl)carbamoyl; and Xa represents —O—, —S— or —N($R^{3d}$)—,
in which
$R^{3d}$ represents $C_{1-6}$ alkyl.

In another embodiment, compounds of the formula (I-i) are those wherein:

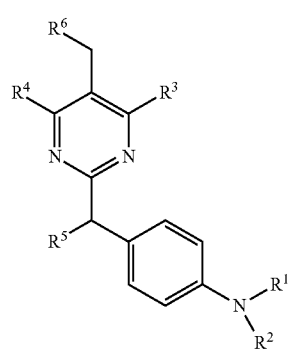

(I-i)

$R^1$ represents

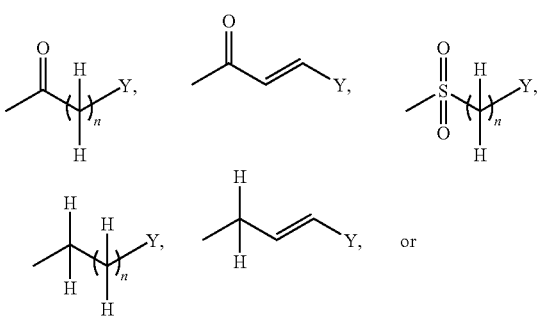

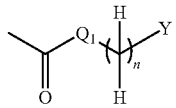

in which n represents an integer of 0 to 2;
-$Q_1$- represents —NH—, —N($C_{1-6}$alkyl)-, or —O—;
Y represents phenyl, naphthyl, indolyl, quinolyl, benzofuranyl, furanyl or pyridyl,
wherein said phenyl, naphthyl, indolyl, quinolyl, benzofuranyl, furanyl and pyridyl are optionally substituted at a substitutable position with one or two substituents selected from the group consisting of cyano, halogen, nitro, phenyloxy, phenyl, $C_{1-6}$ alkyl optionally substituted by mono-, di-, or tri-halogen, $C_{1-6}$ alkoxy optionally substituted by mono-, di-, or tri-halogen and $C_{1-6}$ alkylthio optionally substituted by mono-, di-, or tri-halogen;

$R^2$ represents hydrogen or $C_{1-6}$ alkyl;
$R^3$ represents

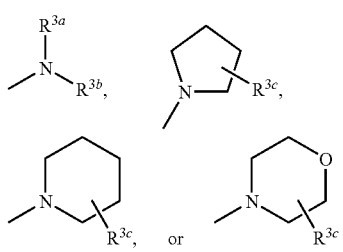

in which $R^{3a}$ and $R^{3b}$ independently represent $C_{3-8}$ cycloalkyl, or $C_{1-6}$ alkyl optionally substituted by $C_{3-8}$ cycloalkyl, carbamoyl, $C_{1-6}$ alkylcarbamoyl, phenyl-substituted $C_{1-6}$ alkylcarbamoyl, $C_{1-6}$ alkylcarbamoyl, di($C_{1-6}$ alkyl)-carbamoyl, $C_{3-8}$ cycloalkylcarbamoyl, $C_{3-8}$heterocyclocarbonyl, ($C_{1-6}$)alkylamino, di($C_{1-6}$) alkylamino or $C_{1-6}$ alkoxy, $R^{3c}$ represents hydrogen, hydroxy, carboxy, or $C_{1-6}$ alkyl optionally substituted by hydroxy, carboxy or (phenyl-substituted $C_{1-6}$ alkyl)carbamoyl;

$R^4$ represents hydrogen, chloro, bromo, $C_{1-6}$ alkoxy, di($C_{1-6}$ alkyl)amino or $C_{1-6}$ alkyl;
$R^5$ represents hydrogen, or methyl;
$R^6$ represents carboxy or tetrazolyl.

The preferable compounds of the present invention are as follows:

{4-chloro-6-(dimethylamino)-2-[4-(2-naphthoylamino)benzyl]-5-pyrimidinyl}acetic acid;
{4-chloro-6-{methyl[2-oxo-2-(1-pyrrolidinyl)ethyl]amino}-2-[4-(2-naphthoylamino)benzyl]-5-pyrimidinyl}acetic acid;
{4-chloro-6-[[2-(isopropylamino)-2-oxoethyl](methyl)amino]-2-[4-(2-naphthoylamino)benzyl]-5-pyrimidinyl}acetic acid;
{4-chloro-[[2-(cyclohexylamino)-2-oxoethyl](methyl)amino]-2-[4-(2-naphthoylamino)benzyl]-5-pyrimidinyl}acetic acid;
{2-[4-(benzoylamino)benzyl]-4-chloro-6-[[2-(cyclopentylamino)-2-oxoethyl](methyl)amino]-5-pyrimidinyl}acetic acid;

{4-chloro-2-{4-[(cyclohexylacetyl)amino]benzyl}-6-[[2-(cyclopentylamino)-2-oxoethyl](methyl)-amino]-5-pyrimidinyl}acetic acid;
(4-chloro-6-[[2-(cyclopentylamino)-2-oxoethyl](methyl)amino]-2-{4-[(3-phenylpropanoyl)amino]benzyl}-5-pyrimidinyl)acetic acid;
[4-chloro-6-[[2-(cyclopentylamino)-2-oxoethyl](methyl)amino]-2-(4-{[(4-methylphenyl)acetyl]-amino}benzyl)-5-pyrimidinyl]acetic acid;
(4-chloro-6-[[2-(cyclopentylamino)-2-oxoethyl](methyl)amino]-2-{4-[(2-quinolinylcarbonyl)-amino]benzyl}-5-pyrimidinyl)acetic acid;
[4-chloro-6-[[2-(cyclopentylamino)-2-oxoethyl](methyl)amino]-2-(4-{[(2E)-3-phenyl-2-propenoyl]amino}benzyl)-5-pyrimidinyl]acetic acid;
{4-chloro-2-{4-[(4-chlorobenzoyl)amino]benzyl}-6-6-[[2-(cyclopentylamino)-2-oxoethyl](methyl)amino]-5-pyrimidinyl}acetic acid;
{4-chloro-6-[[2-(cyclopentylamino)-2-oxoethyl](methyl)amino]-2-{4-[(3,4-dichlorobenzoyl)-amino]benzyl}-5-pyrimidinyl}acetic acid;
{4-chloro-6-[[2-(cyclopentylamino)-2-oxoethyl](methyl)amino]-2-[4-[(4-methoxybenzoyl)amino]benzyl}-5-pyrimidinyl}acetic acid;
{4-chloro-6-[[2-(cyclopentylamino)-2-oxoethyl](methyl)amino]-2-{4-[(4-methylbenzoyl)amino]-benzyl}-5-pyrimidinyl}acetic acid;
{4-chloro-6-[[2-(cyclopentylamino)-2-oxoethyl](methyl)amino]-2-[4-(1-naphthoylamino)benzyl]-5-pyrimidinyl}acetic acid;
{2-{4-[(1-benzofuran-2-ylcarbonyl)amino]benzyl}-4-chloro-6-[[2-(cyclopentylamino)-2-oxoethyl](methyl)amino]-5-pyrimidinyl}acetic acid;
{4-chloro-6-{[2-(cyclopentylamino)-2-oxoethyl](methyl)amino}-2-(4-[(1H-indol-2-ylcarbonyl)-amino]benzyl}-5-pyrimidinyl}acetic acid;
{4-chloro-2-{4-[(4-cyanobenzoyl)amino]benzyl}-6-[[2-(cyclopentylamino)-2-oxoethyl](methyl)-amino]-5-pyrimidinyl}acetic acid;
{4-chloro-6-[[2-(cyclopentylamino)-2-oxoethyl](methyl)amino]-2-{4-[(2,3-dihydro-1H-inden-2-ylacetyl)amino]benzyl}-5-pyrimidinyl}acetic acid;
[4-chloro-6-[[2-(cyclopentylamino)-2-oxoethyl](methyl)amino]-2-(4-{[(3-phenoxyphenyl)acetyl]-amino}benzyl)-5-pyrimidinyl]acetic acid;
[4-chloro-6-[[2-(cyclopentylamino)-2-oxoethyl](methyl)amino]-2-(4-{[(4-phenoxyphenyl)acetyl)-amino]benzyl}-5-pyrimidinyl]acetic acid;
(4-chloro-6-(dimethylamino)-2-{4-[(2-quinolinylcarbonyl)amino]benzyl}-5-pyrimidinyl)acetic acid;
[4-chloro-6-(dimethylamino)-2-(4-{[(2E)-3-phenyl-2-propenoyl]amino}benzyl)-5-pyrimidinyl]acetic acid;
[4-chloro-2-{-4-[(3,4-dichlorobenzoyl)amino]benzyl}-6-(dimethylamino)-5-pyrimidinyl]acetic acid;
[4-chloro-2-{4-[(4-chlorobenzoyl)amino]benzyl}-6-(dimethylamino)-5-pyrimidinyl]acetic acid;
(4-chloro-6-(dimethylamino)-2-{4-[(4-methoxybenzoyl)-amino]benzyl}-5-pyrimidinyl)acetic acid;
[4-chloro-6-(dimethylamino)-2-(4-{[4-(dimethylamino)benzoyl]amino}benzyl)-5-pyrimidinyl]-acetic acid;
[4-chloro-2-{4-[(3,4-dimethoxybenzoyl)amino]benzyl}-6-(dimethylamino)-5-pyrimidinyl]acetic acid;
[4-chloro-6-(dimethylamino)-2-(4-{[4-(trifluoromethyl)benzoyl]amino}benzyl)-5-pyrimidinyl]-acetic acid;
[4-chloro-2-(4-{[(2E)-3-(4-chlorophenyl)-2-propenoyl]amino}benzyl)-6-(dimethylamino)-5-pyrimidinyl]acetic acid;
[2-{4-[(4-bromobenzoyl)amino]benzyl}-4-chloro-6-(dimethylamino)-5-pyrimidinyl]acetic acid;
[4-chloro-2-{4-[(2,5-dichlorobenzoyl)amino]benzyl}-6-(dimethylamino)-5-pyrimidinyl]acetic acid;
[4-chloro-2-{4-[(3,4-difluorobenzoyl)amino]benzyl}-6-(dimethylamino)-5-pyrimidinyl]acetic acid;
[4-chloro-2-{4-[(3,5-dichlorobenzoyl)amino]benzyl}-6-(dimethylamino)-5-pyrimidinyl]acetic acid;
[4-chloro-2-{4-[(3-chlorobenzoyl)amino]benzyl}-6-(dimethylamino)-5-pyrimidinyl]acetic acid;
(4-chloro-6-(dimethylamino)-2-{4-[(3-methoxybenzoyl)amino]benzyl}-5-pyrimidinyl)acetic acid;
{4-chloro-6-(dimethylamino)-2-[3-(2-naphthoylamino)benzyl]-5-pyrimidinyl}acetic acid;
[2-(4-{[(4-tert-butylcyclohexyl)carbonyl]amino}benzyl)-4-chloro-6-(dimethylamino)-5-pyrimidinyl]acetic acid;
[4-chloro-2-{4-[(4-nitrobenzoyl)amino]benzyl}-6-(1-pyrrolidinyl)-5-pyrimidinyl]acetic acid;
[2-(4-{[4-(acetylamino)benzoyl]amino}benzyl)-4-chloro-6-(1-pyrrolidinyl)-5-pyrimidinyl]acetic acid;
[4-chloro-2-{4-[(4-phenoxybenzoyl)amino]benzyl}-6-(1-pyrrolidinyl)-5-pyrimidinyl]acetic acid;
[4-chloro-2-{4-[(4-isopropoxybenzoyl)amino]benzyl}-6-(1-pyrrolidinyl)-5-pyrimidinyl]acetic acid;
[4-chloro-6-(1-pyrrolidinyl)-2-(4-{[4-(1H-pyrrol-1-yl)benzoyl]amino}benzyl)-5-pyrimidinyl]acetic acid;
[4-chloro-2-{4-[(4-methoxy-3-nitrobenzoyl)amino]benzyl}-6-(1-pyrrolidinyl)-5-pyrimidinyl]acetic acid;
[4-chloro-2-{4-[(4-methoxy-3,5-dimethylbenzoyl)amino]benzyl}-6-(1-pyrrolidinyl)-5-pyrimidinyl]acetic acid;
[4-chloro-2-(4-{[(2E)-3-phenyl-2-propenoyl]amino}benzyl)-6-(1-pyrrolidinyl)-5-pyrimidinyl]-acetic acid;
[4-chloro-2-{4-[(3,4-dichlorobenzoyl)amino]benzyl}-6-(1-pyrrolidinyl)-5-pyrimidinyl]acetic acid;
{4-chloro-6-[[2-(cyclopentylamino)-2-oxoethyl](methyl)amino]-2-[4-(2-naphthoylamino)benzyl]-5-pyrimidinyl}acetic acid;
(4-chloro-2-{4-[(4-chlorobenzoyl)amino]benzyl}-6-pyrrolidin-1-ylpyrimidin-5-yl)acetic acid;
[4-chloro-6-pyrrolidin-1-yl-2-(4-{[4-(trifluoromethyl)benzoyl]amino}benzyl)pyrimidin-5-yl]acetic acid;
[4-chloro-2-(4-{[(2E)-3-(4-chlorophenyl)prop-2-enoyl]amino}benzyl)-6-pyrrolidin-1-ylpyrimidin-5-yl]acetic acid;
{4-chloro-6-[(2-hydroxyethyl)(methyl)amino]-2-[4-(2-naphthoylamino)benzyl]pyrimidin-5-yl}acetic acid;
[4-chloro-2-(4-{[(2S)-3,4-dihydro-2H-chromen-2-ylcarbonyl]amino}benzyl)-6-(dimethylamino)-pyrimidin-5-yl]acetic acid;
{4-chloro-6-(dimethylamino)-2-[4-({(2E)-3-[4-(trifluoromethyl)phenyl]prop-2-enoyl}amino)-benzyl]pyrimidin-5-yl}acetic acid;
{4-(dimethylamino)-2-[4-(2-naphthoylamino)benzyl]-5-pyrimidinyl}acetic acid;
{4-[[2-(cyclopentylamino)-2-oxoethyl](methyl)amino]-2-[4-(2-naphthoylamino)benzyl]-5-pyrimidinyl}acetic acid;
{4-{methyl[2-oxo-2-(1-pyrrolidinyl)ethyl]amino}-2-[4-(2-naphthoylamino)benzyl]-5-pyrimidinyl}acetic acid;
{2-[4-(benzoylamino)benzyl]-4-[[2-(cyclopentylamino)-2-oxoethyl](methyl)amino]-5-pyrimidinyl}acetic acid;
[4-[[2-(cyclopentylamino)-2-oxoethyl](methyl)amino]-2-(4-{[(2E)-3-phenyl-2-propenoyl]amino}benzyl)-5-pyrimidinyl]acetic acid;
[2-{4-[(4-chlorobenzoyl)amino]benzyl}-4-(dimethylamino)-5-pyrimidinyl]acetic acid;

(4-(dimethylamino)-2-{4-[(4-methoxybenzoyl)amino]benzyl}-5-pyrimidinyl)acetic acid;
[2-{4-[(3,4-dichlorobenzoyl)amino]benzyl}-4-(dimethylamino)-5-pyrimidinyl]acetic acid;
(4-(dimethylamino)-2-{4-[(2-quinolinylcarbonyl)amino]benzyl}-5-pyrimidinyl)acetic acid;
[4-(dimethylamino)-2-(4-{[(2E)-3-phenyl-2-propenoyl]amino}benzyl)-5-pyrimidinyl]acetic acid;
[2-(4-{[(2E)-3-(4-chlorophenyl)-2-propenoyl]amino}benzyl)-4-(dimethylamino)-5-pyrimidinyl]-acetic acid;
[4-(dimethylamino)-2-(4-{[4-(trifluoromethyl)benzoyl]amino}benzyl)-5-pyrimidinyl]acetic acid;
(4-(dimethylamino)-2-{4-[(3-methoxybenzoyl)amino]benzyl}-5-pyrimidinyl)acetic acid;
[2-{4-[(3-chlorobenzoyl)amino]benzyl}-4-(dimethylamino)-5-pyrimidinyl]acetic acid;
[2-{4-[(4-bromobenzoyl)amino]benzyl}-4-(dimethylamino)-5-pyrimidinyl]acetic acid;
{4-(dimethylamino)-2-[4-({(2E)-3-[4-(trifluoromethyl)phenyl]prop-2-enoyl}amino)benzyl]pyrimidin-5-yl}acetic acid;
(4-(dimethylamino)-2-{1-[4-(2-naphthoylamino)phenyl]ethyl}pyrimidin-5-yl)acetic acid;
[4-(dimethylamino)-2-(4-{[4-(trifluoromethoxy)benzoyl]amino}benzyl)pyrimidin-5-yl]acetic acid;
(4-(dimethylamino)-2-{4-[(4-fluorobenzoyl)amino]benzyl}pyrimidin-5-yl)acetic acid;
[2-(1-{4-[(3,4-dichlorobenzoyl)amino]phenyl}ethyl)-4-(dimethylamino)pyrimidin-5-yl]acetic acid;
{4-(dimethylamino)-2-[1-(4-{[4-(trifluoromethyl)benzoyl]amino}phenyl)ethyl]pyrimidin-5-yl}acetic acid;
{4-(dimethylamino)-2-[1-(4-{[(2E)-3-phenylprop-2-enoyl]amino}phenyl)ethyl]pyrimidin-5-yl}acetic acid;
[4-(dimethylamino)-2-(1-{4-[(quinolin-2-ylcarbonyl)amino]phenyl}ethyl)pyrimidin-5-yl]acetic acid;
[2-(1-{4-[(4-chlorobenzoyl)amino]phenyl}ethyl)-4-(dimethylamino)pyrimidin-5-yl]acetic acid;
[4-(dimethylamino)-2-(1-{4-[(4-fluorobenzoyl)amino]phenyl}ethyl)pyrimidin-5-yl]acetic acid;
(4-pyrrolidin-1-yl-2-{4-[(quinolin-2-ylcarbonyl)amino]benzyl}pyrimidin-5-yl)acetic acid;
(2-{4-[(4-chlorobenzoyl)amino]benzyl}-4-pyrrolidin-1-ylpyrimidin-5-yl)acetic acid;
(2-{4-[(4-fluorobenzoyl)amino]benzyl}-4-pyrrolidin-1-ylpyrimidin-5-yl)acetic acid;
[4-pyrrolidin-1-yl-2-(4-{[4-(trifluoromethyl)benzoyl]amino}benzyl)pyrimidin-5-yl]acetic acid;
{2-[4-(2-naphthoylamino)benzyl]-4-pyrrolidin-1-ylpyrimidin-5-yl}acetic acid;
sodium (2-{4-[(3-methylbutanoyl)amino]benzyl}-4-pyrrolidin-1-ylpyrimidin-5-yl)acetate;
(2-{4-[(3,3-dimethylbutanoyl)amino]benzyl}-4-pyrrolidin-1-ylpyrimidin-5-yl)acetic acid;
[4-chloro-2-[4-(2-naphthoylamino)benzyl]-6-(1-pyrrolidinyl)-5-pyrimidinyl]acetic acid;
N-{5-(carboxymethyl)-6-chloro-2-[4-(2-naphthoylamino)benzyl]-4-pyrimidinyl}-N-methylglycine;
{4-chloro-6-[cyclohexyl(methyl)amino]-2-[4-(2-naphthoylamino)benzyl]-5-pyrimidinyl}acetic acid;
{4-chloro-6-[isopropyl(methyl)amino]-2-[4-(2-naphthoylamino)benzyl]-5-pyrimidinyl}acetic acid;
{4-chloro-6-[(2-methoxyethyl)(methyl)amino]-2-[4-(2-naphthoylamino)benzyl]-5-pyrimidinyl}acetic acid;
{4-chloro-6-(4-morpholinyl)-2-[4-(2-naphthoylamino)benzyl]-5-pyrimidinyl}acetic acid;
[4-chloro-2-[4-(2-naphthoylamino)benzyl]-6-(1-piperidinyl)-5-pyrimidinyl]acetic acid;
(4-chloro-6-(dimethylamino)-2-{4-[(1H-indol-6-ylcarbonyl)amino]benzyl}-5-pyrimidinyl)acetic acid;
{4-chloro-6-methoxy-2-[4-(2-naphthoylamino)benzyl]-5-pyrimidinyl}acetic acid;
{4-chloro-6-(2,5-dihydro-1H-pyrrol-1-yl)-2-[4-(2-naphthoylamino)benzyl]-5-pyrimidinyl}acetic acid;
{4-chloro-6-(diethylamino)-2-[4-(2-naphthoylamino)benzyl]-5-pyrimidinyl}acetic acid;
{4-chloro-6-[ethyl(methyl)amino]-2-[4-(2-naphthoylamino)benzyl]-5-pyrimidinyl}acetic acid;
{4-chloro-6-(3-hydroxy-1-pyrrolidinyl)-2-[4-(2-naphthoylamino)benzyl]-5-pyrimidinyl}acetic acid;
1-{5-(carboxylmethyl)-6-chloro-2-[4-(2-naphthoylamino)benzyl]-4-pyrimidinyl}-L-proline;
[4-chloro-2-(4-{[4-(methylthio)benzoyl]amino}benzyl)-6-(1-pyrrolidinyl)-5-pyrimidinyl]acetic acid;
[4-chloro-2-{4-[(3-chloro-4-methoxybenzoyl)amino]benzyl}-6-(1-pyrrolidinyl)-5-pyrimidinyl]-acetic acid;
{2-{4-[(anilinocarbonyl)amino]benzyl}-4-chloro-6-[[2-(cyclopentylamino)-2-oxoethyl](methyl)-amino]-5-pyrimidinyl}acetic acid;
{2-(4-{[(benzylamino)carbonyl]amino}benzyl)-4-chloro-6-[[2-(cyclopentylamino)-2-oxoethyl]-(methyl)amino]-5-pyrimidinyl}acetic acid;
{4-chloro-6-[[2-(cyclopentylamino)-2-oxoethyl](methyl)amino]-2-[4-({[(2-phenylethyl)-amino]carbonyl}amino)benzyl]-5-pyrimidinyl}acetic acid;
[4-chloro-6-[[2-(cyclopentylamino)-2-oxoethyl](methyl)amino]-2-(4-{[(2-naphthylamino)-carbonyl]amino}benzyl)-5-pyrimidinyl]acetic acid;
[2-(4-{[(benzylamino)carbonyl]amino}benzyl)-4-(dimethylamino)pyrimidin-5-yl]acetic acid;
[2-[(4-({[benzyl(methyl)amino]carbonyl}amino)benzyl]-4-(dimethylamino)pyrimidin-5-yl]acetic acid;
{4-(dimethylamino)-6-(4-morpholinyl)-2-[4-(2-naphthoylamino)benzyl]-5-pyrimidinyl}acetic acid;
[4,6-bis(dimethylamino)-2-(4-{[4-(trifluoromethyl)benzoyl]amino}benzyl)pyrimidin-5-yl]acetic acid;
{4,6-bis(dimethylamino)-2-[4-(2-naphthoylamino)benzyl]-5-pyrimidinyl}acetic acid;
[4-(dimethylamino)-2-[4-(2-naphthoylamino)benzyl]-6-(1-pyrrolidinyl)-5-pyrimidinyl]acetic acid;
[4-(dimethylamino)-2-[4-(2-naphthoylamino)benzyl]-6-(1-piperidinyl)-5-pyrimidinyl]acetic acid;
[2-{4-[(3,4-dichlorobenzoyl)amino]benzyl}-4,6-bis(dimethylamino)pyrimidin-5-yl]acetic acid;
[4,6-bis(dimethylamino)-2-(4-{[(2E)-3-phenylprop-2-enoyl]amino}benzyl)pyrimidin-5-yl]acetic acid;
[2-(4-{[((2E)-3-(4-chlorophenyl)prop-2-enoyl]amino}benzyl)-4,6-bis(dimethylamino)pyrimidin-5-yl]acetic acid;
[2-(4-{[(2E)-3-(4-chlorophenyl)prop-2-enoyl]amino}benzyl)-4-(dimethylamino)-6-pyrrolidin-1-ylpyrimidin-5-yl]acetic acid;
[4-(dimethylamino)-2-(4-{[(2E)-3-phenylprop-2-enoyl]amino}benzyl)-6-pyrrolidin-1-ylpyrimidin-5-yl]acetic acid;
[4-(dimethylamino)-6-pyrrolidin-1-yl-2-(4-{[4-(trifluoromethyl)benzoyl]amino}benzyl)pyrimidin-5-yl]acetic acid;
[2-{4-[(biphenyl-3-ylcarbonyl)amino]benzyl}-4-(dimethylamino)-6-pyrrolidin-1-ylpyrimidin-5-yl]acetic acid;
[2-{4-[biphenyl-4-ylcarbonyl)amino]benzyl}-4-(dimethylamino)-6-pyrrolidin-1-ylpyrimidin-5-yl]acetic acid;
[2-{4-[(3,4-dichlorobenzoyl)amino]benzyl}-4-(dimethylamino)-6-morpholin-4-ylpyrimidin-5-yl]acetic acid;

[4-(dimethylamino)-6-morpholin-4-yl-2-(4-{[4-(trifluoromethyl)benzoyl]amino}benzyl)pyrimidin-5-yl]acetic acid;
[4-(dimethylamino)-6-morpholin-4-yl-2-(4-{[(2E)-3-phenylprop-2-enoyl]amino}benzyl)pyrimidin-5-yl]acetic acid;
(4-(dimethylamino)-2-{4-[(3-phenoxybenzoyl)amino]benzyl}-6-pyrrolidin-1-ylpyrimidin-5-yl)acetic acid;
(4-(dimethylamino)-2-{4-[(4-phenoxybenzoyl)amino]benzyl}-6-pyrrolidin-1-ylpyrimidin-5-yl)acetic acid;
[4-(dimethylamino)-2-(4-{[(2E)-3-(4-methoxyphenyl)prop-2-enoyl]amino}benzyl)-6-morpholin-4-ylpyrimidin-5-yl]acetic acid;
[4-(dimethylamino)-2-(4-{[(2E)-3-(2-methoxyphenyl)prop-2-enoyl]amino}benzyl)-6-morpholin-4-ylpyrimidin-5-yl]acetic acid;
[2-{4-[(4-chlorobenzoyl)amino]benzyl}-4-(dimethylamino)-6-pyrrolidin-1-ylpyrimidin-5-yl]acetic acid;
[4-methyl-2-[4-(2-naphthoylamino)benzyl]-6-(1-pyrrolidinyl)-5-pyrimidinyl]acetic acid;
[2-{4-[(3,4-dichlorobenzoyl)amino]benzyl}-4-methyl-6-(1-pyrrolidinyl)-5-pyrimidinyl]acetic acid;
{4-(dimethylamino)-6-methyl-2-[4-(2-naphthoylamino)benzyl]pyrimidin-5-yl}acetic acid;
[2-{4-[(3,4-dichlorobenzoyl)amino]benzyl}-4-(dimethylamino)-6-methylpyrimidin-5-yl]acetic acid;
[4-(dimethylamino)-6-methyl-2-(4-{[(2E)-3-phenylprop-2-enoyl]amino}benzyl)pyrimidin-5-yl]acetic acid;
{4-(dimethylamino)-6-(methoxymethyl)-2-[4-(2-naphthoylamino)benzyl]pyrimidin-5-yl}acetic acid;
[4-(dimethylamino)-6-(methoxymethyl)-2-(4-{[4-(trifluoromethyl)benzoyl]amino}benzyl)-pyrimidin-5-yl]acetic acid;
{4-(dimethylamino)-6-ethyl-2-[4-(2-naphthoylamino)benzyl]pyrimidin-5-yl}acetic acid;
[4-(dimethylamino)-6-ethyl-2-(4-{[4-(trifluoromethyl)benzoyl]amino}benzyl)pyrimidin-5-yl]acetic acid;
{4-(dimethylamino)-6-isopropyl-2-[4-(2-naphthoylamino)benzyl]pyrimidin-5-yl}acetic acid;
[4-(dimethylamino)-6-isopropyl-2-(4-{[4-(trifluoromethyl)benzoyl]amino}benzyl)pyrimidin-5-yl]acetic acid;
[2-(4-{[(benzyloxy)carbonyl]amino}benzyl)-4-(dimethylamino)pyrimidin-5-yl]acetic acid;
{4-(dimethylamino)-2-[4-({[(4-fluorobenzyl)oxy]carbonyl}amino)benzyl]pyrimidin-5-yl}acetic acid;
[2-{[(benzyloxy)carbonyl]amino}benzyl)-4-chloro-6-(dimethylamino)pyrimidin-5-yl]acetic acid;
{4-(dimethylamino)-2-[4-({[(4-nitrobenzyl)oxy]carbonyl}amino)benzyl]pyrimidin-5-yl}acetic acid;
{4,6-dichloro-2-[4-(2-naphthoylamino)benzyl]pyrimidin-5-yl}acetic acid;
N-(4-{[5-(2-amino-2-oxoethyl)-4-chloro-6-(dimethylamino)pyrimidin-2-yl]methyl}phenyl)-2-naphthamide;
N-(4-{[4-chloro-6-(dimethylamino)-5-(1H-tetrazol-5-ylmethyl)pyrimidin-2-yl]methyl}phenyl)-2-naphthamide;
and their tautomeric and stereoisomeric form, and salts thereof.

The pyrimidine derivative of the formula (I) shows excellent CRTH2 antagonistic activity. They are, therefore, suitable especially for the prophylaxis and treatment of diseases associated with CRTH2 activity.

More specifically, the pyrimidine derivative of the formula (I) are effective for the treatment or prevention of allergic diseases such as asthma, allergic rhinitis, atopic dermatitis and allergic conjunctivitis.

Compounds of the formula (I) are also useful for the treatment or prevention of diseases such as Churg-Strauss syndrome, sinusitis, basophilic leukemia, chronic urticaria and basophilic leukocytosis, since such diseases are also related to CRTH2 activity.

Further, the present invention provides a medicament, which includes one of the compounds, described above and optionally pharmaceutically acceptable excipients.

The Alkyl per se and "alk" and "alkyl" in alkoxy, alkanoyl, alkylcarbamoyl, alkylthio, alkylamino, alkylaminocarbonyl, alkylaminosulphonyl, alkylsulphonylamino, alkoxycarbonyl, alkoxycarbonyl-amino and alkanoylamino represent a linear or branched alkyl radical having generally 1 to 6, preferably 1 to 4 and particularly preferably 1 to 3 carbon atoms, representing illustratively and preferably methyl, ethyl, n-propyl, isopropyl, tert-butyl, n-pentyl and n-hexyl.

Alkoxy illustratively and preferably represents methoxy, ethoxy, n-propoxy, isopropoxy, tert-butoxy, n-pentoxy and n-hexoxy.

Alkanoyl illustratively and preferably represents acetyl and propanoyl.

Alkylamino represents an alkylamino radical having one or two (independently selected) alkyl substituents, illustratively and preferably representing methylamino, ethylamino, n-propylamino, isopropylamino, tert-butylamino, n-pentylamino, n-hexyl-amino, N,N-dimethylamino, N,N-diethylamino, N-ethyl-N-methylamino, N-methyl-N-n-propylamino, N-isopropyl-N-n-propyl-amino, N-t-butyl-N-methylamino, N-ethyl-N-n-pentylamino and N-n-hexyl-N-methylamino.

Alkylaminocarbonyl or alkylcarbamoyl represents an alkylaminocarbonyl radical having one or two (independently selected) alkyl substituents, illustratively and preferably representing methylaminocarbonyl, ethylaminocarbonyl, n-propylaminocarbonyl, isopropylamino-carbonyl, tert-butylaminocarbonyl, n-pentylaminocarbonyl, n-hexylaminocarbonyl, N,N-dimethylaminocarbonyl, N,N-diethylaminocarbonyl, N-ethyl-N-methylaminocarbonyl, N-methyl-N-n-propylaminocarbonyl, N-isopropyl-N-n-propylaminocarbonyl, N-t-butyl-N-methylaminocarbonyl, N-ethyl-N-n-pentylamino-carbonyl and N-n-hexyl-N-methylaminocarbonyl.

Alkylaminosulphonyl represents an alkylaminosulphonyl radical having one or two (independently selected) alkyl substituents, illustratively and preferably representing methylaminosulphonyl, ethylaminosuiphonyl, n-propylaminosulphonyl, isopropylaminosulphonyl, tert-butylaminosulphonyl, n-pentylaminosulphonyl, n-hexylaminosulphonyl, N,N-dimethylaminosulphonyl, N,N-diethylaminosulphonyl, N-ethyl-N-methylaminosulphonyl, N-methyl-N-n-propylaminosulphonyl, N-isopropyl-N-n-propylaminosulphonyl, N-t-butyl-N-methylaminosulphonyl, N-ethyl-N-n-pentyl-aminosulphonyl and N-n-hexyl-N-methylaminosulphonyl.

Alkylsulphonylamino illustratively and preferably represents methylsulphonylamino, ethylsulphonylamino, n-propylsulphonylamino, isopropylsulphonylamino, tert-butylsulphonylamino, n-pentylsulphonylamino and n-hexylsulphonylamino.

Alkoxycarbonyl illustratively and preferably represents methoxycarbonyl, ethoxycarbonyl, n-propoxycarbonyl, isopropoxycarbonyl, tert-butoxycarbonyl, n-pentoxycarbonyl and n-hexoxycarbonyl. Alkoxycarbonylamino illustratively and preferably represents methoxy-carbonylamino, ethoxycarbonylamino, n-propoxycarbonylamino, isopropoxycarbonylamino, tert-butoxycarbonylamino, n-pentoxycarbonylamino and n-hexoxycarbonylamino.

Alkanoylamino illustratively and preferably represents acetylamino and ethylcarbonylamino.

Cycloalkyl per se and in cycloalkylamino and in cycloalkylcarbonyl represents a cycloalkyl group having generally 3 to 8 and preferably 5 to 7 carbon atoms, illustratively and preferably representing cyclopropyl, cyclobutyl, cyclopentyl, cyclohexyl and cycloheptyl.

Cycloalkylamino represents a cycloalkylamino radical having one or two (independently selected) cycloalkyl substituents, illustratively and preferably representing cyclopropylamino, cyclobutylamino, cyclopentylamino, cyclohexylamino and cycloheptylamino.

Cycloalkylcarbonyl illustratively and preferably represents cyclopropylcarbonyl, cyclobutyl-carbonyl, cyclopentylcarbonyl, cyclohexylcarbonyl and cycloheptylcarbonyl.

Aryl per se and in arylamino and in arylcarbonyl represents a mono- to tricyclic aromatic carbocyclic radical having generally 6 to 14 carbon atoms, illustratively and preferably representing phenyl, naphthyl and phenanthrenyl.

Arylamino represents an arylamino radical having one or two (independently selected) aryl substituents, illustratively and preferably representing phenylamino, diphenylamino and naphthyl amino.

Arylcarbonyl illustratively and preferably represents phenylcarbonyl and naphthylcarbonyl.

Heteroaryl per se and in heteroarylamino and heteroarylcarbonyl represents an aromatic mono- or bicyclic radical having generally 5 to 10 and preferably 5 or 6 ring atoms and up to 5 and preferably up to 4 hetero atoms selected from the group consisting of S, O and N, illustratively and preferably representing thienyl, furyl, pyrrolyl, thiazolyl, oxazolyl, imidazolyl, pyridyl, pyrimidyl, pyridazinyl, indolyl, indazolyl, benzofuranyl, benzothiophenyl, quinolinyl, isoquinolinyl.

Heteroarylamino represents an heteroarylamino radical having one or two (independently selected) heteroaryl substituents, illustratively and preferably representing thienylamino, furylamino, pyrrolylamino, thiazolylamino, oxazolylamino, imidazolyl-amino, pyridylamino, pyrimidylamino, pyridazinylamino, indolylamino, indazolylamino, benzofuranylamino, benzothiophenylamino, quinolinylamino, isoquinolinylamino.

Heteroarylcarbonyl illustratively and preferably represents thienylcarbonyl, furylcarbonyl, pyrrolylcarbonyl, thiazolylcarbonyl, oxazolylcarbonyl, imidazolylcarbonyl, pyridylcarbonyl, pyrimidylcarbonyl, pyridazinylcarbonyl, indolylcarbonyl, indazolylcarbonyl, benzofuranyl-carbonyl, benzothiophenylcarbonyl, quinolinylcarbonyl, isoquinolinylcarbonyl.

Heterocyclyl per se and in heterocyclylcarbonyl represents a mono- or polycyclic, preferably mono- or bicyclic, nonaromatic heterocyclic radical having generally 4 to 10 and preferably 5 to 8 ring atoms and up to 3 and preferably up to 2 hetero atoms and/or hetero groups selected from the group consisting of N, O, S, SO and $SO_2$. The heterocyclyl radicals can be saturated or partially unsaturated. Preference is given to 5- to 8-membered monocyclic saturated heterocyclyl radicals having up to two hetero atoms selected from the group consisting of O, N and S, such as illustratively and preferably tetrahydrofuran-2-yl, pyrrolidin-2-yl, pyrrolidin-3-yl, pyrrolinyl, piperidinyl, morpholinyl, perhydroazepinyl.

Heterocyclylcarbonyl illustratively and preferably represents tetrahydrofuran-2-carbonyl, pyrrolidine-2-carbonyl, pyrrolidine-3-carbonyl, pyrrolinecarbonyl, piperidinecarbonyl, morpholinecarbonyl, perhydroazepinecarbonyl.

EMBODIMENT OF THE INVENTION

Compounds of the formula (I) of the present invention can be, but not limited to be, prepared by combining various known methods. In some embodiments, one or more of the substituents, such as amino group, carboxyl group, and hydroxyl group of the compounds used as starting materials or intermediates are advantageously protected by a protecting group known to those skilled in the art. Examples of the protecting groups are described in "Protective Groups in Organic Synthesis (3rd Edition)" by Greene and Wuts, John Wiley and Sons, New York 1999.

Compounds of the formula (I) of the present invention can be, but not limited to be, prepared by the Method [A], [B], [C], [D], [E], [F], [G], [H], [I] or [J] below.

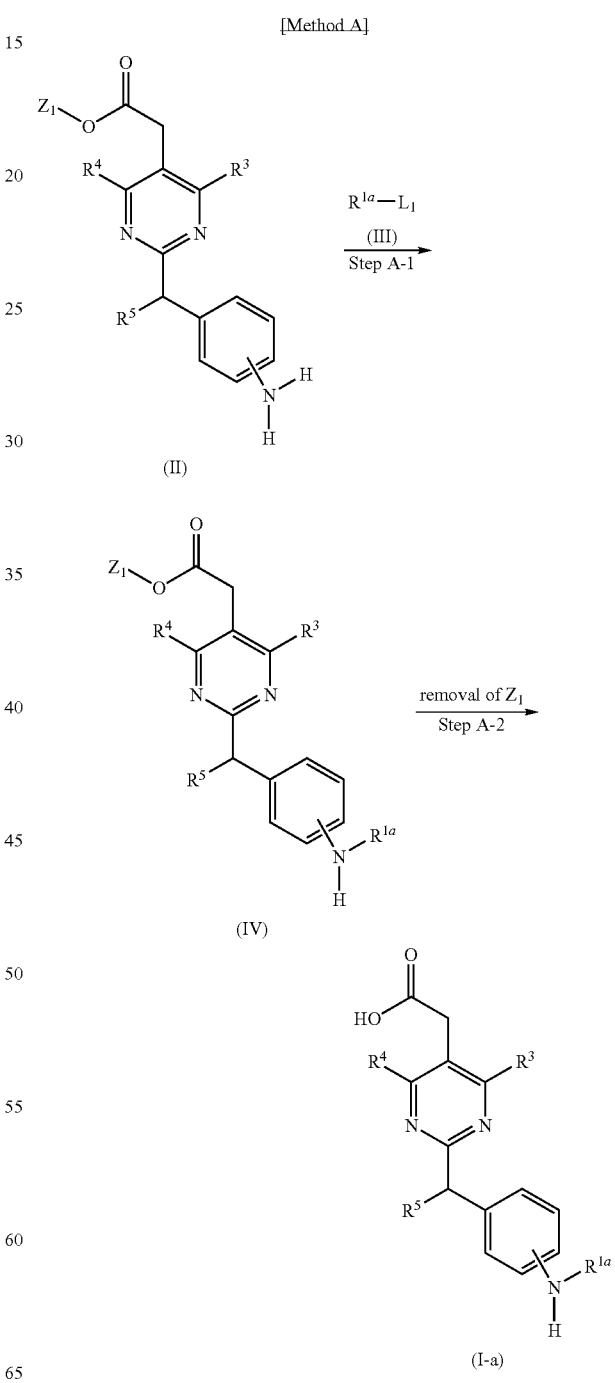

Compounds of the formula (I-a) (wherein $R^3$, $R^4$ and $R^5$ are the same as defined above and $R^{1a}$ is

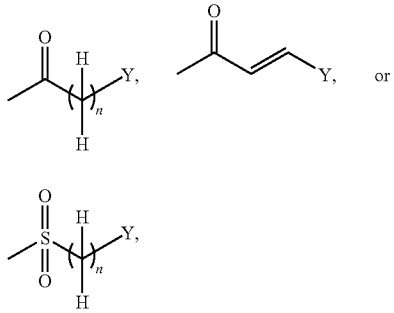

in which n and Y are the same as defined above) can be, for instance, prepared by the following procedures in two steps.

In Step A-1, compounds of the formula (IV) (wherein $R^{1a}$, $R^3$, $R^4$ and $R^5$ are the same as defined above and $Z_1$ is $C_{1-6}$ alkyl, benzyl, 4-methoxybenzyl or 3,4-dimethoxybenzyl) can be prepared by the reaction of compounds of the formula (II) (wherein $R^3$, $R^4$, $R^5$ and $Z_1$ are the same as defined above) with compounds of the formula (III) (wherein $R^{1a}$ is the same as defined above and $L_1$ represents a leaving group including, for instance, halogen atom such as chlorine, bromine and iodine atom, azole such as imidazole and triazole, and hydroxy)

The reaction may be carried out in a solvent including, for instance, halogenated hydrocarbons such as dichloromethane, chloroform and 1,2-dichloroethane; ethers such as diethyl ether, isopropyl ether, dioxane and tetrahydrofuran (THF) and 1,2-dimethoxyethane; aromatic hydrocarbons such as benzene, toluene and xylene; nitriles such as acetonitrile; amides such as N,N-dimethylformamide (DMF), N,N-dimethylacetamide (DMAC) and N-methylpyrrolidone (NMP); urea such as 1,3-dimethyl-2-imidazolidinone (DMI); sulfoxides such as dimethylsulfoxide (DMSO); and others. Optionally, two or more of the solvents selected from the listed above can be mixed and used.

The reaction temperature can be optionally set depending on the compounds to be reacted. The reaction temperature is usually, but not limited to, about 0° C. to 180° C. and preferably about 20° C. to 100° C. The reaction may be conducted for, usually, 30 minutes to 24 hours and preferably 1 hour to 12 hours.

The reaction can be advantageously conducted in the presence of a base including, for instance, sodium carbonate, potassium carbonate, pyridine, triethylamine and N,N-diisopropylethylamine, dimethylaniline, diethylaniline, and others.

In the case $L_1$ in compounds of the formula (III) (wherein $R^{1a}$ is

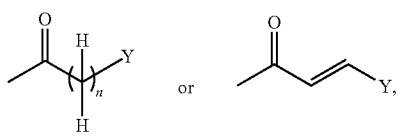

in which n and Y are the same as defined above) represents hydroxy, compounds of the formula (IV) (wherein $R^3$, $R^4$ and $R^5$ and $Z_1$ are the same as defined above and $R^{1a}$ is

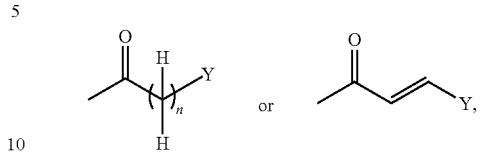

in which n and Y are the same as defined above) can be prepared by the reaction of compounds of the formula (II) (wherein $R^3$, $R^4$, $R^5$ and $Z_1$ are the same as defined above) with compounds of the formula (III) using a coupling agent including, for instance, carbodiimides such as N,N-dicyclohexylcarbodiimide and 1-(3-dimethylaminopropyl)-3-ethylcarbodiimide, benzotriazole-1-yl-oxy-tris-pyrrolidino-phosphonium hexafluorophosphate (PyBOP), diphenylphosphoryl azide. N-hydroxysuccinimide, 1-hydroxybenzothiazole monohydrate (HOBt), and the like can be used as an accelerator of the reaction.

The reaction may be carried out in a solvent including, for instance, halogenated hydrocarbons such as dichloromethane, chloroform and 1,2-dichloroethane; ethers such as diethyl ether, isopropyl ether, dioxane and tetrahydrofuran (THF) and 1,2-dimethoxyethane; aromatic hydrocarbons such as benzene, toluene and xylene; nitriles such as acetonitrile; amides such as N,N-dimethylformamide (DMF), N,N-dimethylacetamide (DMAC) and N-methylpyrrolidone (NMP); urea such as 1,3-dimethyl-2-imidazolidinone (DMI); sulfoxides such as dimethylsulfoxide (DMSO); and others. Optionally, two or more of the solvents selected from the listed above can be mixed and used.

The reaction temperature can be optionally set depending on the compounds to be reacted. The reaction temperature is usually, but not limited to, about 0° C. to 180° C. and preferably about 20° C. to 100° C. The reaction may be conducted for, usually, 30 minutes to 24 hours and preferably 1 hour to 12 hours.

In Step A-2, compounds of the formula (I-a) (wherein $R^{1a}$, $R^3$, $R^4$ and $R^5$ are the same as defined above) can be prepared by the removal of protective group $Z_1$ of compounds of the formula (IV) (wherein $R^{1a}$, $R^3$, $R^4$, $R^5$ and $Z_1$ are the same as defined above).

The removal of protective group $Z_1$ can be conducted by using a base including, for instance, sodium hydroxide, lithium hydroxide and potassium hydroxide, or an acid including, for instance, HCl, HBr, trifluoroacetic acid and $BBr_3$. The deprotection can also be done by hydrogenation using a catalyst including, for instance, palladium on carbon and palladium hydroxide, when $Z_1$ is benzyl, 4-methoxybenzyl or 3,4-dimethoxybenzyl. Also, the deprotection can be done by using a reagent such as eerie ammonium nitrate (CAN) or 2,3-dichloro-5,6-dicyano-1,4-benzoquinone (DDQ), when $Z_1$ is 4-methoxybenzyl or 3,4-dimethoxybenzyl.

The reaction can be carried out in a solvent including, for instance, halogenated hydrocarbons such as dichloromethane, chloroform and 1,2-dichloroethane; ethers such as diethyl ether, isopropyl ether, dioxane and tetrahydrofuran (THF) and 1,2-dimethoxyethane; aromatic hydrocarbons such as benzene, toluene and xylene; N,N-dimethylformamide (DMF), dimethylacetamide (DMAC), 1,3-dimethyl-3,4,5,6-tetrahydro-2(1H)-pyrimidinone (DMPU), 1,3-dimethyl-2-imidazolidinone (DMI), N-methylpyrrolidinone (NMP), sulfoxides such as dimethylsulfoxide (DMSO), alcohols such as methanol, ethanol, 1-propanol, isopropanol and tert-butanol, water and others. Optionally, two or more of the solvents selected from the listed above can be mixed and used.

The reaction temperature can be optionally set depending on the compounds to be reacted. The reaction temperature is usually, but not limited to, about 0° C. to 180° C. and preferably about 20° C. to 100° C. The reaction may be conducted for, usually, 30 minutes to 24 hours and preferably 1 hour to 12 hours.

Compounds of the formula (III) are commercially available or can be synthesized by conventional methods.

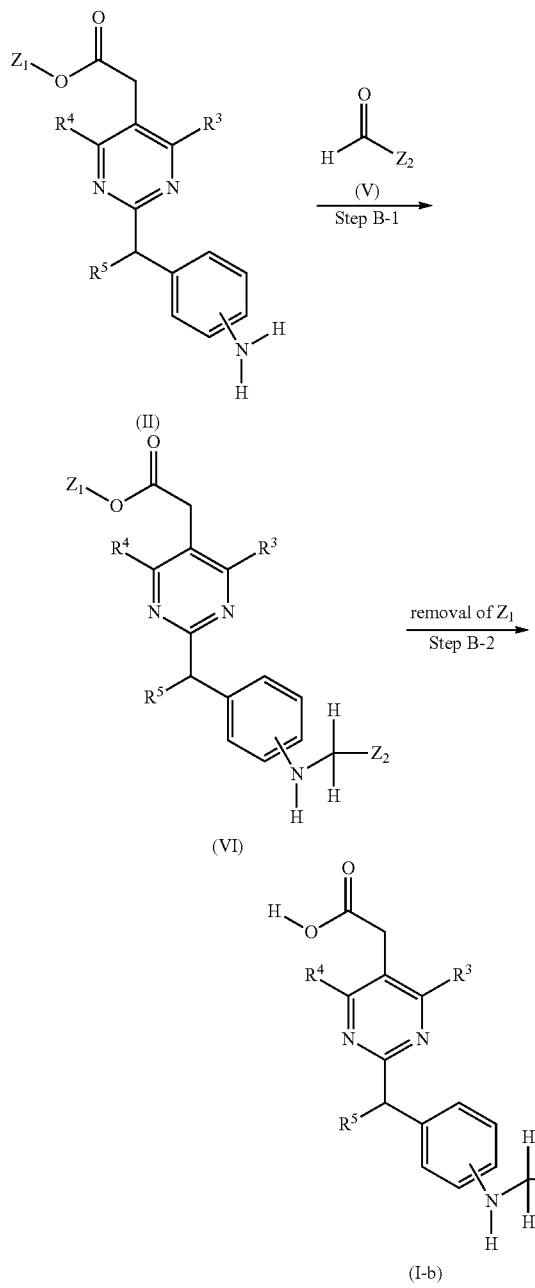

Compounds of the formula (I-b) (wherein $R^3$, $R^4$ and $R^5$ are the same as defined above and $Z_2$ is

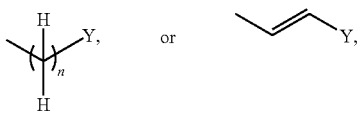

in which n and Y are the same as defined above) can be, for instance, prepared by the following procedures in two steps.

In Step B-1, compounds of the formula (VI) (wherein $R^3$, $R^3$, $R^4$, $R^5$, $Z_1$ and $Z_2$ are the same as defined above) can be prepared by the reaction of compounds of the formula (II) (wherein $R^3$, $R^4$, $R^5$ and $Z_1$ are the same as defined above) with compounds of the formula (V) (wherein $Z_2$ is the same as defined above) using a reducing agent such as sodium triacetoxyborohydride.

The reaction can be advantageously conducted in the presence of a Lewis acid or protic acids, such as acetic acid or hydrochloric acid, or a dehydrating agent such as molecular sieves.

The reaction may be carried out in a solvent including, for instance, halogenated hydrocarbons such as 1,2-dichloroethane, ethers such as diethyl ether, isopropyl ether, dioxane and tetra-hydrofuran (THF) and 1,2-dimethoxyethane; aromatic hydrocarbons such as benzene, toluene and xylene, and others. Optionally, two or more of the solvents selected from the listed above can be mixed and used.

The reaction temperature can be optionally set depending on the compounds to be reacted. The reaction temperature is usually, but not limited to, about 0° C. to 180° C. and preferably about 20° C. to 100° C. The reaction may be conducted for, usually, 30 minutes to 24 hours and preferably 1 hour to 12 hours.

In Step B-2, compounds of the formula (I-b) (wherein $R^3$, $R^4$, $R^5$ and $Z_2$ are the same as defined above) can be prepared by the removal of protective group $Z_1$ of compounds of the formula (VI) (wherein $R^3$, $R^4$, $R^5$, $Z_1$ and $Z_2$ are the same as defined above) in a similar manner of Step A-2 for the preparation of compounds of the formula (I-a).

Compounds of the formula (V) are commercially available or can be synthesized by conventional methods.

[Method C]

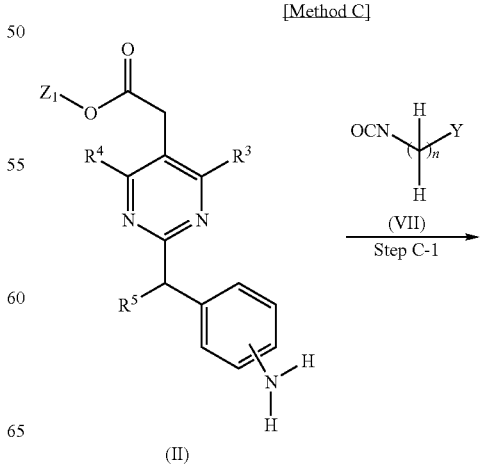

-continued

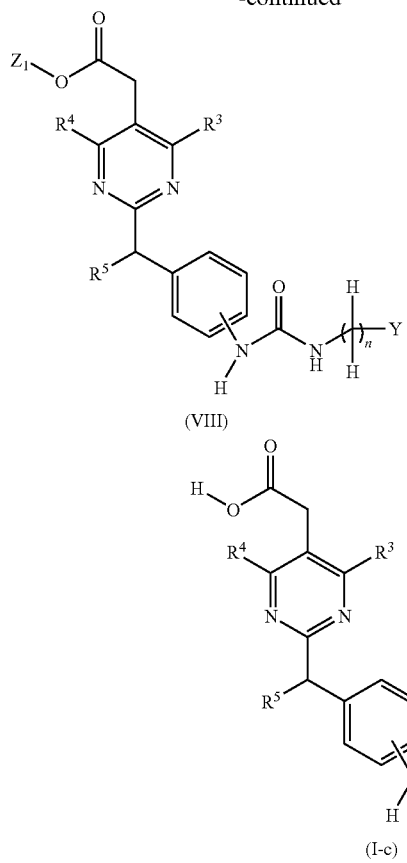

Compounds of the formula (I-c) (wherein n, $R^3$, $R^4$, $R^5$ and Y are the same as defined above) can be, for instance, prepared by the following procedures in two steps.

In Step C-1, Compounds of the formula (VIII) (wherein n, $R^3$, $R^4$, $R^5$, Y and $Z_1$ are the same as defined above) can be prepared by the reaction of compounds of the formula (II) (wherein $R^3$, $R^4$, $R^5$ and $Z_1$ are the same as defined above) with compounds of the formula (VII) (wherein n and Y are the same as defined above)

The reaction may be carried out in a solvent including, for instance, halogenated hydrocarbons such as dichloromethane, chloroform and 1,2-dichloroethane; ethers such as diethyl ether, isopropyl ether, dioxane and tetrahydrofuran (THF) and 1,2-dimethoxyethane; aromatic hydrocarbons such as benzene, toluene and xylene; nitriles such as acetonitrile; amides such as N,N-dimethylformamide (DMF), N,N-dimethylacetamide (DMAC) and N-methylpyrrolidone (NMP); urea such as 1,3-dimethyl-2-imidazolidinone (DMI); sulfoxides such as dimethylsulfoxide (DMSO); and others. Optionally, two or more of the solvents selected from the listed above can be mixed and used.

The reaction temperature can be optionally set depending on the compounds to be reacted. The reaction temperature is usually, but not limited to, about 0° C. to 180° C. and preferably about 20° C. to 100° C. The reaction may be conducted for, usually, 30 minutes to 24 hours and preferably 1 hour to 12 hours.

In Step C-2, compounds of the formula (I-c) (wherein n, $R^3$, $R^4$, $R^5$ and Y are the same as defined above) can be prepared by the removal of protective group $Z_1$ of compounds of the formula (VIII) (wherein n, $R^3$, $R^4$, $R^5$, Y and $Z_1$ are the same as defined above) in a similar manner of Step A-2 for the preparation of compounds of the formula (I-a).

Compounds of the formula (VII) are commercially available or can be synthesized by conventional methods.

[Method D]

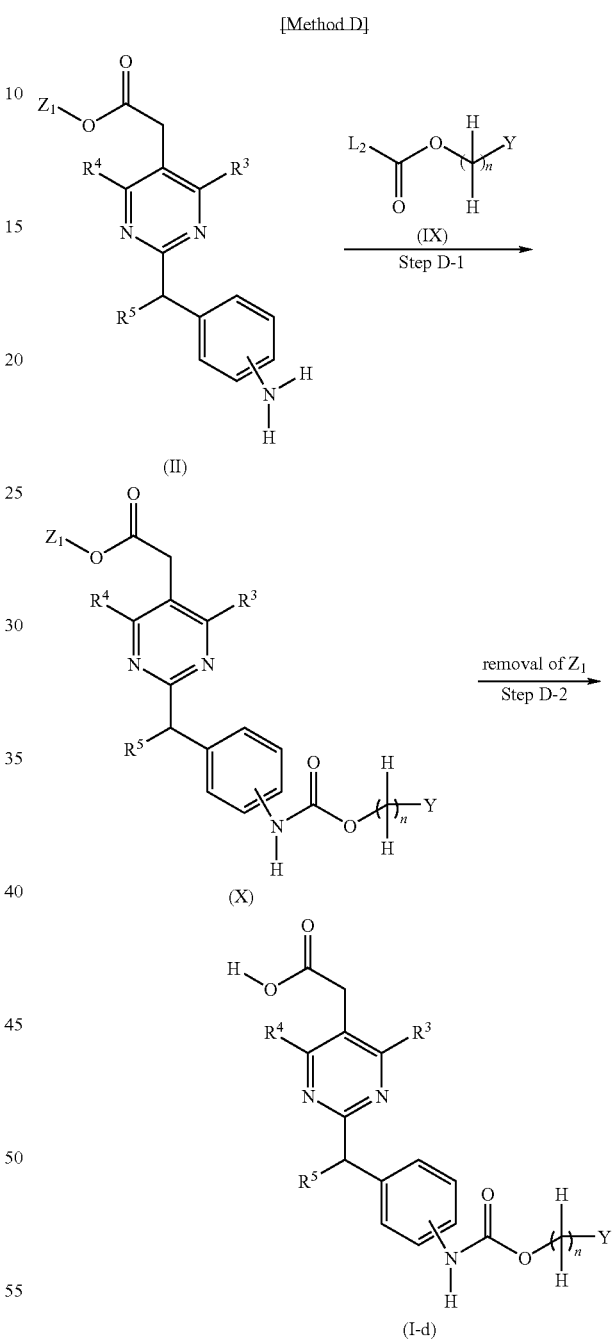

Compounds of the formula (I-d) (wherein n, $R^3$, $R^4$, $R^5$ and Y are the same as defined above) can be, for instance, prepared by the following procedures in two steps.

In Step D-1, compounds of the formula (X) (wherein n, $R^3$, $R^4$, $R^5$, Y and $Z_1$ are the same as defined above) can be prepared by the reaction of compounds of the formula (II) (wherein $R^3$, $R^4$, $R^5$ and $Z_1$ are the same as defined above) with compounds of the formula (IX) (wherein n and Y are the same as defined above and $L_2$ represents a leaving group including, for instance, halogen atom such as chlorine and bromine).

The reaction may be carried out in a solvent including, for instance, halogenated hydrocarbons such as dichloromethane, chloroform and 1,2-dichloroethane; ethers such as diethyl ether, isopropyl ether, dioxane and tetrahydrofuran (THF) and 1,2-dimethoxyethane; aromatic hydrocarbons such as benzene, toluene and xylene; nitriles such as acetonitrile; amides such as N,N-dimethylformamide (DMF), N,N-dimethylacetamide (DMAC) and N-methylpyrrolidone (NMP); urea such as 1,3-dimethyl-2-imidazolidinone (DMI); sulfoxides such as dimethylsulfoxide (DMSO); and others. Optionally, two or more of the solvents selected from the listed above can be mixed and used.

The reaction temperature can be optionally set depending on the compounds to be reacted. The reaction temperature is usually, but not limited to, about 0° C. to 180° C. and preferably about 20° C. to 100° C. The reaction may be conducted for, usually, 30 minutes to 24 hours and preferably 1 hour to 12 hours.

In Step D-2, compounds of the formula (I-d) (wherein n, $R^3$, $R^4$, $R^5$ and Y are the same as defined above) can be prepared by the removal of protective group $Z_1$ of compounds of the formula (VIII) (wherein n, $R^3$, $R^4$, $R^5$, Y and $Z_1$ are the same as defined above) in a similar manner of Step A-2 for the preparation of compounds of the formula (I-a).

Compounds of the formula (IX) are commercially available or can be synthesized by conventional methods.

[Method E]

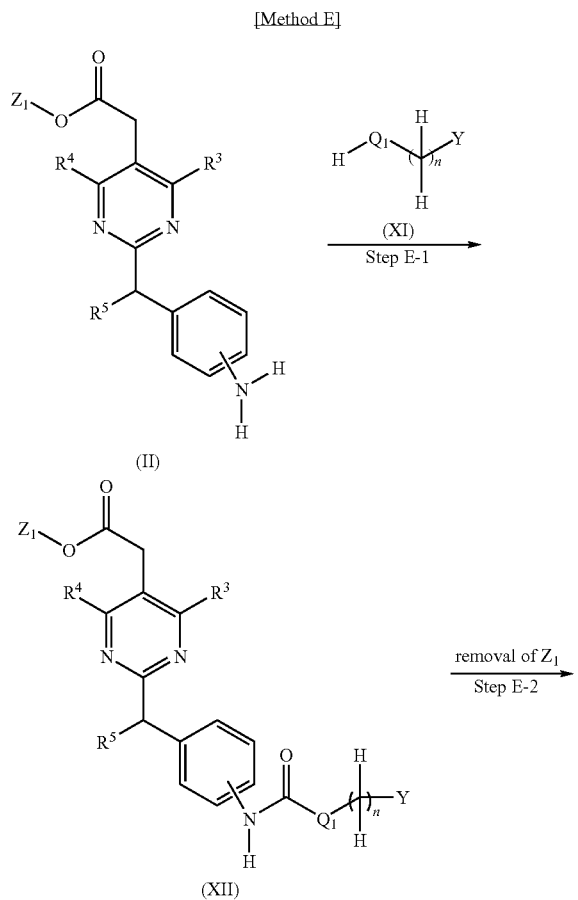

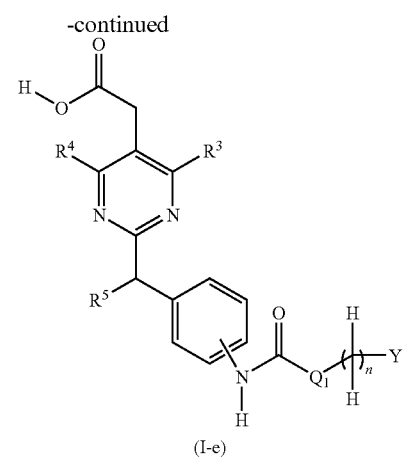

Compounds of the formula (I-e) (wherein n, $R^3$, $R^4$, $R^5$ and Y are the same as defined above and $Q_1$ represents —NH—, —N—$C_{1-6}$ alkyl, or —O—) can be, for instance, prepared by the following procedures in two steps.

In Step E-1, compounds of the formula (XII) (wherein n, $Q_1$, $R^3$, $R^4$, $R^5$, Y and $Z_1$ are the same as defined above) can be prepared by the reaction of compounds of the formula (II) (wherein $R^3$, $R^4$, $R^5$ and $Z_1$ are the same as defined above) with compounds of the formula (XI) (wherein n, $Q_1$ and Y are the same as defined above) and agent including, for instance, aryl formate derivative such as phenyl chloroformate; halocarbonyl derivative such as phosgene, diphosgene, and triphosgene; carbonyldiazole derivative such as 1,1-carbonyldiimidazole (CDI), and 1,1'-carbonyldi(1,2,4-triazole)(CDT), and the like.

The reaction may be carried out in a solvent including, for instance, halogenated hydrocarbons such as dichloromethane, chloroform and 1,2-dichloroethane; ethers such as diethyl ether, isopropyl ether, dioxane and tetrahydrofuran (THF) and 1,2-dimethoxyethane; aromatic hydrocarbons such as benzene, toluene and xylene; nitriles such as acetonitrile; amides such as N,N-dimethylformamide (DMF), N,N-dimethylacetamide (DMAC) and N-methylpyrrolidone (NMP); urea such as 1,3-dimethyl-2-imidazolidinone (DMI); and others. Optionally, two or more of the solvents selected from the listed above can be mixed and used.

The reaction temperature can be optionally set depending on the compounds to be reacted. The reaction temperature is usually, but not limited to, about 0° C. to 180° C. and preferably about 20° C. to 100° C. The reaction may be conducted for, usually, 30 minutes to 24 hours and preferably 1 hour to 12 hours.

The reaction can be advantageously carried out in the presence of a base including, for instance, organic amines such as pyridine, triethylamine and N,N-diisopropylethylamine, dimethylaniline, diethylaniline, 4-dimethylaminopyridine, and others.

In Step E-2, compounds of the formula (I-e) (wherein n, $Q_1$, $R^3$, $R^4$, $R^5$ and Y are the same as defined above) can be prepared by the removal of protective group $Z_1$ of compounds of the formula (XII) (wherein n, $Q_1$, $R^3$, $R^4$, $R^5$, Y and $Z_1$ are the same as defined above) in a similar manner of Step A-2 for the preparation of compounds of the formula (I-a).

Compounds of the formula (XI) are commercially available or can be synthesized by conventional methods.

[Method F]

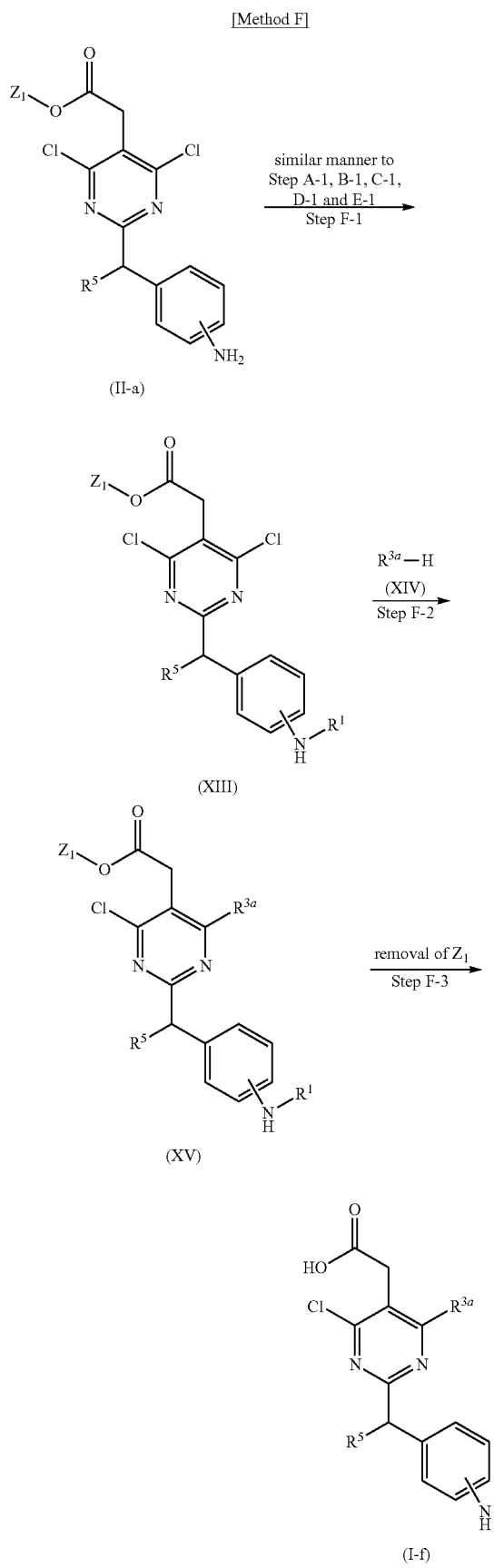

Compounds of the formula (I-f) (wherein $R^1$ and $R^5$ are the same as defined above and $R^{3a}$ has the same significance as $R^3$ as defined above excluding halogen), can be prepared by the following procedures.

In Step F-1, compounds of the formula (XIII) (wherein $R^1$, $R^5$ and $Z_1$ are the same as defined above) can be prepared by the reaction of compounds of the formula (II-a) (wherein $R^5$ and $Z_1$ are the same as defined above) in a similar manner described in Step A-1, B-1, C-1, D-1 and E-1.

In Step F-2, compounds of the formula (XV) (wherein $R^1$, $R^{3a}$, $R^5$ and $Z_1$ are the same as defined above) can be prepared by the reaction of compounds of the formula (XIII) (wherein $R^1$, $R^5$ and $Z_1$ are the same as defined above) with compounds of the formula (XIV) (wherein $R^{3a}$ is the same as defined above).

The reaction may be carried out without solvent or in a solvent including, for instance, ethers such as diethyl ether, isopropyl ether, dioxane and tetrahydrofuran (THF) and 1,2-dimethoxyethane; aromatic hydrocarbons such as benzene, toluene and xylene; nitriles such as acetonitrile; amides such as N,N-dimethylformamide (DMF), N,N-dimethylacetamide (DMAC) and N-methylpyrrolidone (NMP); urea such as 1,3-dimethyl-2-imidazolidinone (DMI); sulfoxides such as dimethylsulfoxide (DMSO); and others. Optionally, two or more of the solvents selected from the listed above can be mixed and used.

The reaction temperature can be optionally set depending on the compounds to be reacted. The reaction temperature is usually, but not limited to, about 0° C. to 180° C. and preferably about 20° C. to 100° C. The reaction may be conducted for, usually, 30 minutes to 24 hours and preferably 1 hour to 12 hours.

The reaction can be advantageously carried out in the presence of a base including, for instance, organic amines such as pyridine, triethylamine, N,N-diisopropylethylamine, dimethylaniline, diethylaniline, and others.

In Step F-3, compounds of the formula (I-f) (wherein $R^1$, $R^{3a}$ and $R^5$ are the same as defined above) can be prepared by the removal of protective group $Z_1$ of compounds of the formula (XV) (wherein $R^1$, $R^{3a}$, $R^5$ and $Z_1$ are the same as defined above) in a similar manner of Step A-2 for the preparation of compounds of the formula (I).

Compounds of the formula (XIV) are commercially available or can be synthesized by conventional methods.

[Method G]

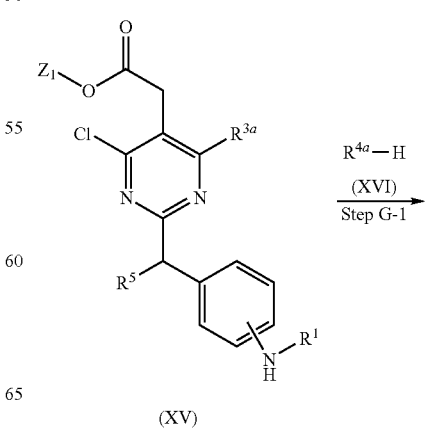

[Method H]

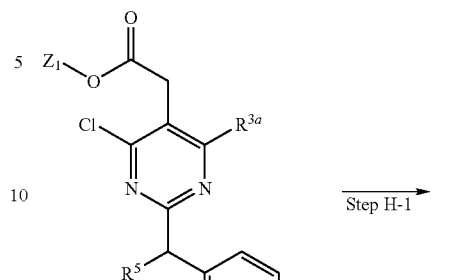

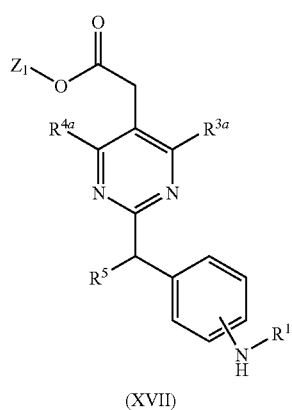

(XVII)

(XV)

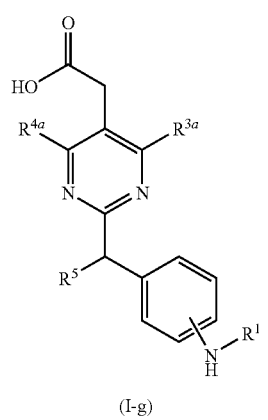

(I-g)

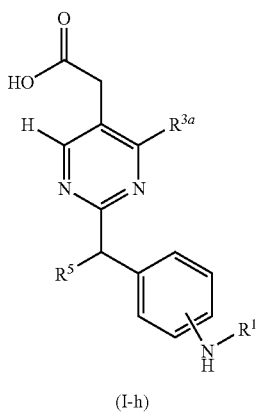

(XVIII)

(I-h)

Compounds of the formula (I-g) (wherein $R^1$, $R^{3a}$ and $R^5$ are the same as defined above and $R^{4a}$ has the same significance as $R^4$ as defined above excluding halogen), can be prepared by the following procedures.

In Step G-1, compounds of the formula (XVII) (wherein $R^1$, $R^{3a}$, $R^{4a}$, $R^5$ and $Z_1$ are the same as defined above) can be prepared by the reaction of compounds of the formula (XV) (wherein $R^1$, $R^{3a}$, $R^5$ and $Z_1$ are the same as defined above) with compounds of the formula (XVI) (wherein $R^{4a}$ is the same as defined above) in a similar manner described in Step F-2 for the preparation of compounds of the formula (XV).

In Step G-2, compounds of the formula (I-g) (wherein $R^1$, $R^{3a}$, $R^{4a}$ and $R^5$ are the same as defined above) can be prepared by the removal of protective group $Z_1$ of compounds of the formula (XVII) (wherein $R^1$, $R^{3a}$, $R^{4a}$, $R^5$ and $Z_1$ are the same as defined above) in a similar manner of Step A-2 for the preparation of compounds of the formula (I).

Compounds of the formula (XVI) are commercially available or can be synthesized by conventional methods.

Compounds of the formula (I-h) (wherein $R^1$, $R^{3a}$ and $R^5$ are the same as defined above), can be prepared by the following procedures.

In Step H-1, compounds of the formula (XVIII) (wherein $R^1$, $R^{3a}$, $R^5$ and $Z_1$ are the same as defined above) can be prepared by the reduction of compounds of the formula (XV) (wherein $R^1$, $R^{3a}$, $R^5$ and $Z_1$ are the same as defined above) by hydrogenation using a catalyst including, for instance, palladium on carbon and platinum on carbon in the presence of a base such as potassium acetate.

The reaction can be carried out in a solvent including, for instance, ethers such as diethyl ether, isopropyl ether, dioxane, tetrahydrofuran (THF) and 1,2-dimethoxyethane, aromatic hydrocarbons such as benzene, toluene and xylene, alcohols such as methanol, ethanol, 1-propanol, isopropanol and tert-butanol, water and others.

The reaction temperature can be optionally set depending on the compounds to be reacted. The reaction temperature is usually, but not limited to, about 0° C. to 180° C. and preferably about 20° C. to 100° C. The reaction may be conducted for, usually, 30 minutes to 24 hours and preferably 1 hour to 12 hours.

In Step H-2, compounds of the formula (I-h) (wherein $R^1$, $R^{3a}$ and $R^5$ are the same as defined above) can be prepared by the removal of protective group $Z_1$ of compounds of the formula (XVIII) (wherein $R^1$, $R^{3a}$, $R^5$ and $Z_1$ are the same as defined above) in a similar manner of Step A-2 for the preparation of compounds of the formula (I).

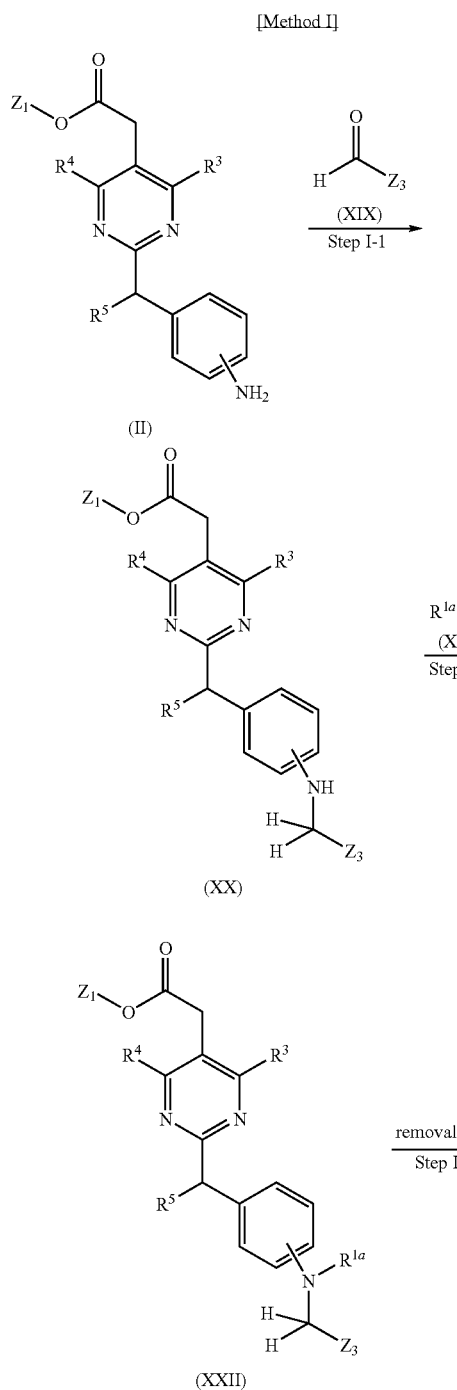

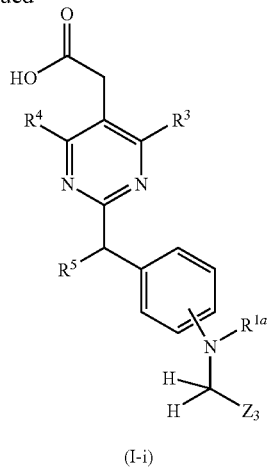

Compounds of the formula (I-i) (wherein $R^3$, $R^4$ and $R^5$ are the same as defined above, $R^{1a}$ represents

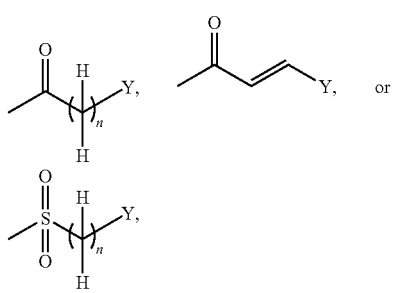

in which n and Y are the same as defined above and $Z_3$ represents hydrogen or $C_{1-5}$ alkyl) can also be prepared by the following procedures.

In Step I-1, compounds of the formula (XX) (wherein $R^3$, $R^4$, $R^5$, $Z_1$ and $Z_3$ are the same as defined above) can be prepared by the reaction of compounds of the formula (II) (wherein $R^3$, $R^4$, $R^5$ and $Z_1$ are the same as defined above) with compounds of the formula (XIX) (wherein $Z_3$ is the same as defined above) in a similar manner described in Step B-1 for the preparation of compounds of the formula (VI).

In Step I-2, compounds of the formula (XXII) (wherein $R^3$, $R^4$, $R^5$, $Z_1$ and $Z_3$ are the same as defined above and $R^{1a}$ represents

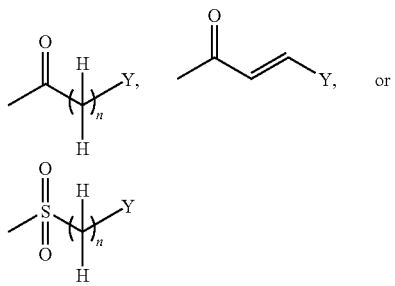

in which n and Y are the same as defined above) can be prepared by the reaction of compounds of the formula (XX) (wherein $R^3$, $R^4$, $R^5$, $Z_1$ and $Z_3$ are the same as defined above)

with compounds of the formula (XXI) (wherein $R^{1a}$ and $L_1$ are the same as defined above) in a similar manner described in Step A-1 for the preparation of compounds of the formula (IV).

In Step I-3, compounds of the formula (I-i) (wherein $R^{1a}$, $R^3$, $R^4$, $R^5$ and $Z_3$ are the same as defined above) can be prepared by the removal of protective group $Z_1$ of compounds of the formula (XXII) (wherein $R^{1a}$, $R^3$, $R^4$, $R^5$, $Z_1$ and $Z_3$ are the same as defined above) in the same manner of Step A-2 for the preparation of compounds of the formula (I).

Compounds of the formula (XIX) and (XXI) are commercially available or can be synthesized by conventional methods.

Preparation of Starting Compounds of Formula (II-a), (II-b), (II-c) and (II-d)

the same as defined above) in a similar manner described in Step G-1 for the preparation of compounds of the formula (XVII).

In Step i-3, compounds of the formula (II-b) (wherein $R^{3a}$, $R^{4a}$, $R^5$ and $Z_1$ are the same as defined above) can be prepared by reducing the nitro group of compounds of the formula (XXV) (wherein $R^{3a}$, $R^{4a}$, $R^5$ and $Z_1$ are the same as defined above) using an agent including, for instance, metals such as zinc and iron in the presence of acid including, for instance, hydrochloric acid and acetic acid, or stannous chloride, or by hydrogenation using a catalyst including, for instance, palladium on carbon and platinum on carbon.

The reaction can be carried out in a solvent including, for instance, ethers such as diethyl ether, isopropyl ether, dioxane, tetrahydrofuran (THF) and 1,2-dimethoxyethane, aromatic hydrocarbons such as benzene, toluene and xylene,

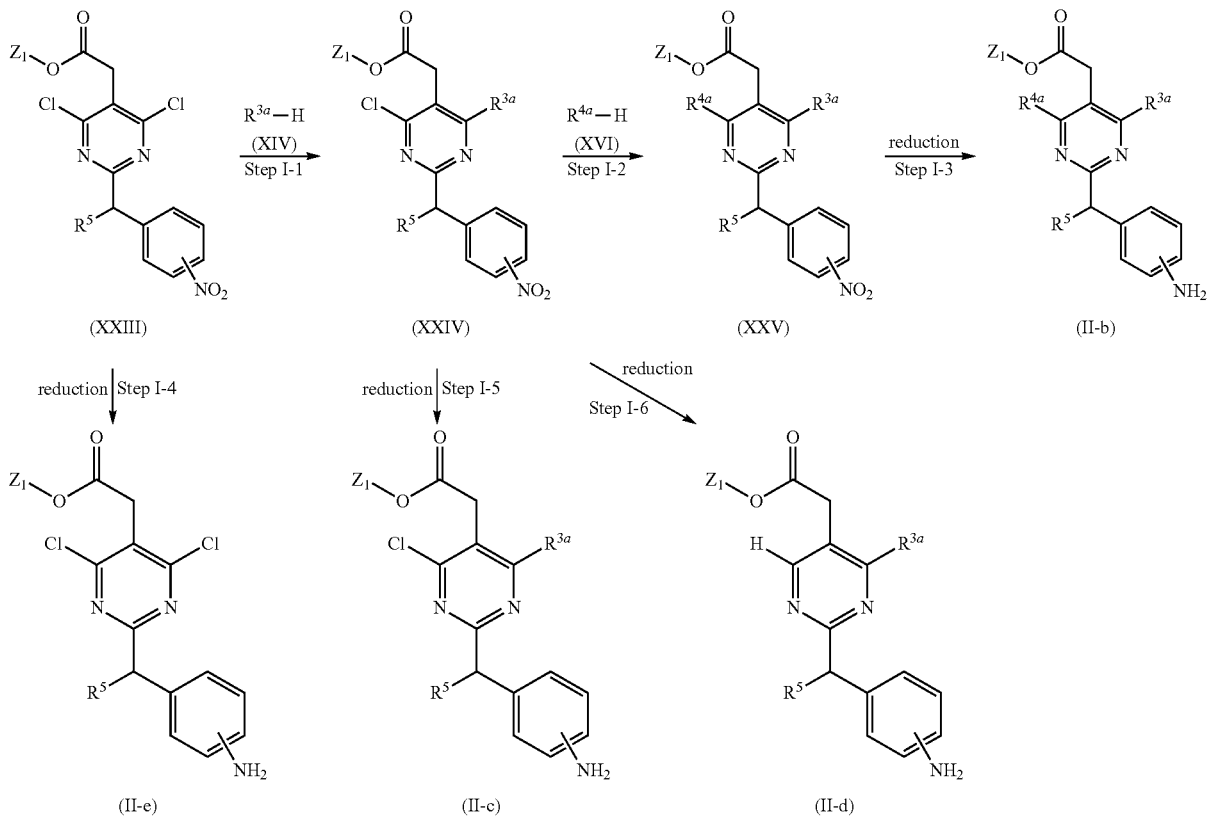

Compounds of the formula (II-b) (wherein $R^{3a}$, $R^{4a}$, $R^5$ and $Z_1$ are the same as defined above) can be, for instance, prepared by the following procedures.

In Step i-1, compounds of the formula (XXIV) (wherein $R^{3a}$, $R^5$ and $Z_1$ are the same as defined above) can be prepared by the reaction of compounds of the formula (XXIII) (wherein $R^5$ and $Z_1$ are the same as defined above) with compounds of the formula (XIV) (wherein $R^{3a}$ is the same as defined above) in a similar manner described in Step F-2 for the preparation of compounds of the formula (XV).

In Step i-2, compounds of the formula (XXV) (wherein $R^{3a}$, $R^{4a}$, $R^5$ and $Z_1$ are the same as defined above) can be prepared by the reaction of compounds of the formula (XXIV) (wherein $R^{3a}$, $R^5$ and $Z_1$ are the same as defined above) with compounds of the formula (XVI) (wherein $R^{4a}$ is alcohols such as methanol, ethanol, 1-propanol, isopropanol and tert-butanol, water and others.

The reaction temperature can be optionally set depending on the compounds to be reacted. The reaction temperature is usually, but not limited to, about 0° C. to 180° C. and preferably about 20° C. to 100° C. The reaction may be conducted for, usually, 30 minutes to 24 hours and preferably 1 hour to 12 hours.

In Step i-4, compounds of the formula (II-a) (wherein $R^5$ and $Z_1$ are the same as defined above) can be prepared by reducing the nitro group of compounds of the formula (XXIII) (wherein $R^5$ and $Z_1$ are the same as defined above) in a similar manner described in Step i-3 for the preparation of compounds of the formula (II-b).

In Step i-5, compounds of the formula (II-c) (wherein $R^{3a}$, $R^5$ and $Z_1$ are the same as defined above) can be prepared by reducing the nitro group of compounds of the formula (XXIV) (wherein $R^{3a}$, $R^5$ and $Z_1$ are the same as defined above) in a similar manner described in Step i-3 for the preparation of compounds of the formula (II-b).

In Step i-6, compounds of the formula (II-d) (wherein $R^{3a}$, $R^5$ and $Z_1$ are the same as defined above) can be prepared by reducing the nitro group and the chloro group of compounds of the formula (XXIV) (wherein $R^{3a}$, $R^5$ and $Z_1$ are the same as defined above) by hydrogenation using a catalyst including, for instance, palladium on carbon and platinum on carbon in the presence of a base such as potassium acetate.

The reaction can be carried out in a solvent including, for instance, ethers such as diethyl ether, isopropyl ether, dioxane, tetrahydrofuran (THF) and 1,2-dimethoxyethane, aromatic hydrocarbons such as benzene, toluene and xylene, alcohols such as methanol, ethanol, 1-propanol, isopropanol and tert-butanol, water and others.

The reaction temperature can be optionally set depending on the compounds to be reacted. The reaction temperature is usually, but not limited to, about 0° C. to 180° C. and preferably about 20° C. to 100° C. The reaction may be conducted for, usually, 30 minutes to 24 hours and preferably 1 hour to 12 hours.

Preparation of Compounds of the Formula (XXIII)

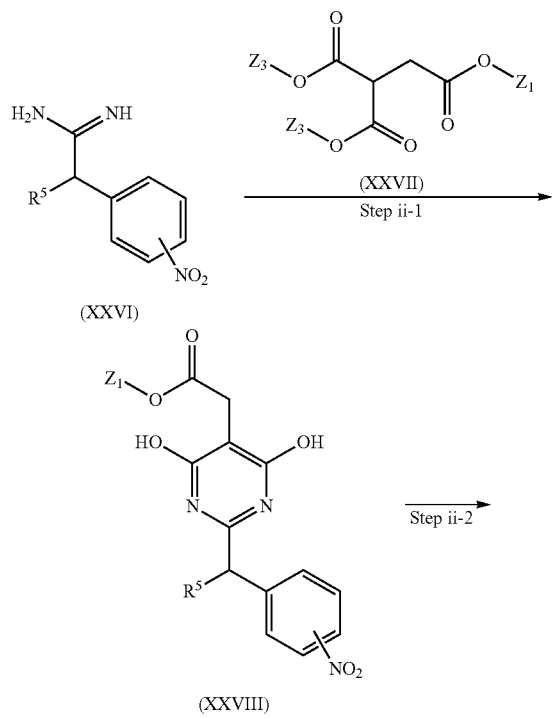

Compounds of the formula (XXIII) (wherein $R^5$ and $Z_1$ are the same as defined above) can be, for instance, prepared by the following procedures.

In Step ii-1, compounds of the formula (XXVIII) (wherein $R^5$ and $Z_1$ are the same as defined above) can be prepared by the reaction of compounds of the formula (XXVI) (wherein $R^5$ is the same as defined above) with compounds of the formula (XXVII) (wherein $Z_1$ is the same as defined above and $Z_3$ is $C_{1-6}$ alkyl)

The reaction can be advantageously carried out in the presence of a base such as sodium methoxide.

The reaction may be carried out in a solvent including, for instance, alcohols such as methanol, ethanol, 1-propanol, isopropanol and tert-butanol.

The reaction temperature can be optionally set depending on the compounds to be reacted. The reaction temperature is usually, but not limited to, about 0° C. to 180° C. and preferably about 20° C. to 100° C. The reaction may be conducted for, usually, 30 minutes to 24 hours and preferably 1 hour to 12 hours.

In Step ii-2, compounds of the formula (XXIII) (wherein $R^5$ and $Z_1$ are the same as defined above) can be prepared for instance, by the reaction of compounds of the formula (XXVIII) (wherein $R^5$ and $Z_1$ are the same as defined above) with an appropriate halogenating reagent including, for instance, $POCl_3$, $PCl_5$, and the like.

The reaction may be carried out without solvent or in a solvent including, for instance, halogenated hydrocarbons such as dichloromethane, chloroform and 1,2-dichloroethane, aromatic hydrocarbons such as benzene, toluene, and xylene, and others. Optionally, two or more of the solvents selected from the listed above can be mixed and used.

The reaction can be advantageously conducted in the presence of a base, including, for instance, pyridine, triethylamine and N,N-diisopropylethylamine, N,N-dimethylaniline, diethylaniline, and others.

The reaction temperature is usually, but not limited to, about 40° C. to 200° C. and preferably about 20° C. to 180° C. The reaction may be conducted for, usually, 30 minutes to 48 hours and preferably 2 hour to 12 hours.

Compounds of the formula (XXVI) and (XXVII) are commercially available or can be synthesized by conventional methods.

Preparation of Compounds of the Formula (II-e)

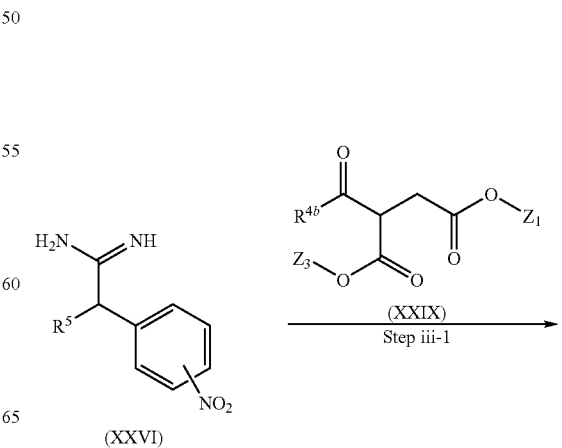

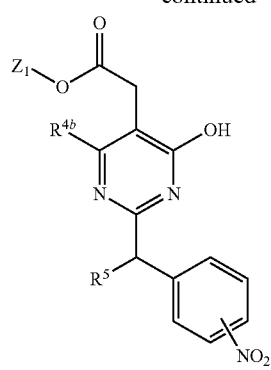
(XXX)

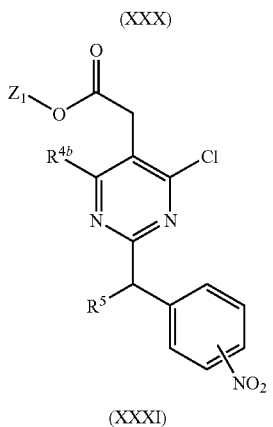
(XXXI)

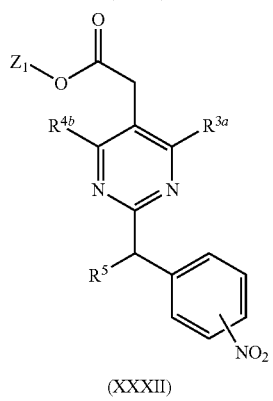
(XXXII)

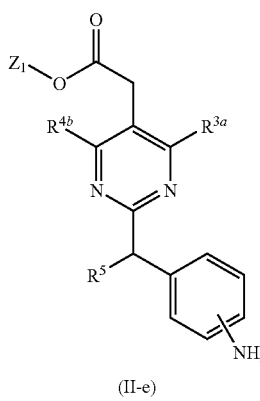
(II-e)

Compounds of the formula (II-e) (wherein $R^{3a}$, $R^5$ and $Z_1$ are the same as defined above and $R^{4b}$ is $C_{1-6}$ alkyl optionally substituted by mono-, di-, or tri-halogen) can be, for instance, prepared by the following procedures.

In Step iii-1, compounds of the formula (XXX) (wherein $R^{4b}$, $R^5$ and $Z_1$ are the same as defined above) can be prepared by the reaction of compounds of the formula (XXVI) (wherein $R^5$ is the same as defined above) and compounds of the formula (XXIX) (wherein $R^{4b}$, $Z_1$ and $Z_3$ are the same as defined above) in a similar manner described in Step ii-1 for the preparation of compounds of the formula (XXVIII).

In Step iii-2, compounds of the formula (XXXI) (wherein $R^{4b}$, $R^5$ and $Z_1$ are the same as defined above) can be prepared by the reaction of compounds of the formula (XXX) (wherein $R^{4b}$, $R^5$ and $Z_1$ are the same as defined above) with an appropriate halogenating reagent in a similar manner described in Step ii-2 for the preparation of compounds of the formula (XXIII).

In Step iii-3, compounds of the formula (XXXII) (wherein $R^{3a}$, $R^{4b}$, $R^5$ and $Z_1$ are the same as defined above) can be prepared by the reaction of compounds of the formula (XXXI) (wherein $R^{4b}$, $R^5$ and $Z_1$ are the same as defined above) with compounds of the formula (XIV) (wherein $R^{3a}$ is the same as defined above) in a similar manner described in Step F-2 for the preparation of compounds of the formula (XV).

In Step iii-4, compounds of the formula (II-e) (wherein $R^{3a}$, $R^{4b}$, $R^5$ and $Z_1$ are the same as defined above) can be prepared by reducing the nitro group of compounds of the formula (XXXII) (wherein $R^{3a}$, $R^{4b}$, $R^5$ and $Z_1$ are the same as defined above) in a similar manner described in Step i-3 for the preparation of compounds of the formula (II-b).

Compounds of the formula (XXIX) are commercially available or can be synthesized by conventional methods.

[Method J]

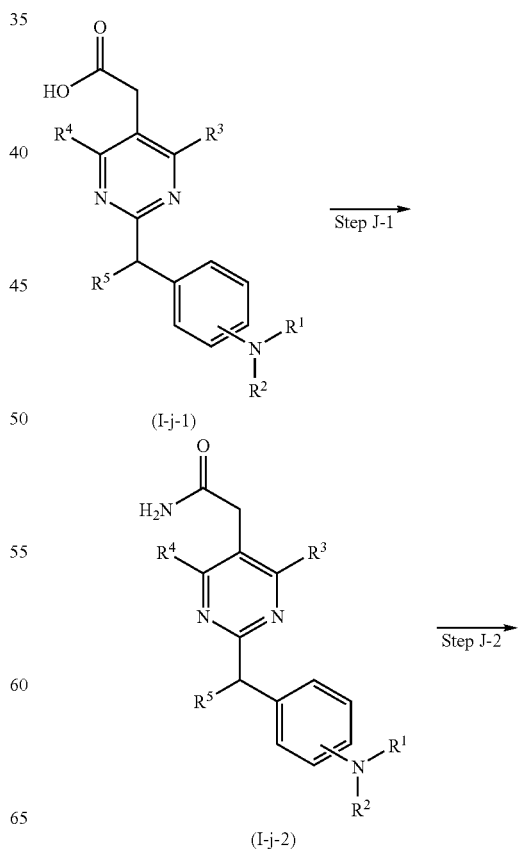
(I-j-1)

(I-j-2)

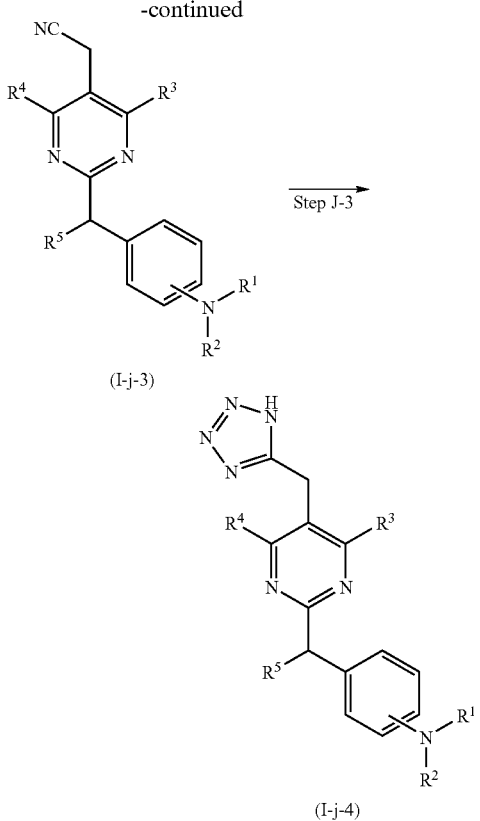

Compounds of the formula (I-j-2), (I-j-3) and (I-j-4) can be prepared by the following procedures.

In Step J-1, compounds of the formula (I-j-2)(wherein $R^1$, $R^2$, $R^3$, $R^4$ and $R^5$ are the same as defined above) can be prepared by the reaction of compounds of the formula (I-j-1) (wherein $R^1$, $R^2$, $R^3$, $R^4$ and $R^5$ are the same as defined above) with ammonia.

The reaction may be carried out using a agent including, for instance, aryl formate derivative such as phenyl chloroformate; halogenating agent such as $SOCl_2$ and $POCl_3$; carbonyldiazole derivative such as 1,1-carbonyldiimidazole (CDI), and 1,1'-carbonyldi(1,2,4-triazole)(CDT), and the like to activate the carboxy group of the compounds of the formula (I-j-1).

The reaction may be carried out in a solvent including, for instance, halogenated hydrocarbons such as dichloromethane, chloroform and 1,2-dichloroethane; ethers such as diethyl ether, isopropyl ether, dioxane and tetrahydrofuran (THF) and 1,2-dimethoxyethane; aromatic hydrocarbons such as benzene, toluene and xylene; nitrites such as acetonitrile; amides such as N, N-dimethylformamide (DMF), N,N-dimethylacetamide (DMAC) and N-methylpyrrolidone (NMP); urea such as 1,3-dimethyl-2-imidazolidinone (DMI); and others. Optionally, two or more of the solvents selected from the listed above can be mixed and used.

The reaction temperature can be optionally set depending on the compounds to be reacted. The reaction temperature is usually, but not limited to, about 0° C. to 180° C. and preferably about 20° C. to 100° C. The reaction may be conducted for, usually, 30 minutes to 24 hours and preferably 1 hour to 12 hours.

In Step J-2, compounds of the formula (I-j-3) (wherein $R^1$, $R^2$, $R^3$, $R^4$ and $R^5$ are the same as defined above) can be prepared by the reaction of compounds of the formula (I-j-2) (wherein $R^1$, $R^2$, $R^3$, $R^4$ and $R^5$ are the same as defined above) using an agent including, for instance, trifluoroacetic anhydride.

The reaction may be carried out without solvent or in a solvent including, for instance, halogenated hydrocarbons such as dichloromethane, chloroform and 1,2-dichloroethane; ethers such as diethyl ether, isopropyl ether, dioxane and tetrahydrofuran (THF) and 1,2-dimethoxyethane; aromatic hydrocarbons such as benzene, toluene and xylene; and others. Optionally, two or more of the solvents selected from the listed above can be mixed and used.

The reaction temperature can be optionally set depending on the compounds to be reacted. The reaction temperature is usually, but not limited to, about 0° C. to 180° C. and preferably about 20° C. to 100° C. The reaction may be conducted for, usually, 30 minutes to 48 hours and preferably 1 hour to 24 hours.

In Step J-3, compounds of the formula (I-j-4) (wherein $R^1$, $R^2$, $R^3$, $R^4$ and $R^5$ are the same as defined above) can be prepared by the reaction of compounds of the formula (I-j-3) (wherein $R^1$, $R^2$, $R^3$, $R^4$ and $R^5$ are the same as defined above) with an agent including, for instance, sodium azide.

The reaction can be advantageously conducted in the presence of a catalyst, including, for instance, zinc dibromide, and others.

The reaction may be carried out in a solvent including, for instance, halogenated hydrocarbons such as dichloromethane, chloroform and 1,2-dichloroethane; ethers such as diethyl ether, isopropyl ether, dioxane and tetrahydrofuran (THF) and 1,2-dimethoxyethane; aromatic hydrocarbons such as benzene, toluene and xylene; alcohols such as methanol, ethanol, 1-propanol, isopropanol and tert-butanol, water and others. Optionally, two or more of the solvents selected from the listed above can be mixed and used.

The reaction temperature can be optionally set depending on the compounds to be reacted. The reaction temperature is usually, but not limited to, about 0° C. to 180° C. and preferably about 20° C. to 100° C. The reaction may be conducted for, usually, 30 minutes to 48 hours and preferably 1 hour to 24 hours.

Compounds of the formula (I-j-1) can be synthesized by the Method [A], [B], [C], [D], [E], [F], [G], [H] or [I] described above.

Typical salts of the compound shown by the formula (I) include salts prepared by reaction of the compounds of the present invention with a mineral or organic acid, or an organic or inorganic base. Such salts are known as acid addition and base addition salts, respectively.

Acids to form acid addition salts include inorganic acids such as, without limitation, sulfuric acid, phosphoric acid, hydrochloric acid, hydrobromic acid, hydriodic acid and the like, and organic acids, such as, without limitation, p-toluenesulfonic acid, methanesulfonic acid, oxalic acid, p-bromophenylsulfonic acid, carbonic acid, succinic acid, citric acid, benzoic acid, acetic acid, and the like.

Base addition salts include those derived from inorganic bases, such as, without limitation, ammonium hydroxide, alkaline metal hydroxide, alkaline earth metal hydroxides, carbonates, bicarbonates, and the like, and organic bases, such as, without limitation, ethanolamine, triethylamine, tris(hydroxymethyl)aminomethane, and the like. Examples of inorganic bases include, sodium hydroxide, potassium hydroxide, potassium carbonate, sodium carbonate, sodium bicarbonate, potassium bicarbonate, calcium hydroxide, calcium carbonate, and the like.

The compound of the present invention or salts thereof, depending on its substituents, may be modified to form lower alkylesters or known other esters; and/or hydrates or other solvates. Those esters, hydrates, and solvates are included in the scope of the present invention.

The compounds of the present invention can also be used in the form of prodrugs which include esters. Examples of such esters useful as prodrugs for compounds containing carboxyl groups can be found on pages 14-21 of "Bioreversible Carriers in Drug Design: Theory and Application", edited by E. B. Roche, Pergamon Press, New York (1987). Representative carboxy protecting groups are C 1 to C 8 alkyl (e.g., methyl, ethyl or tertiary butyl and the like); haloalkyl; alkenyl; cycloalkylalkyl and substituted derivatives thereof such as cyclohexylmethyl, cylcopentylmethyl and the like; arylalkyl, for example, phenethyl or benzyl and substituted derivatives thereof such as alkoxybenzyl groups and the like; arylalkenyl, for example, phenylethenyl and the like; aryl and substituted derivatives thereof, for example, 5-indanyl and the like; dialkylaminoalkyl (e.g., dimethylaminoethyl and the like); alkanoyloxyallyl groups such as acetoxymethyl, butyryloxymethyl, valeryloxymethyl, isobutyryloxymethyl, isovaleryloxymethyl, 1-(propionyloxy)-1-ethyl, 1-(pivaloyloxyl)-1-ethyl, 1-methyl-1-(propionyloxy)-1-ethyl, pivaloyloxymethyl, propionyloxymethyl and the like; cycloalkanoyloxyalkyl groups such as cyclopropylcarbonyloxymethyl, cyclobutylcarbonyloxymethyl, cyclopentylcarbonyloxymethyl, cyclohexylcarbonyloxymethyl and the like; aroyloxyalkyl, such as benzoyloxymethyl, benzoyloxyethyl and the like; arylalkyl-carbonyloxyalkyl, such as benzylcarbonyloxymethyl, 2-benzylcarbonyloxyethyl and the like; alkoxycarbonylalkyl, such as methoxycarbonylmethyl, cyclohexyloxycarbonylmethyl, 1-methoxycarbonyl-1-ethyl, and the like; alkoxycarbonyloxyalkyl, such as methoxycarbonyloxymethyl, t-butyloxycarbonyloxymethyl, 1-ethoxycarbonyloxy-1-ethyl, 1-cyclohexyloxycarbonyloxy-1-ethyl and the like; alkoxycarbonylaminoalkyl, such as t-butyloxycarbonylaminomethyl and the like; alkylaminocarbonylaminoalkyl, such as methylaminocarbonylaminomethyl and the like; alkanoylaminoalkyl, such as acetylaminomethyl and the like; heterocycliccarbonyloxyalkyl, such as 4-methylpiperazinylcarbonyloxymethyl and the like; dialkylaminocarbonylalkyl, such as dimethylaminocarbonylmethyl, diethylaminocarbonylmethyl and the like; (5-(lowerallyl)-2-oxo-1,3-dioxolen-4-yl)alkyl, such as (5-t-butyl-2-oxo-1,3-dioxolen-4-yl)methyl and the like; and (5-phenyl-2-oxo-1,3-dioxolen-4-yl)alkyl, such as (5-phenyl-2-oxo-1,3-dioxolen-4-yl)methyl and the like.

The compound of the present invention may be administered in oral forms, such as, without limitation, normal and enteric coated tablets, capsules, pills, powders, granules, elixirs, tinctures, solution, suspensions, syrups, solid and liquid aerosols and emulsions. They may also be administered in parenteral forms, such as, without limitation, intravenous, intraperitoneal, subcutaneous, intramuscular, and the like forms, well-known to those of ordinary skill in the pharmaceutical arts. The compounds of the present invention can be administered in intranasal form via topical use of suitable intranasal vehicles, or via transdermal routes, using transdermal delivery systems well-known to those of ordinary skilled in the art.

The dosage regimen with the use of the compounds of the present invention is selected by one of ordinary skill in the arts, in view of a variety of factors, including, without limitation, age, weight, sex, and medical condition of the recipient, the severity of the condition to be treated, the route of administration, the level of metabolic and excretory function of the recipient, the dosage form employed, the particular compound and salt thereof employed.

The compounds of the present invention are preferably formulated prior to administration together with one or more pharmaceutically-acceptable excipients. Excipients are inert substances such as, without limitation, carriers, diluents, flavoring agents, sweeteners, lubricants, solubilizers, suspending agents, binders, tablet disintegrating agents and encapsulating material.

Yet another embodiment of the present invention is a pharmaceutical formulation comprising a compound of the invention and one or more pharmaceutically-acceptable excipients that are compatible with the other ingredients of the formulation and not deleterious to the recipient thereof. Pharmaceutical formulations of the invention are prepared by combining a therapeutically effective amount of the compounds of the invention together with one or more pharmaceutically-acceptable excipients therefore. In making the compositions of the present invention, the active ingredient may be mixed with a diluent, or enclosed within a carrier, which may be in the form of a capsule, sachet, paper, or other container. The carrier may serve as a diluent, which may be solid, semi-solid, or liquid material which acts as a vehicle, or can be in the form of tablets, pills, powders, lozenges, elixirs, suspensions, emulsions, solutions, syrups, aerosols, ointments, containing, for example, up to 10% by weight of the active compound, soft and hard gelatin capsules, suppositories, sterile injectable solutions and sterile packaged powders.

For oral administration, the active ingredient may be combined with an oral, and non-toxic, pharmaceutically-acceptable carrier, such as, without limitation, lactose, starch, sucrose, glucose, sodium carbonate, mannitol, sorbitol, calcium carbonate, calcium phosphate, calcium sulfate, methyl cellulose, and the like; together with, optionally, disintegrating agents, such as, without limitation, maize, starch, methyl cellulose, agar bentonite, xanthan gum, alginic acid, and the like; and optionally, binding agents, for example, without limitation, gelatin, natural sugars, beta-lactose, corn sweeteners, natural and synthetic gums, acacia, tragacanth, sodium alginate, carboxymethylcellulose, polyethylene glycol, waxes, and the like; and, optionally, lubricating agents, for example, without limitation, magnesium stearate, sodium stearate, stearic acid, sodium oleate, sodium benzoate, sodium acetate, sodium chloride, talc, and the like.

In powder forms, the carrier may be a finely divided solid which is in admixture with the finely divided active ingredient. The active ingredient may be mixed with a carrier having binding properties in suitable proportions and compacted in the shape and size desired to produce tablets. The powders and tablets preferably contain from about 1 to about 99 weight percent of the active ingredient which is the novel composition of the present invention. Suitable solid carriers are magnesium carboxymethyl cellulose, tow melting waxes, and cocoa butter.

Sterile liquid formulations include suspensions, emulsions, syrups and elixirs. The active ingredient can be dissolved or suspended in a pharmaceutically acceptable carrier, such as sterile water, sterile organic solvent, or a mixture of both sterile water and sterile organic solvent.

The active ingredient can also be dissolved in a suitable organic solvent, for example, aqueous propylene glycol. Other compositions can be made by dispersing the finely divided active ingredient in aqueous starch or sodium carboxymethyl cellulose solution or in a suitable oil.

The formulation may be in unit dosage form, which is a physically discrete unit containing a unit dose, suitable for administration in human or other mammals. A unit dosage form can be a capsule or tablets, or a number of capsules or tablets. A "unit dose" is a predetermined quantity of the active compound of the present invention, calculated to produce the desired therapeutic effect, in association with one or more excipients. The quantity of active ingredient in a unit dose may be varied or adjusted from about 0.1 to about 1000 milligrams or more according to the particular treatment involved.

Typical oral dosages of the compound of the present invention, when used for the indicated effects, will range from about 1 mg/kg/day to about 10 mg/kg/day. The compounds of the present invention may be administered in a single daily dose, or the total daily dose may be administered in divided doses, two, three, or more times per day. Where delivery is via transdermal forms, of course, administration is continuous.

EXAMPLES

The present invention will be described as a form of examples, but they should by no means be construed as defining the metes and bounds of the present invention.

In the examples below, all quantitative data, if not stated otherwise, relate to percentages by weight.

Mass spectra were obtained using electrospray (ES) ionization techniques (micromass Platform LC). Melting points are uncorrected. Liquid Chromatography-Mass spectroscopy (LC-MS) data were recorded on a Micromass Platform LC with Shimadzu Phenomenex ODS column (4.6 mm$\phi$×30 mm) flushing a mixture of acetonitrile-water (9:1 to 1:9) at 1 ml/min of the flow rate. TLC was performed on a precoated silica gel plate (Merck silica gel 60 F-254). Silica gel (WAKO-gel C-200 (75-150 μm)) was used for all column chromatography separations. All chemicals were reagent grade and were purchased from Sigma-Aldrich, Wako pure chemical industries, Ltd., Great Britain, Tokyo kasei kogyo Co., Ltd., Nacalai tesque, Inc., Watanabe Chemical Ind. Ltd., Maybridge plc, Lancaster Synthesis Ltd., Merck KgaA, Germany, Kanto Chemical Co., Ltd.

$^1$H NMR spectra were recorded using either Bruker DRX-300 (300 MHz for $^1$H) spectrometer or Brucker 500 UltraShieled™ (500 MHz for 1H). Chemical shifts are reported in parts per million (ppm) with tetramethylsilane (TMS) as an internal standard at zero ppm. Coupling constant (J) are given in hertz and the abbreviations s, d, t, q, m, and br refer to singlet, doblet, triplet, quartet, multiplet, and broad, respectively. The mass determinations were carried out by MAT95 (Finnigan MAT).

All starting materials are commercially available or can be prepared using methods cited in the literature.

The effect of the present compounds was examined by the following assays and pharmacological tests.

Example 1

Preparation of Human CRTH2-Transfected L1.2 Cell Line

Human CRTH2 cDNA was amplified from human eosinophil cDNA with gene specific primers containing restriction sites for cloning into pEAK vector (Edge Bio Systems). The human CRTH2 cDNA was cloned into the mammalian expression vector pEAK. This expression plasmid (40 μg) was transfected into L1.2 cells, at a cell density of 1×10$^7$ cells/500 μl, by using electroporation apparatus (Gene Pulser II, BioRad) at 250V/1,000 μF. One day after the transfection, puromycin (1 μg/ml, Sigma) was added into the cell culture plates. Two weeks after the transfection, grown cells were picked up for further growth.

[Measurement of Ca$^{2+}$ Mobilization in the Human CRTH2-Transfected L1.2 Cell Line] (Assay 1)

Ca$^{2+}$ loading buffer was prepared by mixing 5 μl of Fluo-3AM (2 mM in DMSO, final 1 μM, Molecular Probes) and 10 μl of pluronic F-127 (Molecular Probes) and diluting the resulting mixture in 10 ml of Ca$^{2+}$ assay buffer (20 mM HEPES pH 7.6, 0.1% BSA, 1 mM probenecid, Hanks' solution). The CRTH2 transfected cells which were prepared in Example 1 were washed with PBS, resuspended in Ca$^{2+}$ loading buffer at 1×10$^7$ cells/ml, and incubated for 60 min at room temperature. After incubation, cells were washed and resuspended in Ca$^{2+}$ assay buffer, then dispensed into transparent-bottom 96-well plates (#3631, Costar) at 2×10$^5$ cells/well. Cells were incubated with various concentrations of test compound for 5 minutes at room temperature. The emitted 480 nm fluorescence was measured on FDSS6000, a Ca$^{2+}$-measurement apparatus (Hamamatsu Photonics, Hamamatsu, Japan). The transfectant showed PGD$_2$-induced Ca$^{2+}$ mobilization in a concentration-dependent manner.

[Human CRTH2 Receptor Binding Assay] (Assay 2)

CRTH2 transfectants were washed once with PBS and resuspended in binding buffer (50 mM Tris-HCl, pH7.4, 40 mM MgCl$_2$, 0.1% BSA, 0.1% NaN$_3$). 100 μl of cell suspension (2×10$^5$ cells), [$^3$H]-labeled PGD$_2$, and various concentrations of test compound were then mixed in a 96-well U-bottom polypropylene plate and incubated for 60 mM at room temperature to allow binding to occur. After incubation, the cell suspension was transferred to a filtration plate (#MAFB, Millipore) and washed 3 times with binding buffer. Scintillant was added to the filtration plate, and radioactivity remaining on the filter was measured by TopCount (Packard), a scintillation counter. Non-specific binding was determined by incubating the cell suspension and [$^3$H]-labeled PGD$_2$ in the presence of 1 μM of unlabeled PGD$_2$. Puromycin-resistant L1.2 transfectants bound to [$^3$H]-labeled PGD$_2$ with high affinity (K$_D$=6.3 nM).

[Migration Assay of Human Eosinophils] (Assay 3)

Human polymorphonuclear cells were isolated from heparinized venous blood of healthy donors by laying the blood on Mono-Poly Resolving Medium (ICN Biomedicals, Co. Ltd) and centrifuging it at 400×g for 30 min. at room temperature. After centrifugation, eosinophils were purified from the lower layer of polymorphonuclear cells by CD16-negative selection using anti-CD16-conjugated magnetic beads (Miltenyi Biotech GmbH).

Human eosinophils were washed with PBS and resuspended in chemotaxis buffer (20 mM HEPES pH 7.6, 0.1% BSA, Hanks' solution) at 6×10$^6$ cells/ml. Fifty μl of the cell suspension (3×10$^5$ cells/well) was then dispensed into the upper chamber and 30 μl of ligand solution (PGD$_2$, 1 nM, final concentration) was added to the lower chamber of a 96-well chemotaxis chamber (Diameter=5 μm, #106-5, Neuro Probe). Cells were preincubated with various concentrations of test compound at 37° C. for 10 minutes. Chemotaxis is then allowed to occur in a humidified incubator at 37° C., 5% CO$_2$ for 2 hours. The number of cells migrating into the lower chamber was counted by FACScan (Becton-Dickinson).

[Migration Assay of Human CD4+ T Cells] (Assay 4)

Human mononuclear cells were isolated from heparinized venous blood of healthy donors by laying the blood on Mono-Poly Resolving Medium (ICN Biomedicals, Co. Ltd) and centrifuging it at 400×g for 30 minutes at room temperature. After centrifugation, CD4$^+$ T lymphocytes were purified from mononuclear cells by using CD4$^+$ T cell isolation kit (Miltenyi Biotec GmbH).

Human CD4$^+$ T lymphocytes were washed with PBS and resuspended in chemotaxis buffer (20 mM HEPES pH 7.6, 0.1% BSA, Hanks' solution) at 6×10$^6$ cells/ml. Fifty μl of the cell suspension (3×10$^5$ cells/well) was then dispensed into the upper chamber and 30 μl of ligand solution (PGD$_2$, 10 nM, final concentration) was added to the lower chamber of a 96-well chemotaxis chamber (Diameter=3 m, #106-3, Neuro Probe). Cells were preincubated with various concentrations of test compound at 37° C. for 10 minutes. Chemotaxis is then allowed to occur in a humidified incubator at 37° C., 5% CO$_2$ for 4 hours. The number of cells migrating into the lower chamber was counted by FACScan (Becton-Dickinson).

Assay results in Assay 1 are shown in Examples and tables of the Examples below. The data corresponds to the compounds as yielded by solid phase synthesis and thus to levels of purity of about 40 to 90%. For practical reasons, the compounds are grouped in four classes of activity as follows:

$IC_{50}=A(< or =)10 nM<B(< or =)100 nM<$
$C(< or =)500 nM<D$

The compounds of the present invention also show excellent selectivity, and potent activity in Assays 2, 3 and 4 described above.

z used in Melting point in the following section indicates decomposition. All inorganic acids and bases were aqueous solutions unless otherwise stated. Eluent concentrations are expressed as % vol./vol.

Preparation of Compounds

Methyl[4,6-dichloro-2-(4-nitrobenzyl)pyrimidin-5-yl]acetate

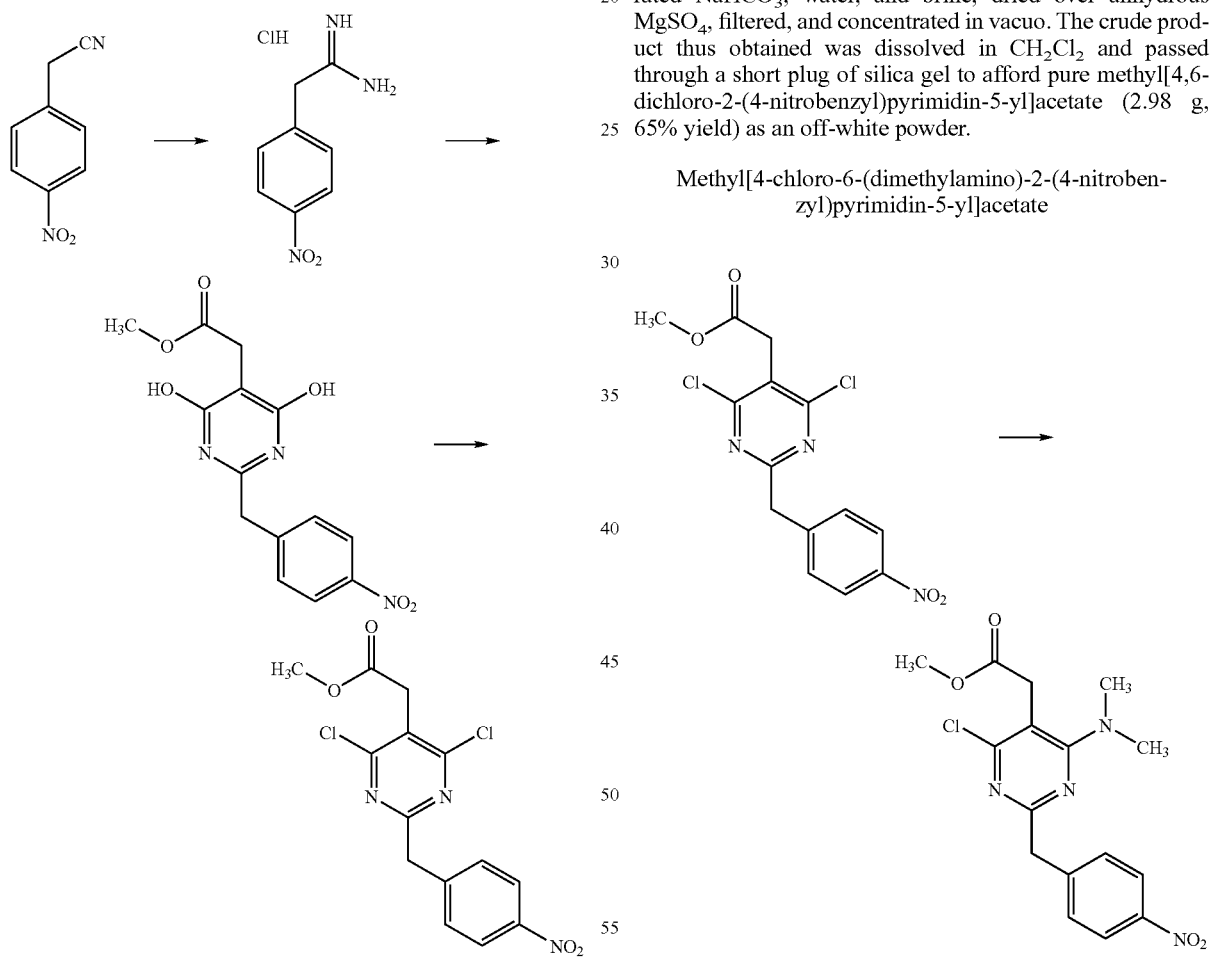

4-Nitrophenyl acetonitrile (81.07 g, 500 mmol) was suspended in EtOH (300 mL) and dioxane (300 mL) was added. After all solids had dissolved, dry HCl gas was bubbled through the reaction mixture for 1 hour and then stirred at room temperature for 15 hours. Et$_2$O was then added and the separated solids were collected by suction and rinsed with Et$_2$O. This intermediate was dissolved in NH$_3$ saturated EtOH and the solution thus obtained was stirred at room temperature for 14 hours. Excess solvent was removed in vacuo to give 2-(4-nitrophenyl)ethanimidamide hydrochloride (73.65 g, 68% yield) as a white powder.

To a mixture of triethyl 1,1,2-ethanetricarboxylate (3.51 mL, 15.30 mmol) and 2-(4-nitro-phenyl)ethanimidamide hydrochloride (46.95 g, 217.72 mmol) in anhydrous MeOH (300 mL) at room temperature was added NaOMe (3.8.82 g, 718.49 mmol) and the resulting suspension was refluxed for 16 h. After cooling to r.t., the reaction mixture was chilled to 0° C., acidified with 6N HCl, and the separated solids collected by suction and rinsed with cold water. Drying under high vacuum at 45° C. for 6 hours then gave methyl[4,6-dihydroxy-2-(4-nitrobenzyl)pyrimidin-5-yl]acetate (56.48 g, 81% yield) as a pale white powder.

To a suspension of methyl[4,6-dihydroxy-2-(4-nitrobenzyl)pyrimidin-5-yl]acetate (4.12 g, 12.89 mmol) in POCl$_3$ (24 mL) at room temperature and under Ar atmosphere was added N,N-dimethylaniline (8.17 mL, 64.44 mmol) and the resulting dark suspension was heated at reflux for 16 hours. After cooling to room temperature, excess POCl$_3$ was evaporated and the remaining dark residue was dissolved in EtOAc. This organic layer was then washed sequentially with saturated NaHCO$_3$, water, and brine, dried over anhydrous MgSO$_4$, filtered, and concentrated in vacuo. The crude product thus obtained was dissolved in CH$_2$Cl$_2$ and passed through a short plug of silica gel to afford pure methyl[4,6-dichloro-2-(4-nitrobenzyl)pyrimidin-5-yl]acetate (2.98 g, 65% yield) as an off-white powder.

Methyl[4-chloro-6-(dimethylamino)-2-(4-nitrobenzyl)pyrimidin-5-yl]acetate

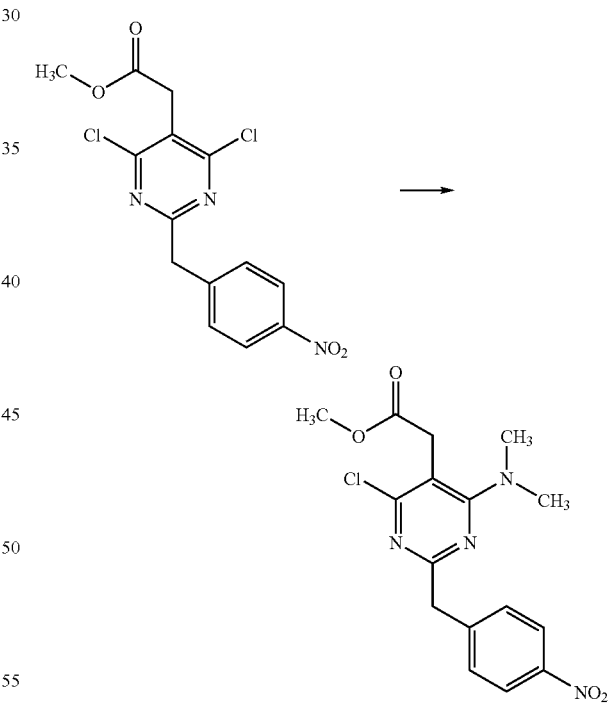

To a solution of methyl[4,6-dichloro-2-(4-nitrobenzyl)pyrimidin-5-yl]acetate (0.5 g, 1.40 mmol) in anhydrous DMF (5 mL) at room temperature under Ar atmosphere was added N,N-diisopropylethylamine (0.0.54 mL, 3.09 mmol) and dimethylamine hydrochloride (0.126 g, 1.54 mmol). The resulting solution was stirred at 85° C. for 16 hours at which time the reaction mixture was concentrated to dryness and the residue chromatographed over silica gel eluting with 50% EtOAc in n-hexane to give methyl[4-chloro-6-(dimethylamino)-2-(4-nitrobenzyl)pyrimidin-5-yl]acetate (0.505 g, 99% yield) as a brown oil.

Methyl[2-(4-aminobenzyl)-4-chloro-6-(dimethylamino)pyrimidin-5-yl]acetate

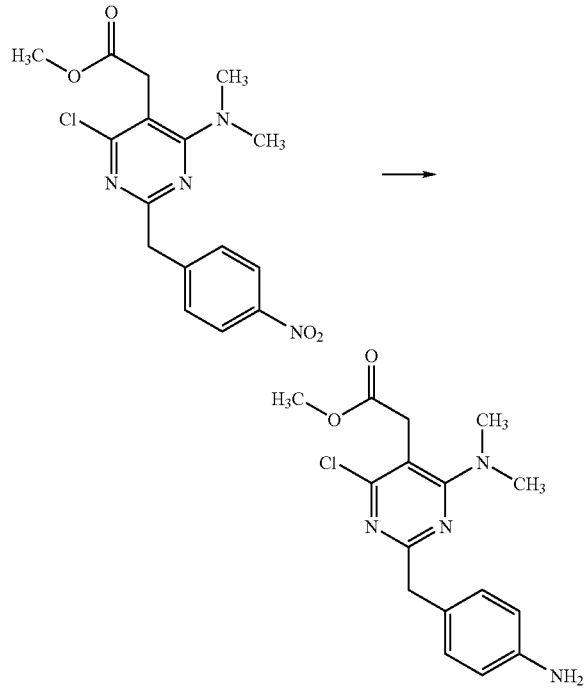

A solution of methyl[4-chloro-6-(dimethylamino)-2-(4-nitrobenzyl)pyrimidin-5-yl]acetate (1.00 g, 2.74 mmol) in anhydrous THF (20 mL) at room temperature was treated with 10% Pd/C (0.100 g) and the resulting black suspension was stirred under an atmosphere of hydrogen. After 13 hours, the reaction mixture was filtered over Celite. Evaporation of the filtrate gave the crude product as a clear oil which was passed through a short column eluting with 40% EtOAc in n-hexane to methyl[2-(4-aminobenzyl)-4-chloro-6-(dimethylamino)pyrimidin-5-yl]acetate (0.876 g, 95% yield) as a light orange oil which slowly solidified upon standing at room temperature.

Example 1-1

{4-chloro-6-(dimethylamino)-2-[4-(2-naphthoylamino)benzyl]pyrimidin-5-yl}acetic acid

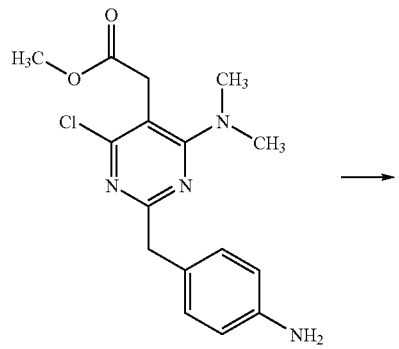

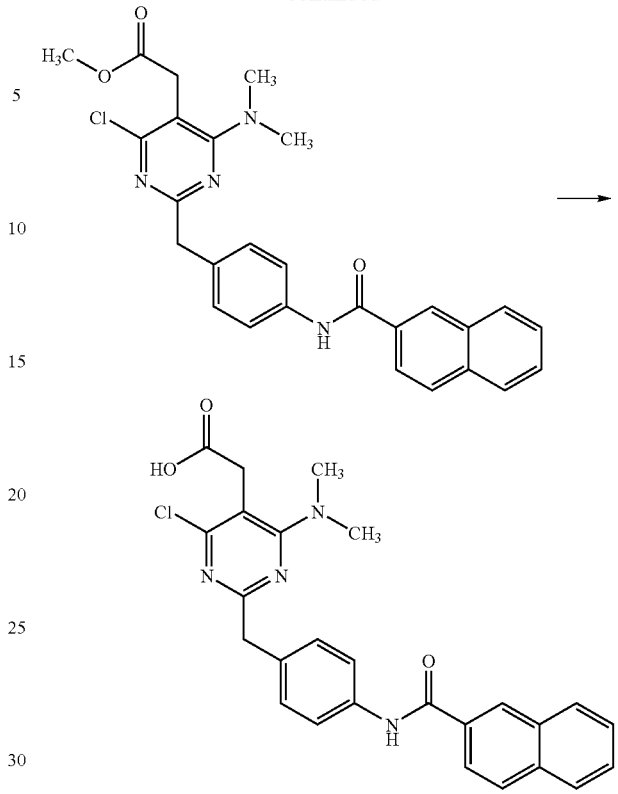

To a mixture of methyl[2-(4-aminobenzyl)-4-chloro-6-(dimethylamino)pyrimidin-5-yl]acetate (0.090 g, 0.30 mmol) and PyBOP (0.187 g, 0.36 mmol) in anhydrous DMF (1 mL) at room temperature was added 2-naphthoic acid (0.062 g, 0.36 mmol). The resulting reaction mixture was stirred at room temperature for 3 hours at which time water was added and the resulting aqueous phase was extracted with EtOAc. The combined organic extracts was sequentially washed with 0.5N HCl, saturated NaHCO$_3$, and brine, dried over anhydrous MgSO$_4$, filtered, and concentrated in vacuo to give methyl {4-chloro-6-(dimethylamino)-2-[4-(2-naphthoylamino)benzyl]pyrimidin-5-yl}acetate as a colorless oil.

The thus obtained methyl {4-chloro-6-(dimethylamino)-2-[4-(2-naphthoylamino)benzyl]pyrimidin-5-yl}acetate was dissolved in THF (1 mL) and treated with 1N NaOH (0.5 mL). The resulting biphasic mixture was stirred at room temperature for 14 hours at which time it was poured into water. The separated aqueous phase was washed with EtOAc and then acidified with 1N HCl and back extracted with EtOAc. The combined organic extracts was washed with brine, dried over anhydrous MgSO$_4$, filtered, and concentrated in vacuo. The crude product thus obtained was dissolved in a minimum volume of THF to which n-hexane was added. The separated precipitate was collected by suction, rinsed with n-hexane, and dried under vacuum to give {4-chloro-6-(dimethylamino)-2-[4-(2-naphthoylamino)benzyl]pyrimidin-5-yl}acetic acid (0.038 g, 40% yield) as a white powder.

$^1$H NMR (300 MHz, DMSO-d$_6$) δ: 3.05 (s, 6H), 3.67 (s, 2H), 3.93 (s, 2H), 7.32 (d, J=8 Hz, 2H), 7.59-7.68 (m, 2H), 7.75 (d, J=8 Hz, 2H), 8.00-8.10 (m, 4H), 8.57 (s, 1H), 10.40 (s, 1H), 12.77 (bs, 1H).
Molecular weight: 474.95
Mass spectrometry: 475
Melting point: 188 Z° C.
Activity class: A In a similar manner as described in Example 1-1, compounds in Example 1-2 to 1-68 as shown in Table 1 were synthesized.

TABLE 1

| Example # | Structure | MW | Exact Mass | MS | mp (° C.) | Activity class |
|---|---|---|---|---|---|---|
| 1-2 | 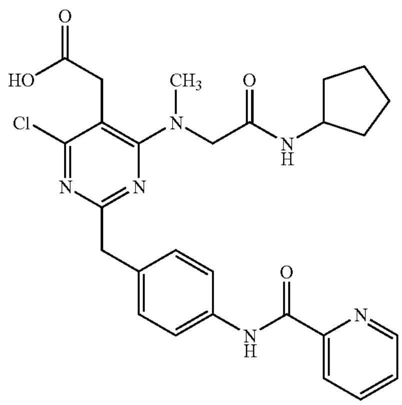 | 537.02 | 536 | 537 | >135 Z | D |
| 1-3 | 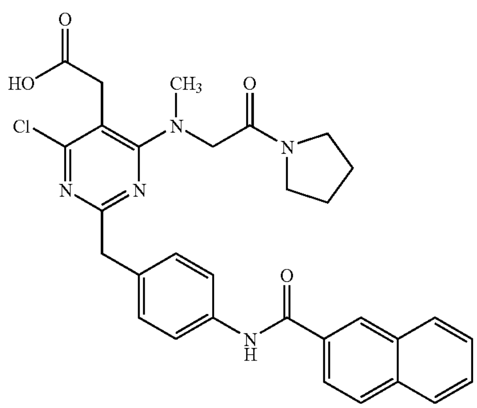 | 572.07 | 571 | 572 | 177 Z | A |
| 1-4 | 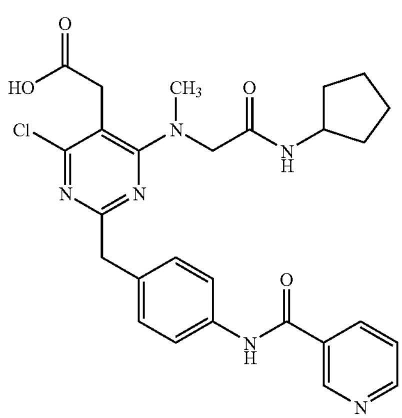 | 537.02 | 536 | 537 | >174 Z | D |

TABLE 1-continued

| Example # | Structure | MW | Exact Mass | MS | mp (° C.) | Activity class |
|---|---|---|---|---|---|---|
| 1-5 | 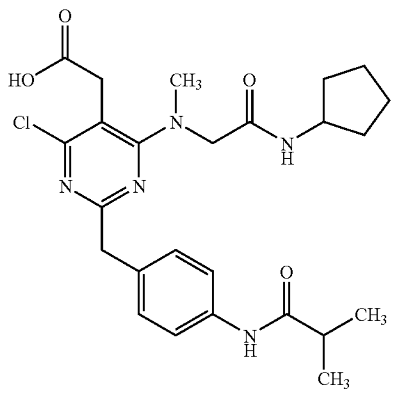 | 502.02 | 501 | 502 | >142 Z | D |
| 1-6 | 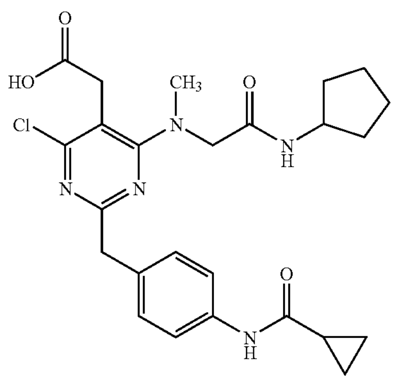 | 500.00 | 499 | 500 | >146 Z | D |
| 1-7 | 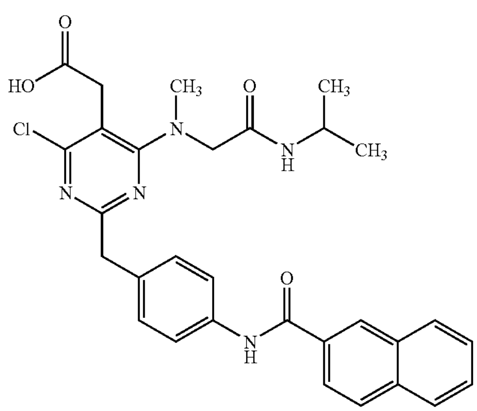 | 560.06 | 559 | 560 | 181 Z | A |
| 1-8 | 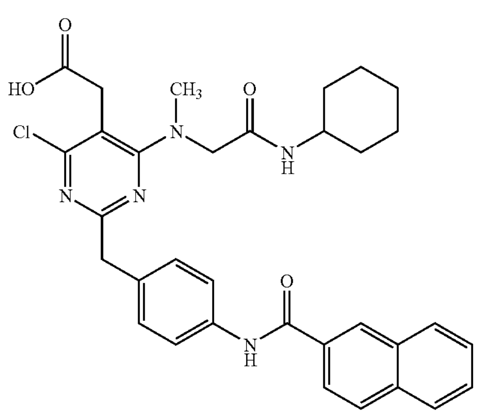 | 600.12 | 599 | 600 | 134 Z | A |

TABLE 1-continued

| Example # | Structure | MW | Exact Mass | MS | mp (° C.) | Activity class |
|---|---|---|---|---|---|---|
| 1-9 | 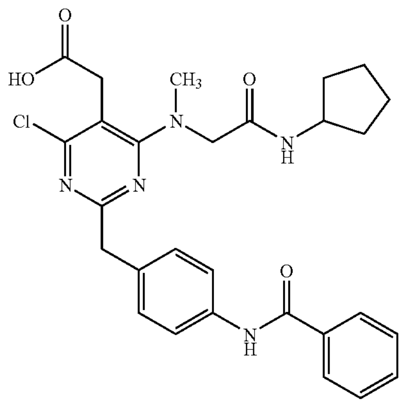 | 536.04 | 535 | 536 | >140 Z | B |
| 1-10 | 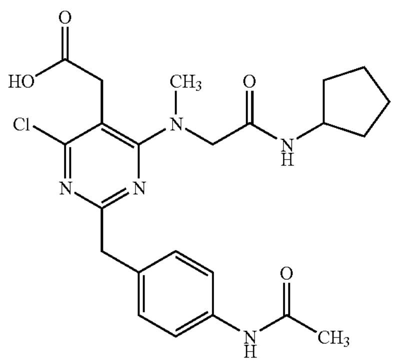 | 473.96 | 473 | 474 | >118 Z | D |
| 1-11 | 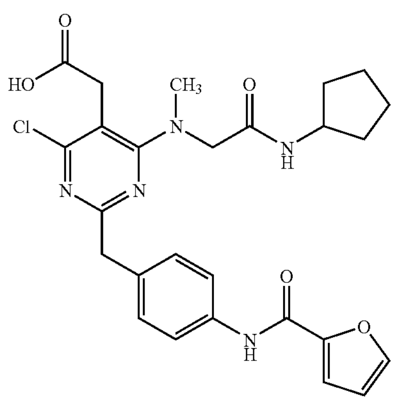 | 526.00 | 525 | 526 | >119 Z | C |
| 1-12 | 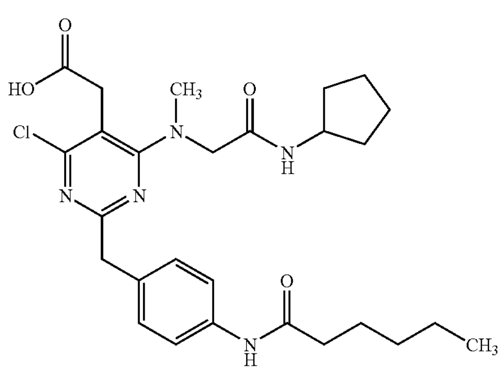 | 530.07 | 529 | 530 | >100 Z | C |

TABLE 1-continued

| Example # | Structure | MW | Exact Mass | MS | mp (° C.) | Activity class |
|---|---|---|---|---|---|---|
| 1-13 | 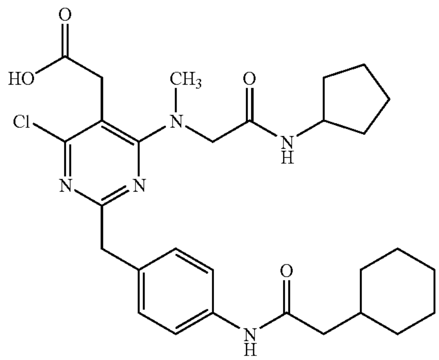 | 556.11 | 555 | 556 | >149 Z | B |
| 1-14 | 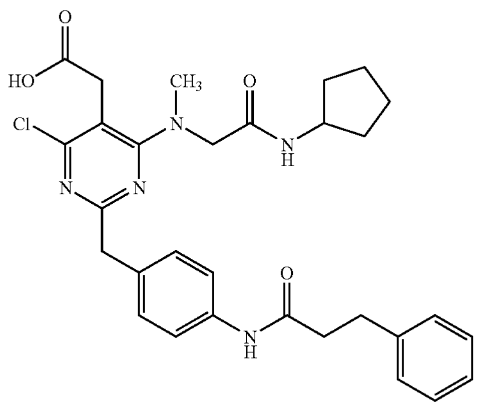 | 564.09 | 563 | 564 | >139 Z | A |
| 1-15 | 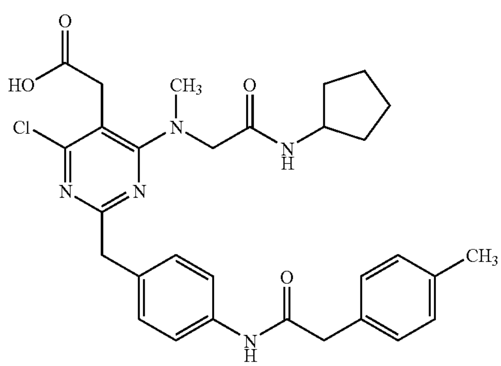 | 564.09 | 563 | 564 | >116 Z | B |
| 1-16 | 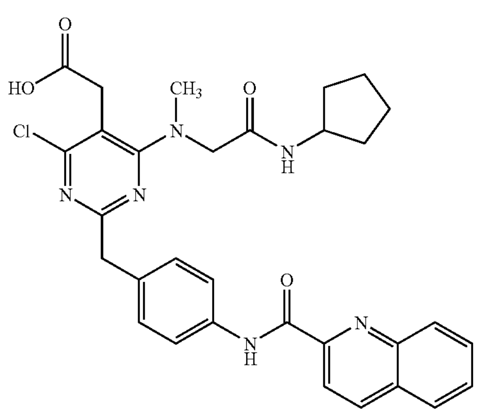 | 587.08 | 586 | 587 | 137 Z | A |

TABLE 1-continued

| Example # | Structure | MW | Exact Mass | MS | mp (° C.) | Activity class |
|---|---|---|---|---|---|---|
| 1-17 | 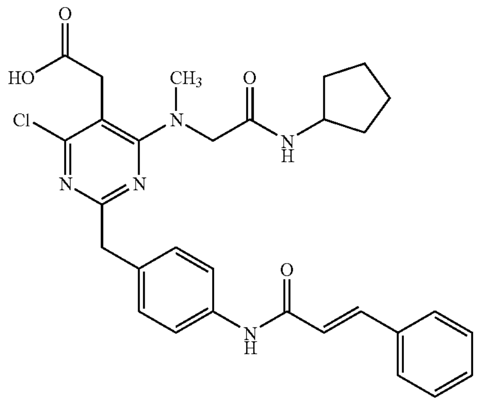 | 562.07 | 561 | 562 | 142 Z | A |
| 1-18 | 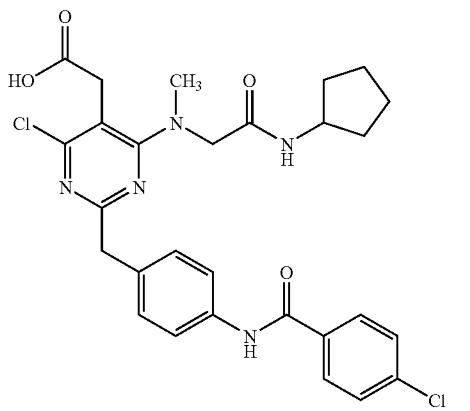 | 570.48 | 569 | 570 | 143 Z | A |
| 1-19 | 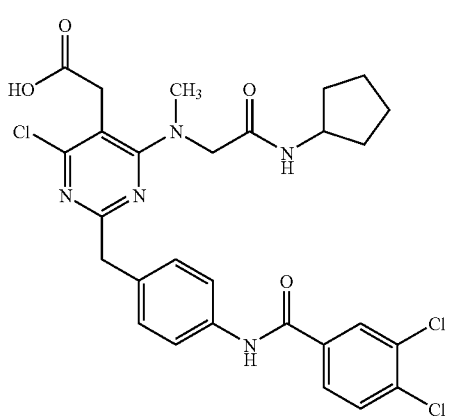 | 604.93 | 603 | 604 | 144 Z | A |

TABLE 1-continued

| Example # | Structure | MW | Exact Mass | MS | mp (° C.) | Activity class |
|---|---|---|---|---|---|---|
| 1-20 | 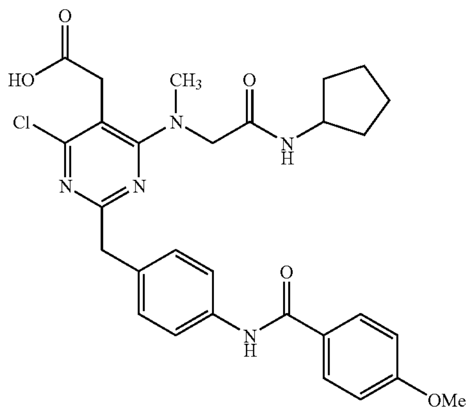 | 566.06 | 565 | 566 | 104 Z | A |
| 1-21 | 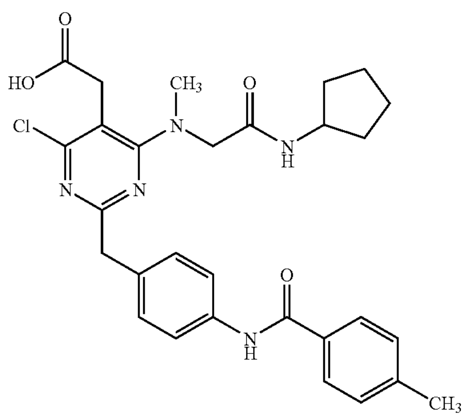 | 550.06 | 549 | 550 | 125 Z | A |
| 1-22 | 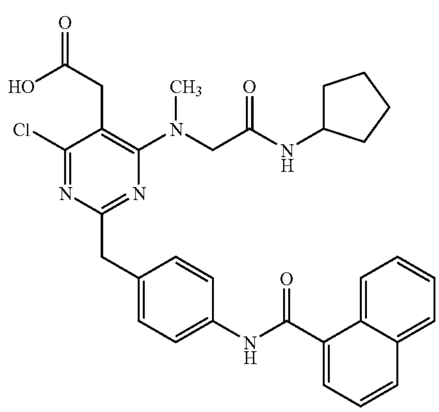 | 586.10 | 585 | 586 | 136 Z | B |
| 1-23 | 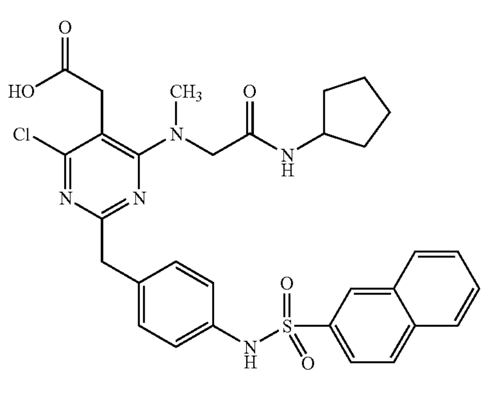 | 622.15 | 621.00 | 622.00 | 116 Z | D |

TABLE 1-continued

| Example # | Structure | MW | Exact Mass | MS | mp (° C.) | Activity class |
|---|---|---|---|---|---|---|
| 1-24 | 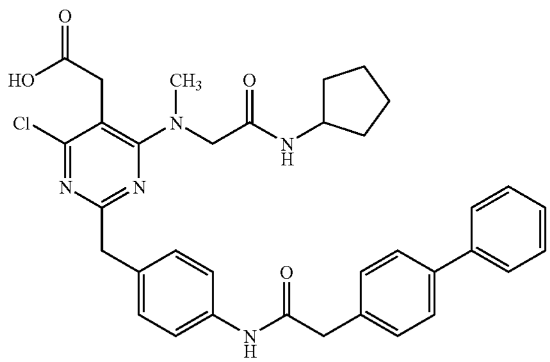 | 626.16 | 625.00 | 626.00 | 124 Z | C |
| 1-25 | 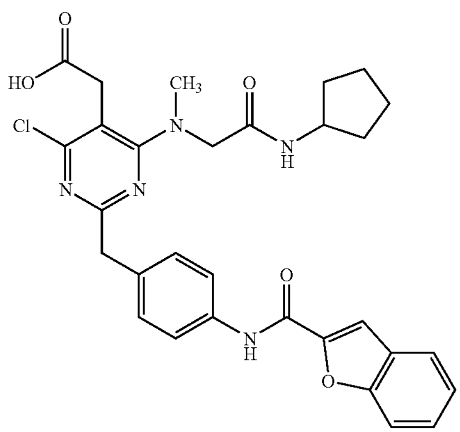 | 576.06 | 575 | 576 | 118 Z | A |
| 1-26 | 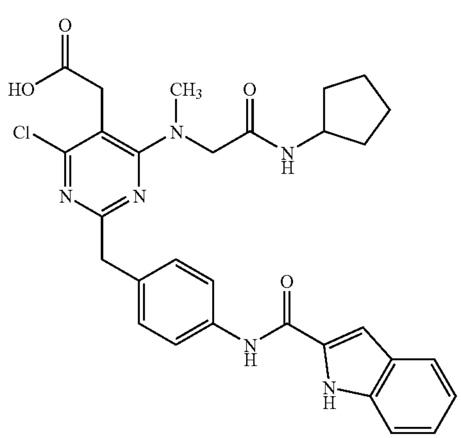 | 575.07 | 574 | 575 | 146 Z | A |

TABLE 1-continued

| Example # | Structure | MW | Exact Mass | MS | mp (° C.) | Activity class |
|---|---|---|---|---|---|---|
| 1-27 | 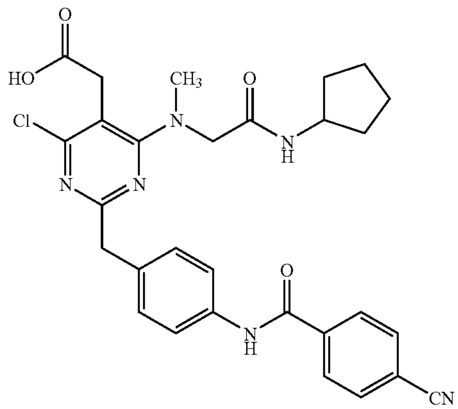 | 561.05 | 560.00 | 561.00 | 101 | A |
| 1-28 | 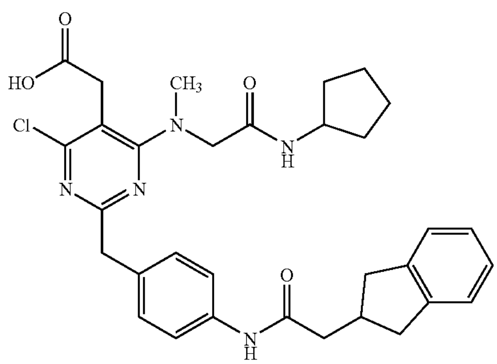 | 590.13 | 589 | 590 | >110 Z | A |
| 1-29 | 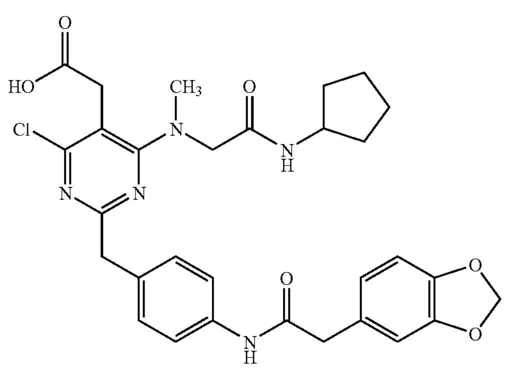 | 594.07 | 593 | 594 | >120 Z | C |
| 1-30 | 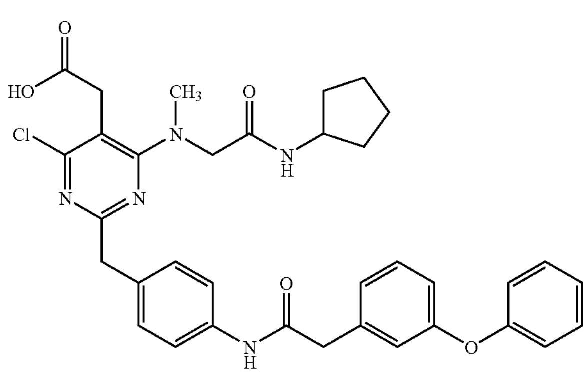 | 642.16 | 641 | 642 | >118 Z | A |

TABLE 1-continued
| Example # | Structure | MW | Exact Mass | MS | mp (° C.) | Activity class |
|---|---|---|---|---|---|---|
| 1-31 | 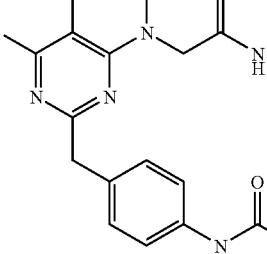 | 642.16 | 641 | 642 | >123 Z | B |
| 1-32 | 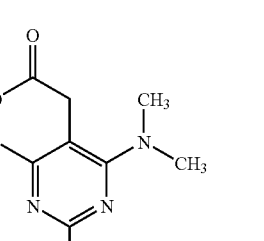 | 475.94 | 475 | 476 | 135-142 | A |
| 1-33 | 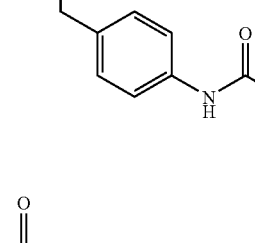 | 450.93 | 450 | 451 | >160 Z | A |
| 1-34 | 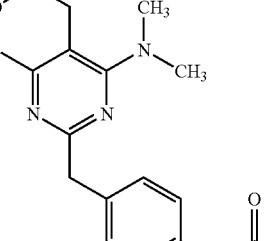 | 493.78 | 492 | 493 | >168 Z | A |

TABLE 1-continued

| Example # | Structure | MW | Exact Mass | MS | mp (° C.) | Activity class |
|---|---|---|---|---|---|---|
| 1-35 | 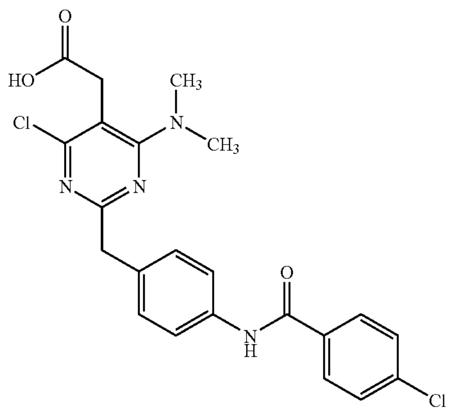 | 459.34 | 458 | 459 | >166 Z | A |
| 1-36 | 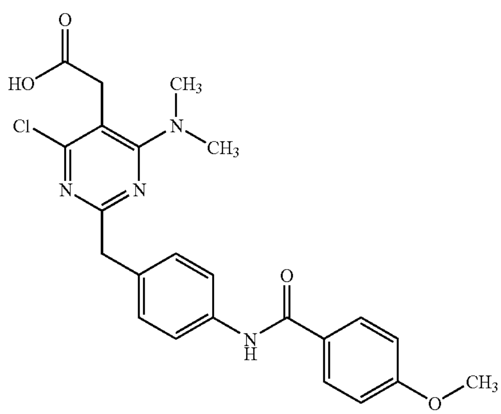 | 454.92 | 454 | 455 | >130 Z | A |
| 1-37 | 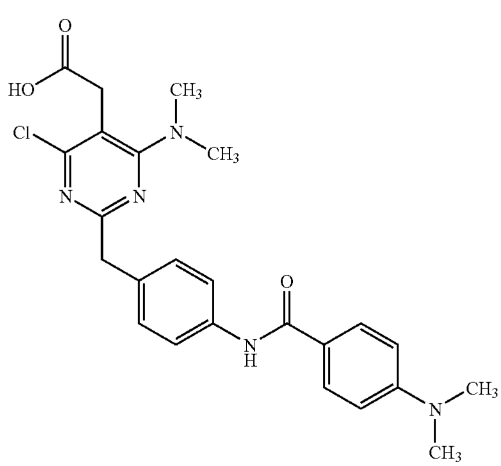 | 467.96 | 467 | 468 | >111 Z | A |

TABLE 1-continued

| Example # | Structure | MW | Exact Mass | MS | mp (° C.) | Activity class |
|---|---|---|---|---|---|---|
| 1-38 | 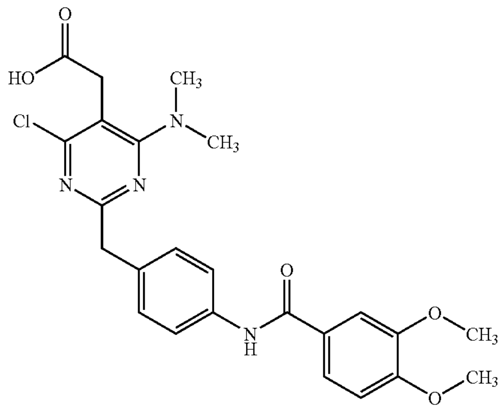 | 484.94 | 484 | 485 | >95 Z | B |
| 1-39 | 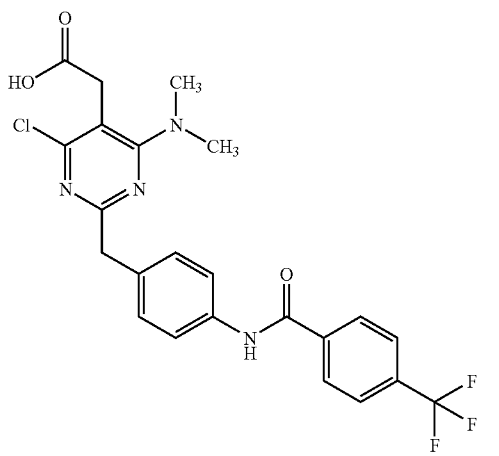 | 492.89 | 492 | 493 | >150 Z | A |
| 1-40 | 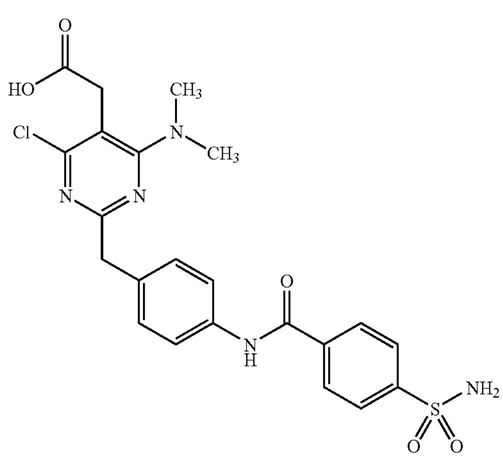 | 503.97 | 503 | 504 | oil | C |

TABLE 1-continued

| Example # | Structure | MW | Exact Mass | MS | mp (° C.) | Activity class |
|---|---|---|---|---|---|---|
| 1-41 | 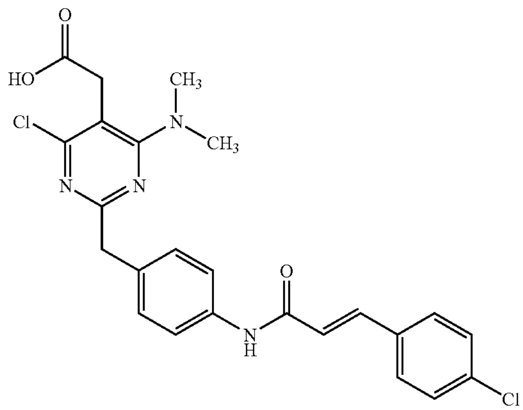 | 485.37 | 484 | 485 | 117 Z | A |
| 1-42 | 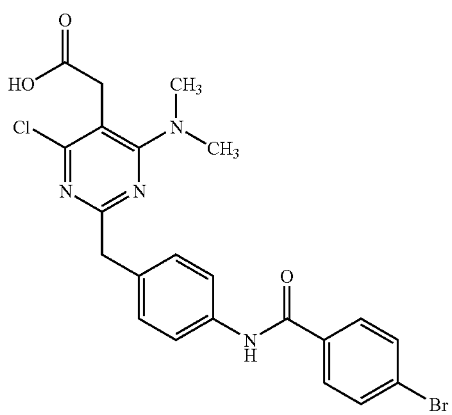 | 503.79 | 503 | 504 | 100 Z | A |
| 1-43 | 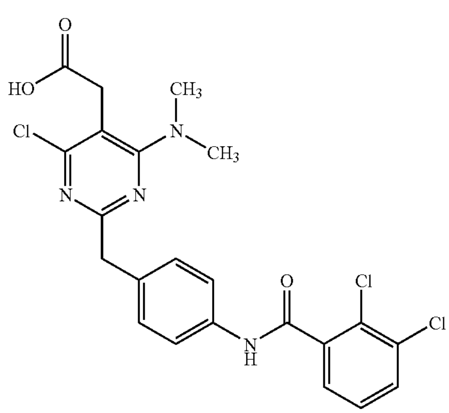 | 493.78 | 492.00 | 493.00 | 101 Z | C |

TABLE 1-continued

| Example # | Structure | MW | Exact Mass | MS | mp (° C.) | Activity class |
|---|---|---|---|---|---|---|
| 1-44 | 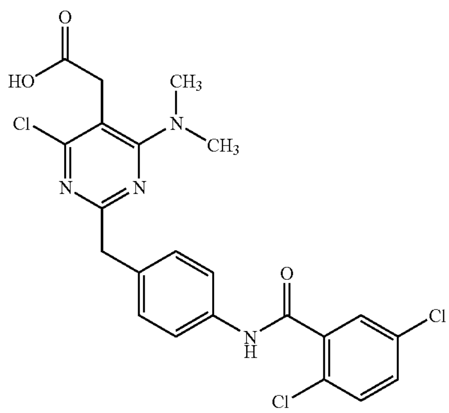 | 493.78 | 492 | 493 | 96 Z | A |
| 1-45 | 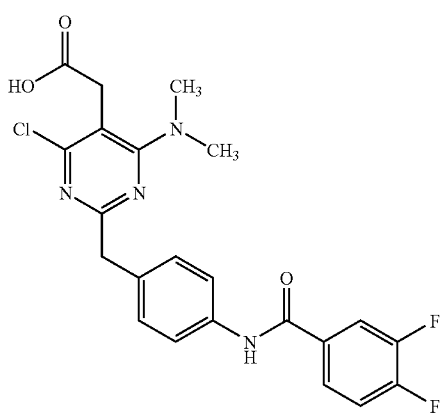 | 460.87 | 460 | 461 | >94 Z | A |
| 1-46 | 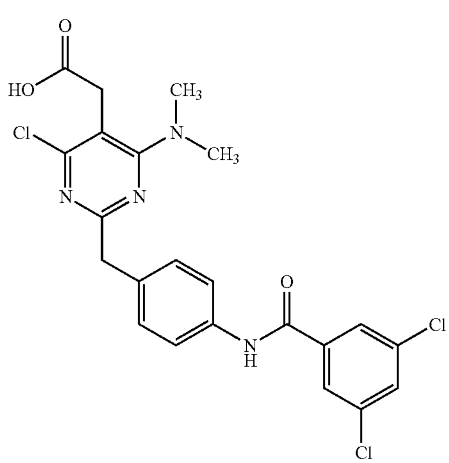 | 493.78 | 492 | 493 | >99 Z | A |

TABLE 1-continued

| Example # | Structure | MW | Exact Mass | MS | mp (° C.) | Activity class |
|---|---|---|---|---|---|---|
| 1-47 | 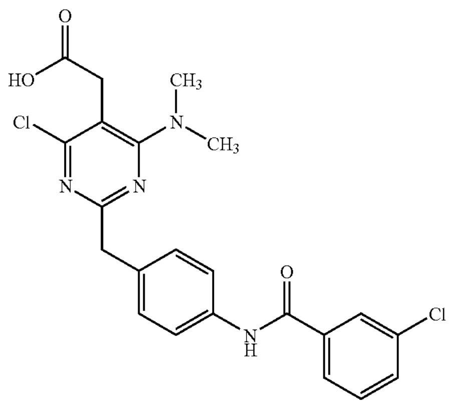 | 459.34 | 458 | 459 | >108 Z | A |
| 1-48 | 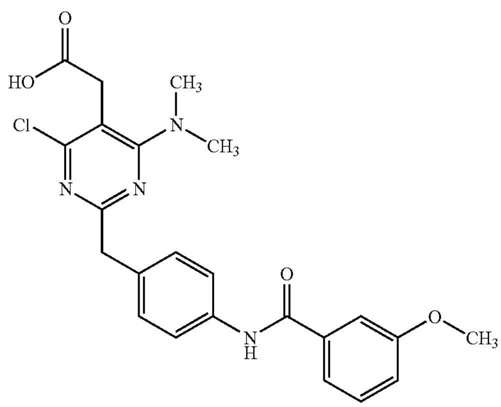 | 454.92 | 454 | 455 | >75 | A |
| 1-49 | 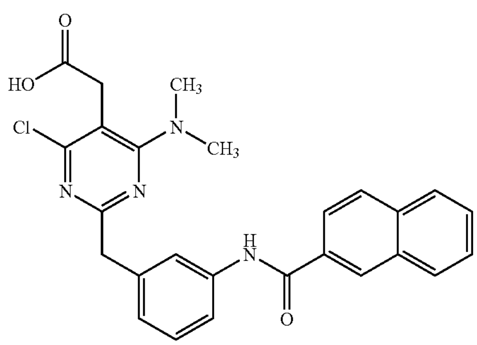 | 474.95 | 474 | 475 | 186 | B |
| 1-50 | 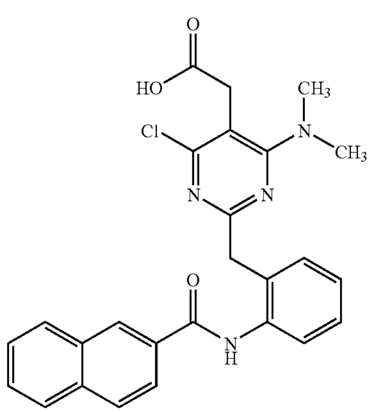 | 474.95 | 474 | 475 | 295 Z | D |

TABLE 1-continued

| Example # | Structure | MW | Exact Mass | MS | mp (° C.) | Activity class |
|---|---|---|---|---|---|---|
| 1-51 | 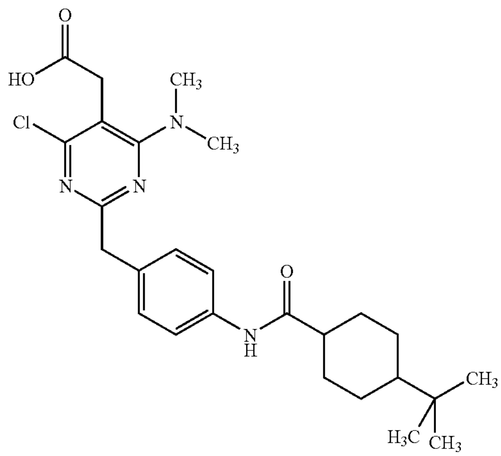 | 487.05 | 486 | 487 | 104 Z | A |
| 1-52 | 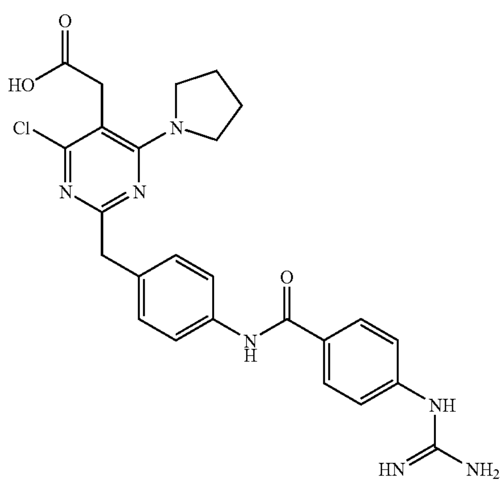 | 507.98 | 507 | 508 | 176 | D |
| 1-53 | 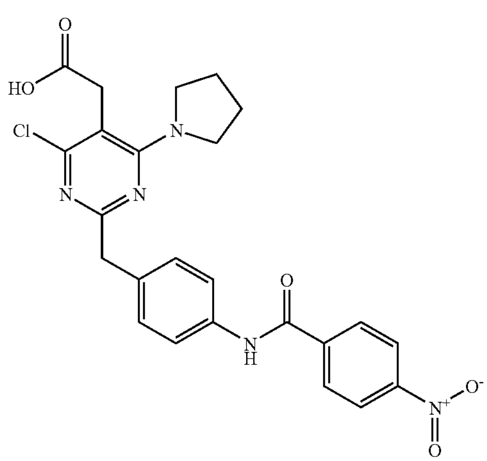 | 495.93 | 495 | 496 | 134 Z | B |

TABLE 1-continued

| Example # | Structure | MW | Exact Mass | MS | mp (° C.) | Activity class |
|---|---|---|---|---|---|---|
| 1-54 | 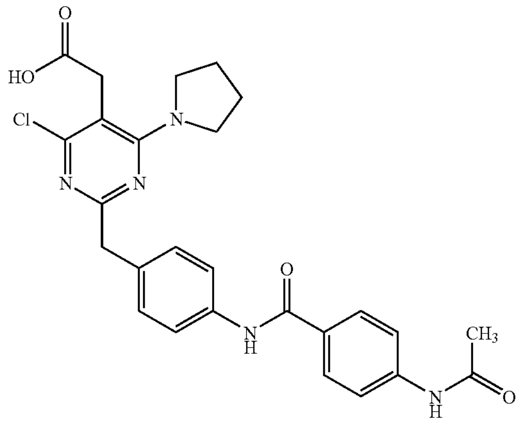 | 507.98 | 507.00 | 508.00 | 189 Z | B |
| 1-55 | 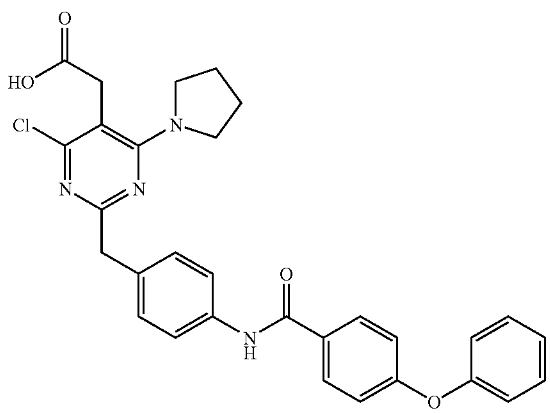 | 543.03 | 542 | 543 | 160 | A |
| 1-56 | 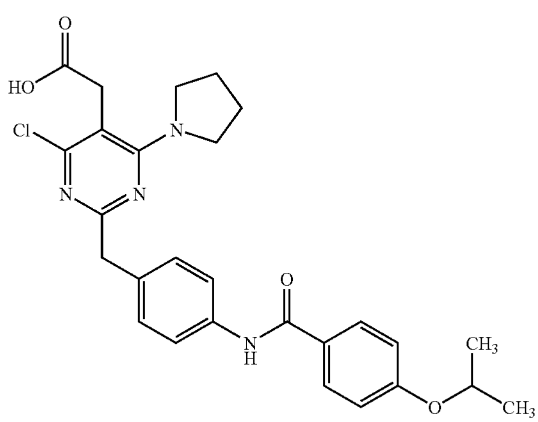 | 509.01 | 508 | 509 | 156 Z | A |

TABLE 1-continued

| Example # | Structure | MW | Exact Mass | MS | mp (° C.) | Activity class |
|---|---|---|---|---|---|---|
| 1-57 | 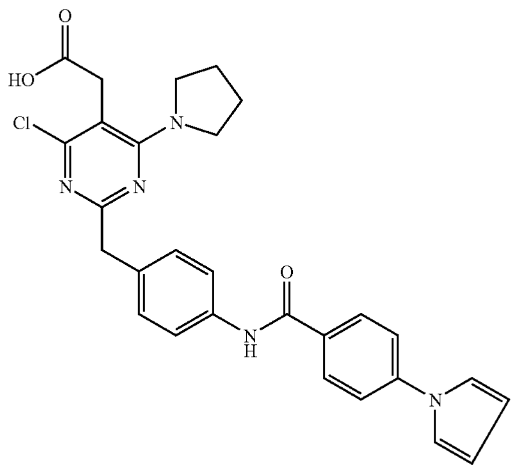 | 516.00 | 515 | 516 | 217 Z | A |
| 1-58 | 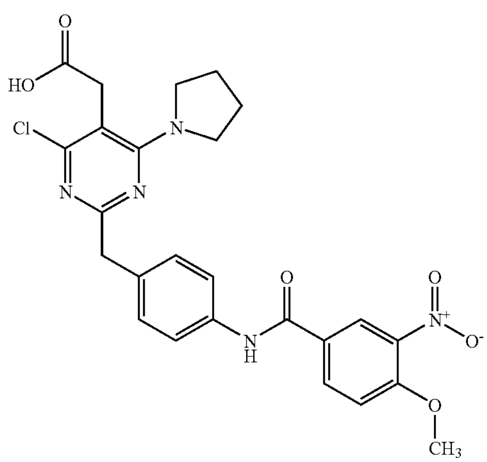 | 525.95 | 525 | 526 | 118 | A |
| 1-59 | 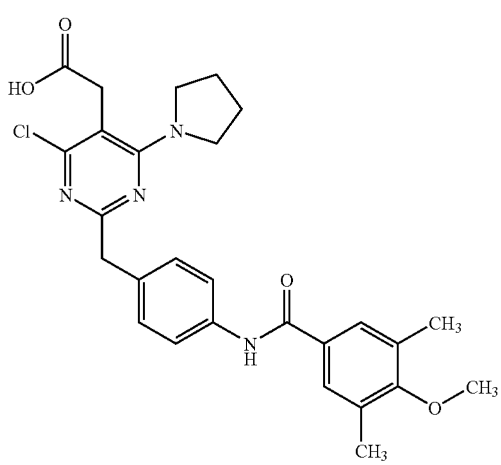 | 509.01 | 508 | 509 | 115 Z | A |

TABLE 1-continued

| Example # | Structure | MW | Exact Mass | MS | mp (° C.) | Activity class |
|---|---|---|---|---|---|---|
| 1-60 | 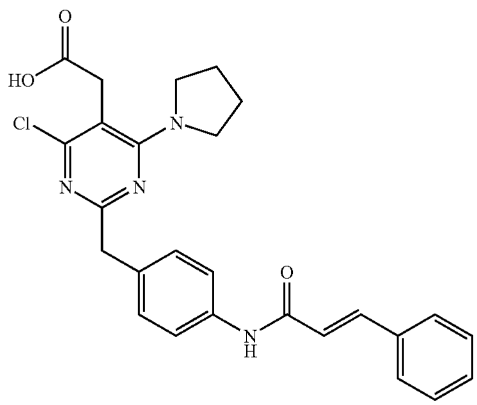 | 476.97 | 476 | 477 | 120 Z | A |
| 1-61 | 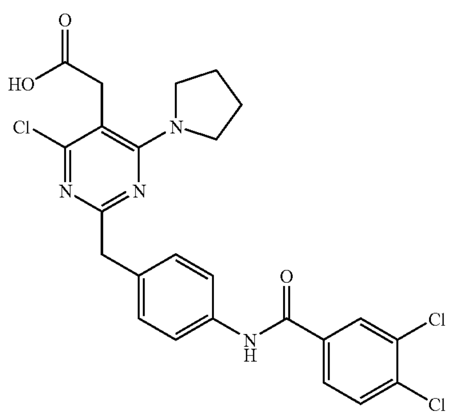 | 519.82 | 518 | 519 | 129 Z | A |
| 1-62 | 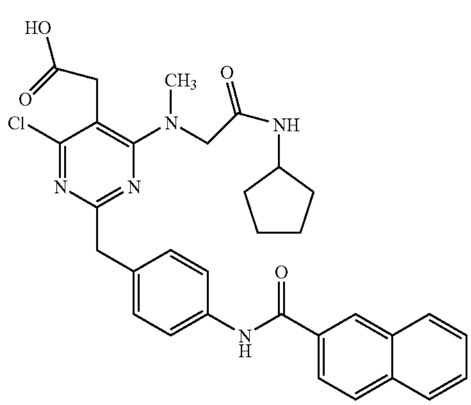 | 586.10 | 585 | 586 | >176 Z | A |

TABLE 1-continued

| Example # | Structure | MW | Exact Mass | MS | mp (° C.) | Activity class |
|---|---|---|---|---|---|---|
| 1-63 | 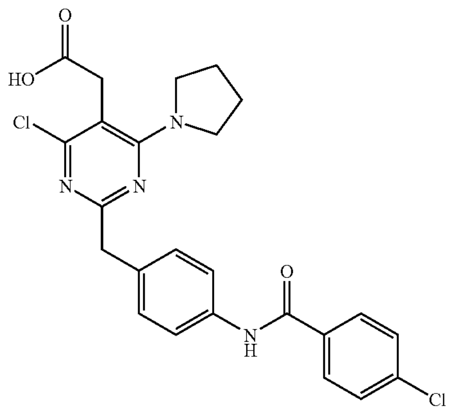 | 485.37 | 484 | 485 | 173 Z | A |
| 1-64 | 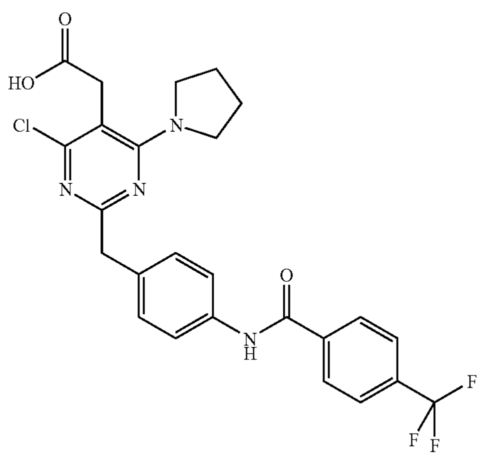 | 518.93 | 518 | 519 | 162 | A |
| 1-65 | 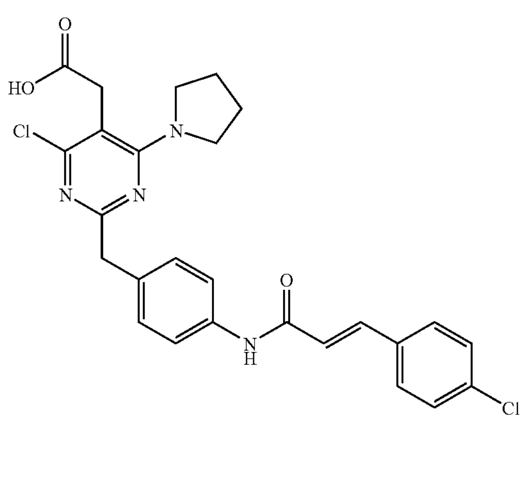 | 511.41 | 510 | 511 | 188-190 | A |

| Example # | Structure | MW | Exact Mass | MS | mp (° C.) | Activity class |
|---|---|---|---|---|---|---|
| 1-66 | 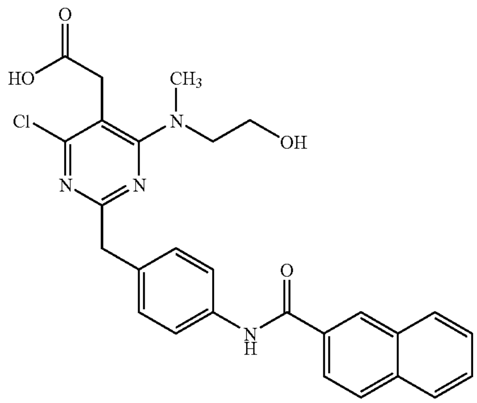 | 504.98 | 504 | 505 | 140 Z | A |
| 1-67 | 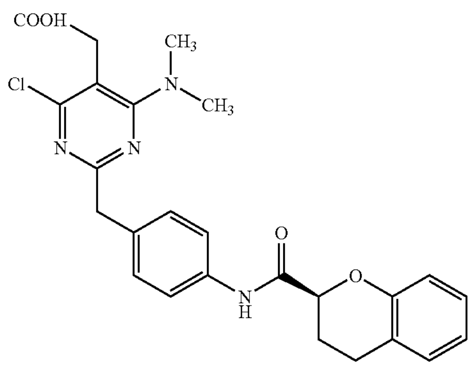 | 480.96 | 480 | 481 | >120 Z | A |
| 1-68 | 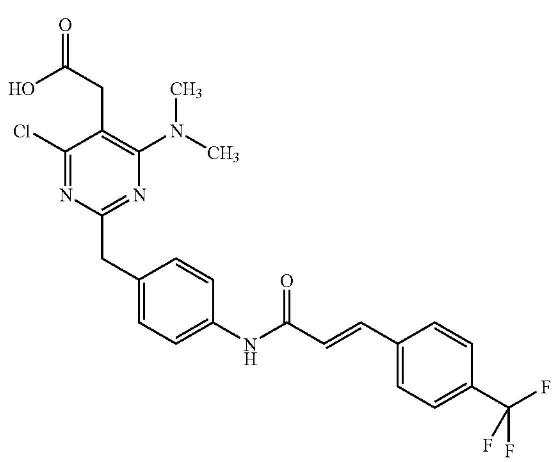 | 518.93 | 518 | 519 | >199 Z | A |

Methyl[2-(4-aminobenzyl)-4-(dimethylamino)pyrimidin-5-yl]acetate

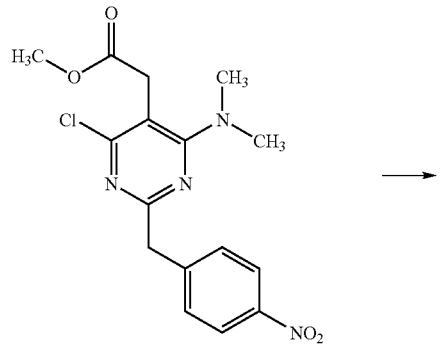

A suspension of methyl[4-chloro-6-(dimethylamino)-2-(4-nitrobenzyl)pyrimidin-5-yl]acetate (3.00 g, 8.22 mmol) and potassium acetate (2.42 g, 24.7 mmol) in methanol (30 mL) was treated with 10% Pd/C (1.00 g). The resulting black suspension was stirred under an atmosphere of hydrogen for 15 hours and then filtered over Celite. The residue was rinsed with methanol and the filtrate concentrated to dryness before partitioning between EtOAc and water. The separated organic layer was sequentially washed with saturated NaHCO$_3$ and brine, dried over anhydrous MgSO$_4$, filtered, and concentrated in vacuo. Chromatographic purification (silica gel, 1% MeOH in CHCl$_3$) of the thus obtained crude product then yielded methyl[2-(4-aminobenzyl)-4-(dimethylamino)pyrimidin-5-yl]acetate (2.40 g, 97% yield) as a brown oil.

Example 2-1

{4-(Dimethylamino)-2-[4-(2-naphthoylamino)benzyl]pyrimidin-5-yl}acetic acid

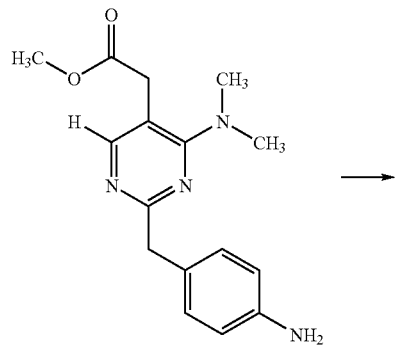

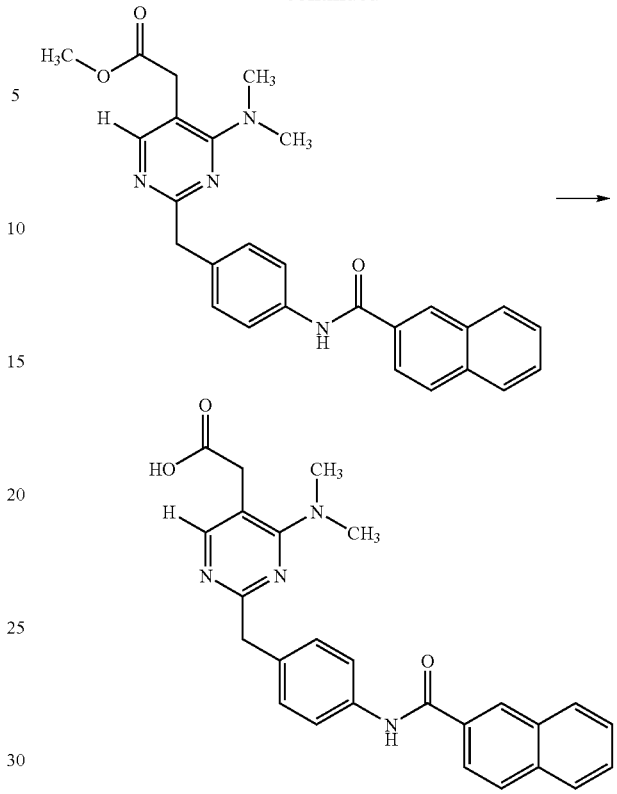

A solution containing methyl[2-(4-aminobenzyl)-4-(dimethylamino)pyrimidin-5-yl]acetate (0.090 g, 0.30 mmol) and PyBOP (0.187 g, 0.36 mmol) in anhydrous DMF (1 mL) at room temperature was treated with 2-naphthoic acid (0.062 g, 0.36 mmol). The reaction mixture was stirred for 3 hours before diluting with water. The thus quenched reaction mixture was extracted with EtOAc and the combined organic extracts was washed sequentially with 0.5N HCl, saturated NaHCO$_3$, and brine, dried over anhydrous MgSO$_4$, filtered, and concentrated to dryness to give the crude product methyl {4-(dimethylamino)-2-[4-(2-naphthoylamino)benzyl]pyrimidin-5-yl}acetate.

The thus obtained methyl {4-(dimethylamino)-2-[4-(2-naphthoylamino)benzyl]pyrimidin-5-yl}acetate was dissolved in THF (6 mL) and treated with 1N NaOH (3 mL). The biphashic reaction mixture was stirred at room temperature for 14 hours and then Et$_2$O was added. The organic layer was siphoned off and the remaining aqueous layer was neutralized with 6N HCl. The separated solids was collected by suction, triturated with diisopropyl ether, and filtered to give {4-(dimethylamino)-2-[4-(2-naphthoylamino)benzyl]pyrimidin-5-yl}acetic acid (0.047 g, 36% yield).

$^1$H NMR (500 MHz, DMSO-d$_6$) δ: 3.04 (s, 6H), 3.65 (s, 2H), 3.93 (s, 2H), 7.32 (d, J=9 Hz, 2H), 7.60-7.66 (m, 2H), 7.73 (d, J=9 Hz, 2H), 7.97 (s, 1H), 8.00-8.09 (m, 4H), 10.35 (s, 1H), 12.54 (s, 1H).

Molecular weight: 440.51

Mass spectrometry: 441

Melting point: 210° C.

Activity class: A

In a similar manner as described in Example 2-1, compounds in Example 2-2 to 2-36 as shown in Table 2 were synthesized.

TABLE 2

| example # | Structure | MW | Exact Mass | MS | mp (° C.) | Activity class |
|---|---|---|---|---|---|---|
| 2-2 | 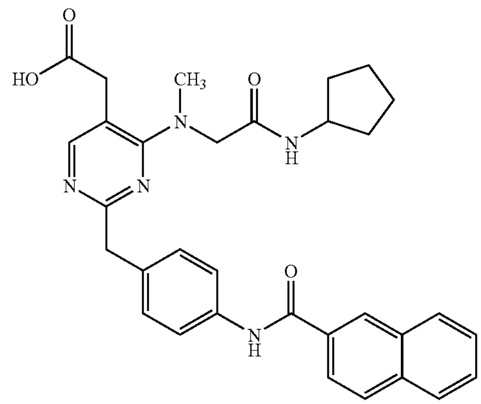 | 551.64 | 551 | 552 | 287 Z | A |
| 2-3 | 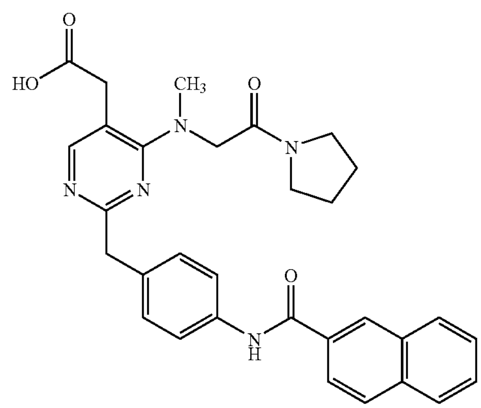 | 537.62 | 537 | 538 | 201 Z | A |
| 2-4 | 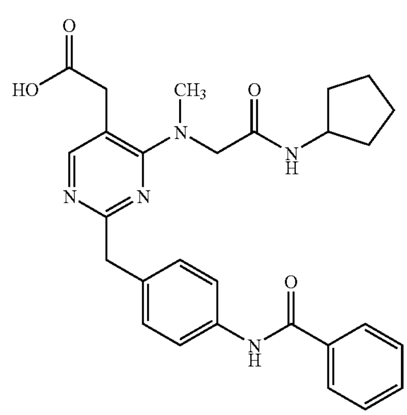 | 501.59 | 501 | 502 | 212 Z | B |

TABLE 2-continued
| example # | Structure | MW | Exact Mass | MS | mp (° C.) | Activity class |
|---|---|---|---|---|---|---|
| 2-5 | 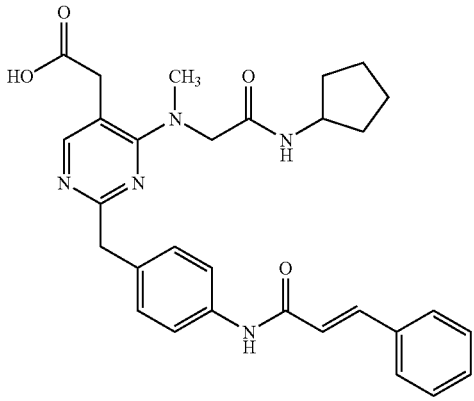 | 527.63 | 527 | 528 | 209 Z | A |
| 2-6 | 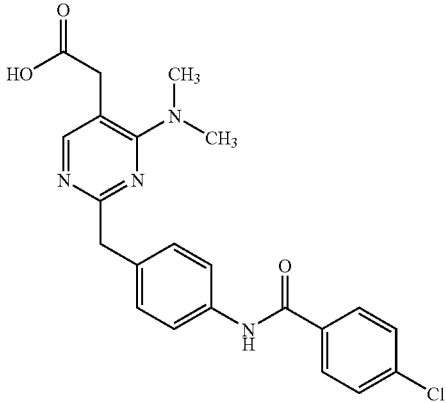 | 424.89 | 524 | 525 | 147 | A |
| 2-7 | 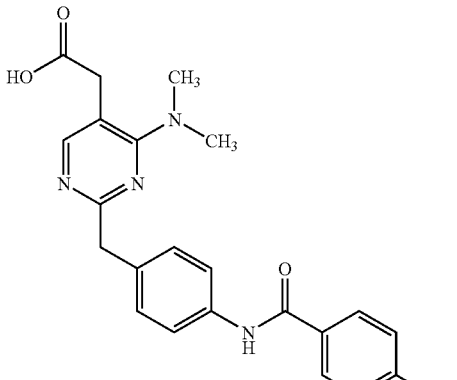 | 420.47 | 420 | 421 | 111 | A |

TABLE 2-continued

| example # | Structure | MW | Exact Mass | MS | mp (° C.) | Activity class |
|---|---|---|---|---|---|---|
| 2-8 | 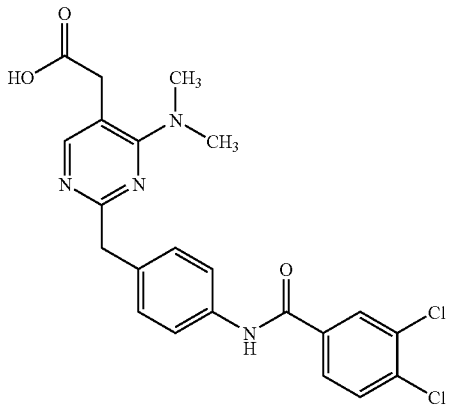 | 459.34 | 458 | 459 | 140 | A |
| 2-9 | 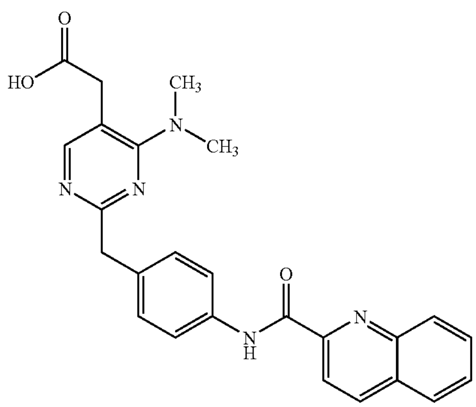 | 441.49 | 441 | 442 | 136-144 | B |
| 2-10 | 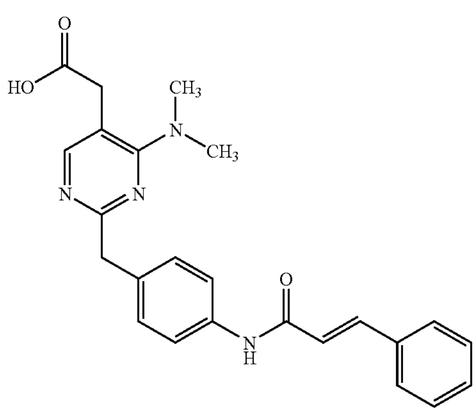 | 416.48 | 416 | 417 | 135-140 | A |

TABLE 2-continued

| example # | Structure | MW | Exact Mass | MS | mp (° C.) | Activity class |
|---|---|---|---|---|---|---|
| 2-11 | 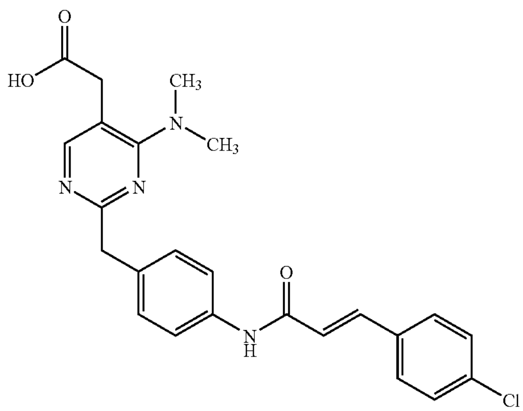 | 450.93 | 450 | 451 | 136-140 | A |
| 2-12 | 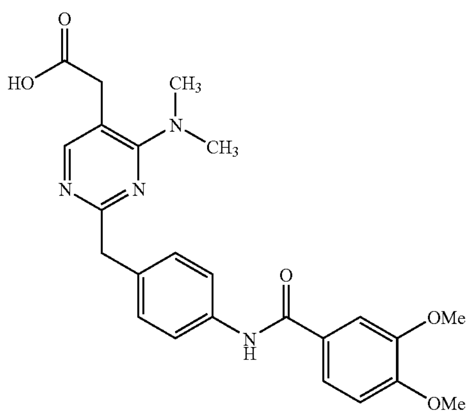 | 450.50 | 450 | 451 | 106-110 | C |
| 2-13 | 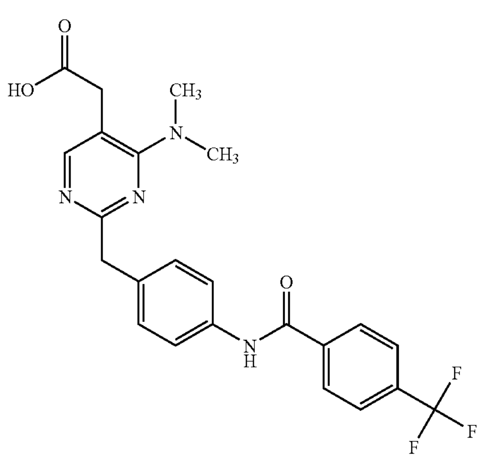 | 458.44 | 458 | 459 | 149-153 | A |

TABLE 2-continued

| example # | Structure | MW | Exact Mass | MS | mp (° C.) | Activity class |
|---|---|---|---|---|---|---|
| 2-14 | 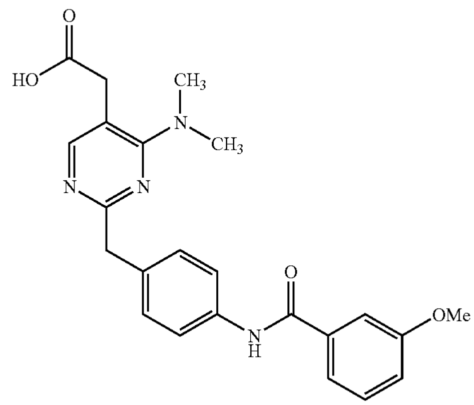 | 420.47 | 420 | 421 | 94 Z | B |
| 2-15 | 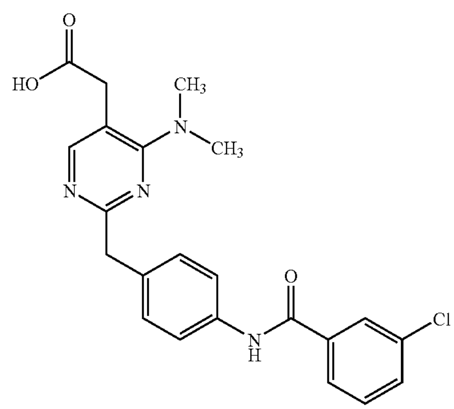 | 424.89 | 424 | 425 | 111-113 | B |
| 2-16 | 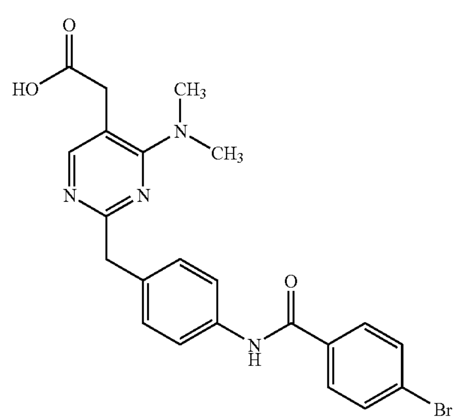 | 469.34 | 469 | 470 | 220 Z | A |

TABLE 2-continued

| example # | Structure | MW | Exact Mass | MS | mp (° C.) | Activity class |
|---|---|---|---|---|---|---|
| 2-17 | 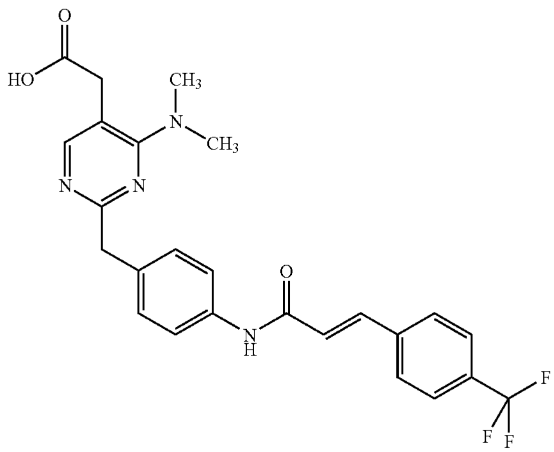 | 484.48 | 484 | 485 | >178 Z | A |
| 2-18 | 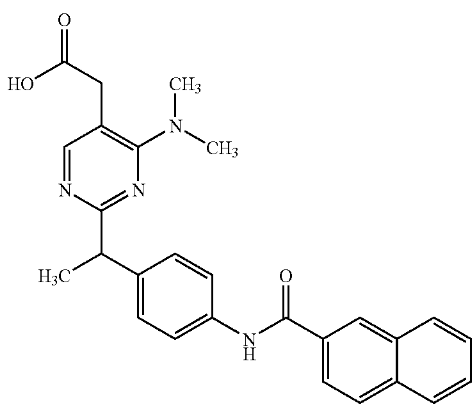 | 454.53 | 454 | 455 | >128 Z | A |
| 2-19 | 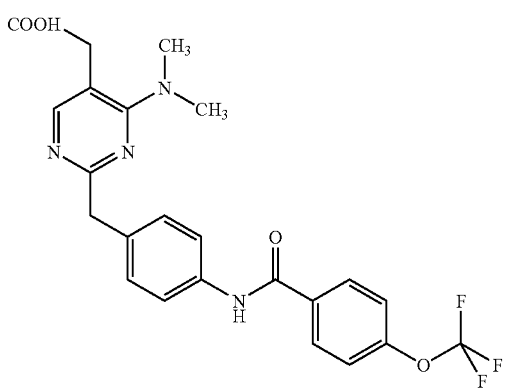 | 474.44 | 474 | 475 | >238 Z | A |

TABLE 2-continued
| example # | Structure | MW | Exact Mass | MS | mp (° C.) | Activity class |
|---|---|---|---|---|---|---|
| 2-20 | 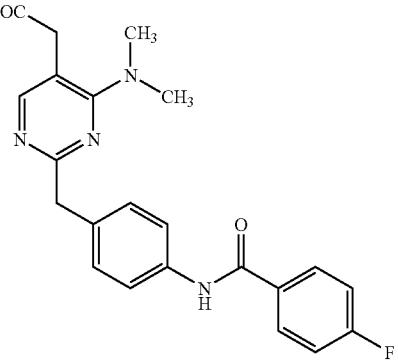 | 408.44 | 408 | 409 | >136 Z | B |
| 2-21 | 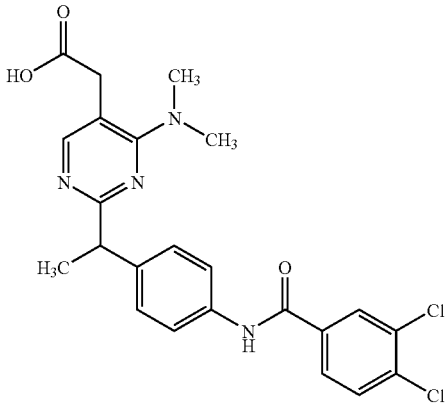 | 473.36 | 472 | 473 | 137-140 | A |
| 2-22 | 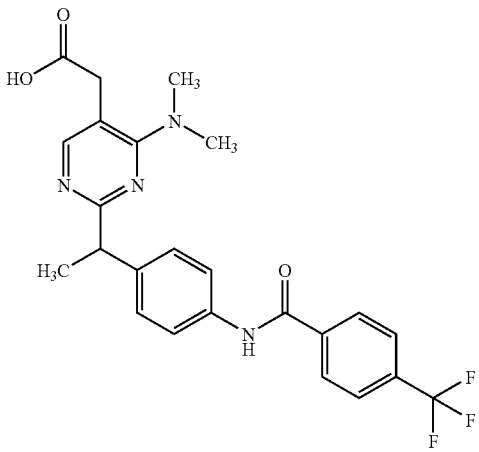 | 472.47 | 472 | 473 | 151-154 | A |

TABLE 2-continued

| example # | Structure | MW | Exact Mass | MS | mp (° C.) | Activity class |
|---|---|---|---|---|---|---|
| 2-23 | 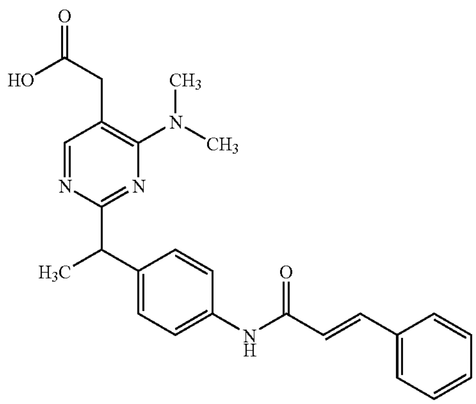 | 430.51 | 430 | 431 | 150-153 | A |
| 2-24 | 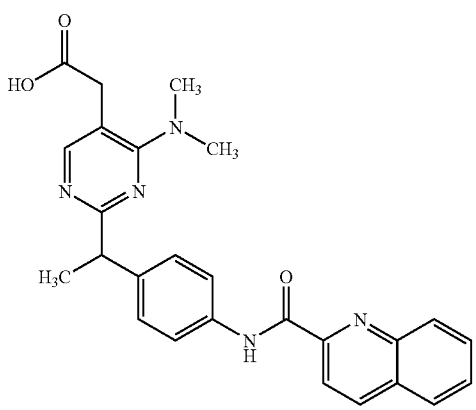 | 455.52 | 455 | 456 | 120-123 | B |
| 2-25 | 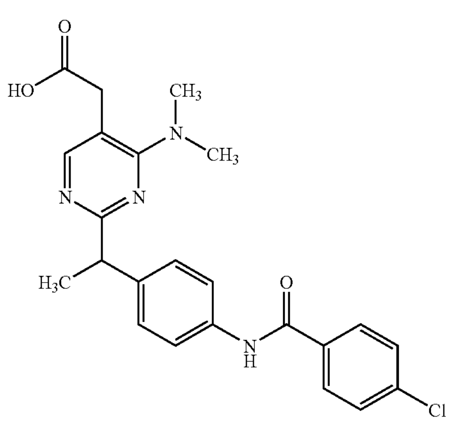 | 438.92 | 438 | 439 | 131-134 | A |

TABLE 2-continued

| example # | Structure | MW | Exact Mass | MS | mp (° C.) | Activity class |
|---|---|---|---|---|---|---|
| 2-26 | 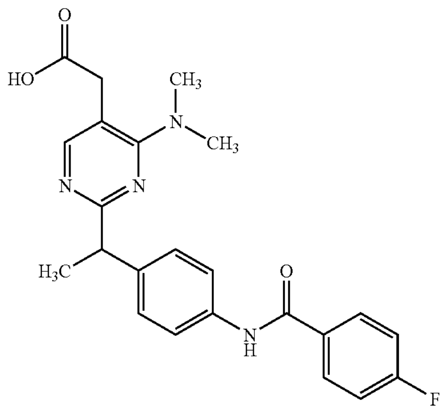 | 422.46 | 422 | 423 | 114-117 | A |
| 2-27 | 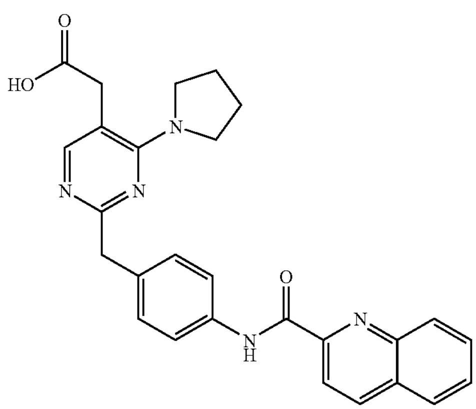 | 467.53 | 467 | 468 | 221-224 Z | A |
| 2-28 | 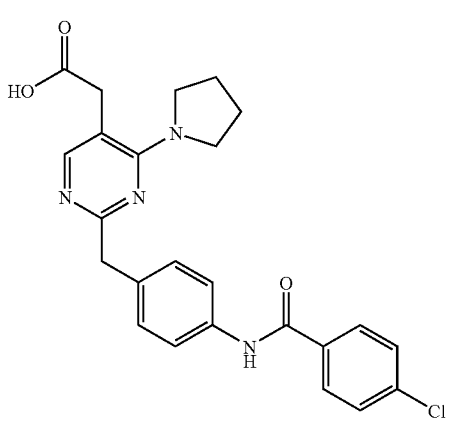 | 450.93 | 450 | 451 | 151-153 | A |

TABLE 2-continued

| example # | Structure | MW | Exact Mass | MS | mp (° C.) | Activity class |
|---|---|---|---|---|---|---|
| 2-29 | 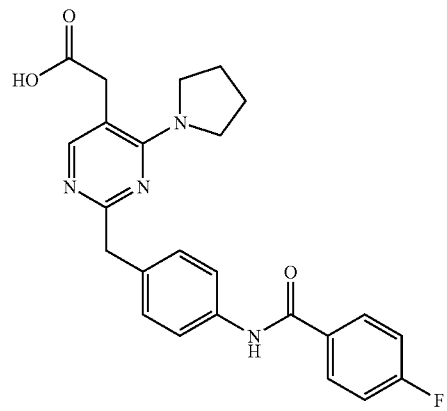 | 434.47 | 434 | 435 | 143-145 | A |
| 2-30 | 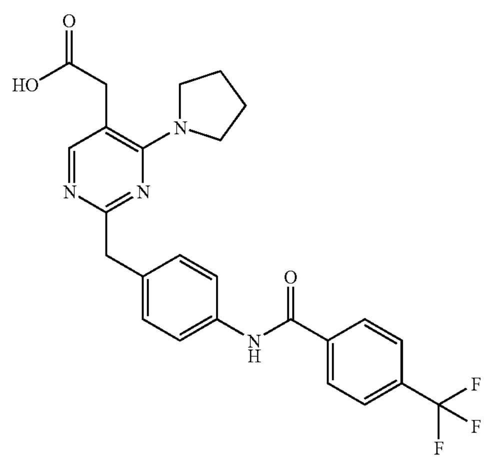 | 484.48 | 484 | 485 | 156-158 Z | A |
| 2-31 | 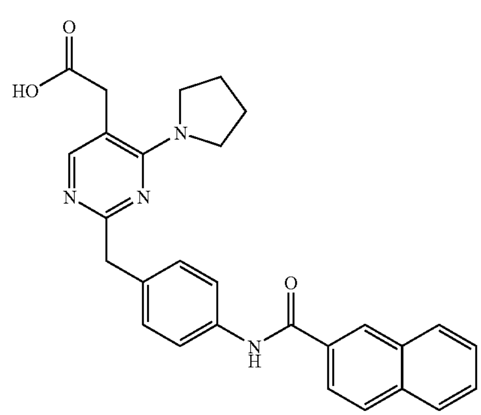 | 466.54 | 466 | 467 | 150-151 | A |

TABLE 2-continued

| example # | Structure | MW | Exact Mass | MS | mp (° C.) | Activity class |
|---|---|---|---|---|---|---|
| 2-32 | 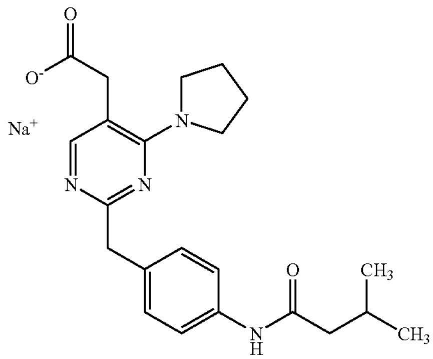 | 418.48 | 396 | 397 | 148-150 | B |
| 2-33 | 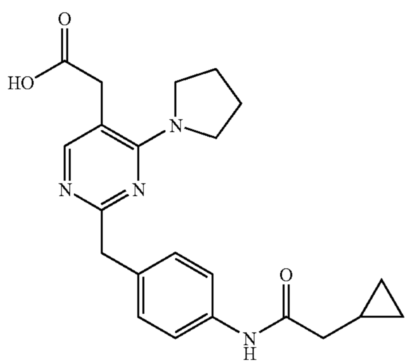 | 394.48 | 394 | 395 | 145-148 z | C |
| 2-34 | 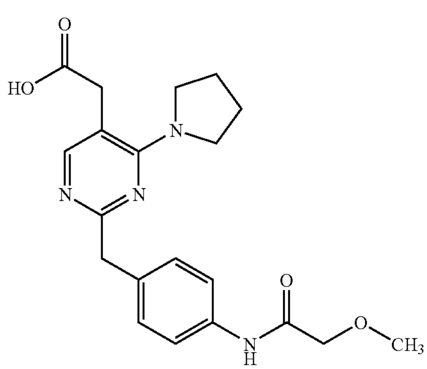 | 384.44 | 384 | 385 | 102-105 | D |

TABLE 2-continued

| example # | Structure | MW | Exact Mass | MS | mp (° C.) | Activity class |
|---|---|---|---|---|---|---|
| 2-35 | 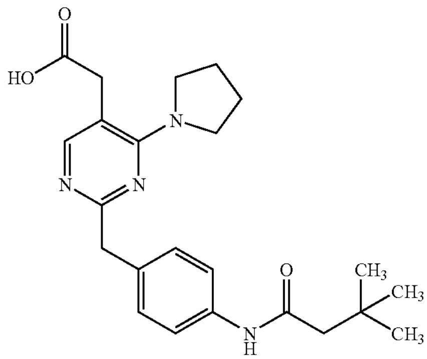 | 410.52 | 410 | 411 | 147-150 | B |
| 2-36 | 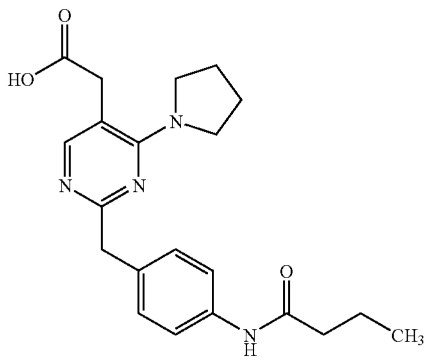 | 382.47 | 382 | 383 | 130-133 | C |

Methyl[2-(4-aminobenzyl)-4,6-dichloropyrimidin-5-yl]acetate

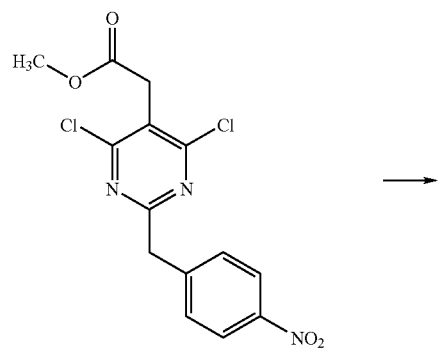

A solution of methyl[4,6-dichloro-2-(4-nitrobenzyl)pyrimidin-5-yl]acetate (2.00 g, 5.62 mmol) in anhydrous THF (50 mL) was treated with Pd/C (10% Pd, 0.200 g) and the resulting black suspension was stirred under an atmosphere of hydrogen at room temperature. After 16 hours, the reaction mixture was filtered over Celite and the residue rinsed with copious amounts of MeOH. The filtrate was concentrated in vacuo to give the crude product as a dark yellow oil which was chromatographed (silica gel, 40% EtOAc in n-hexane) to give methyl[2-(4-aminobenzyl)-4,6-dichloropyrimidin-5-yl]acetate (1.32 g, 72% yield) as a white powder.

Methyl {4,6-dichloro-2-[4-(2-naphthoylamino)benzyl]pyrimidin-5-yl}acetate

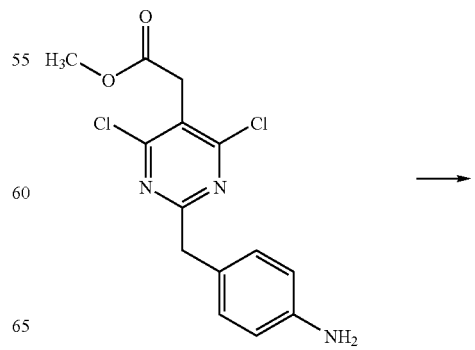

-continued

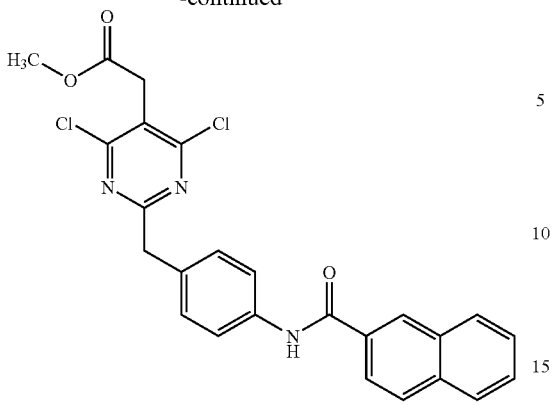

A mixture of methyl[2-(4-aminobenzyl)-4,6-dichloropyrimidin-5-yl]acetate (0.073 g, 0.23 mmol), 2-naphthoic acid (0.048 g, 0.028 mmol), and WSCI (0.049 g, 0.026 mmol) in anhydrous THF (3 mL) was stirred at room temperature under Ar atmosphere for 10 hours. EtOAc (80 mL) was then introduced and the organic phase was washed sequentially with saturated NaHCO₃, water, and brine, dried over anhydrous MgSO₄, filtered, and concentrated in vacuo. The crude product thus obtained as a light orange oil was triturated with diisopropyl ether and the separated solids was collected by suction to give methyl {4,6-dichloro-2-[4-(2-naphthoylamino)benzyl]pyrimidin-5-yl}acetate (0.090 g, 78% yield) as a white powder.

Example 3-1

{4-Chloro-2-[4-(2-naphthoylamino)benzyl]-6-pyrrolidin-1-ylpyrimidin-5-yl}acetic acid

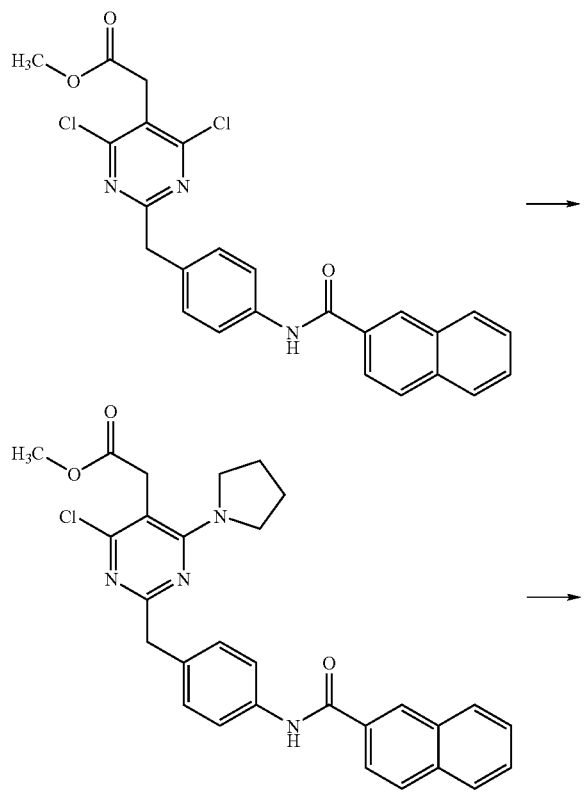

-continued

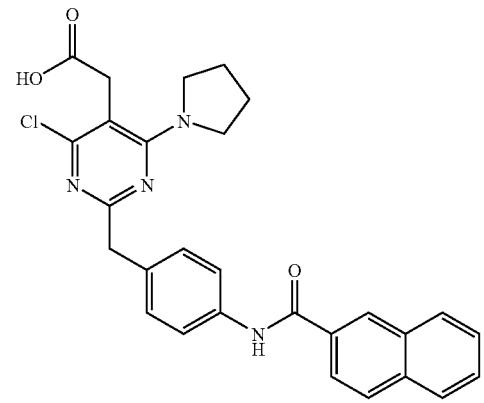

A mixture of methyl {4,6-dichloro-2-[4-(2-naphthoylamino)benzyl]pyrimidin-5-yl}acetate (0.100 g, 0.21 mmol), pyrrolidine (0.019 mL, 0.23 mmol), and N,N-diisopropylethylamine (0.109 mL, 0.62 mmol) in anhydrous DMF (2 mL) was stirred at 80° C. for 5 hours. After cooling to room temperature, the solvent was evaporated and the remaining residue dissolved in EtOAc. This organic solution was sequentially washed with 1N HCl, water, and brine, dried over anhydrous MgSO₄, filtered, and concentrated in vacuo. Purification by preparative TLC then afforded methyl {4-chloro-2-[4-(2-naphthoylamino)benzyl]-6-pyrrolidin-1-ylpyrimidin-5-yl}-acetate (0.100 g, 95% yield) as a white powder.

A solution of methyl {4-chloro-2-[4-(2-naphthoylamino)benzyl]-6-pyrrolidin-1-ylpyrimidin-5-yl}acetate (0.085 g, 0.17 mmol) in THF (3 mL) was treated with 1N NaOH (1.5 mL) and the biphasic mixture was stirred at room temperature for 45 hours. Et₂O was then added and the organic layer siphoned off. The remaining aqueous layer was cooled to 0° C. and acidified with 6N HCl. The separated solids were collected by suction and rinsed with water. Drying under high vacuum at 45° C. for 5 hours gave {4-chloro-2-[4-(2-naphthoylamino)benzyl]-6-pyrrolidin-1-ylpyrimidin-5-yl}acetic acid (0.050 g, 56% yield) as an off-white powder.

$^1$H NMR (300 MHz, DMSO-d₆) δ: 1.86 (bs, 4H), 3.59 (bs, 4H), 3.78 (s, 2H), 3.88 (s, 2H), 7.32 (d, J=9 Hz, 2H), 7.63 (m, 2H), 7.96-8.13 (m, 414), 8.57 (s, 1H), 10.39 (s, 1H), 12.72 (s, 1H).

Molecular weight: 500.99

Mass spectrometry: 501

Melting point: 196 Z° C.

Activity class: A

In a similar manner as described in Example 3-1, compounds in Example 3-2 to 3-16 as shown in Table 3 were synthesized.

TABLE 3

| Example # | Structure | MW | Exact Mass | MS | mp (°C.) | Activity class |
|---|---|---|---|---|---|---|
| 3-2 | 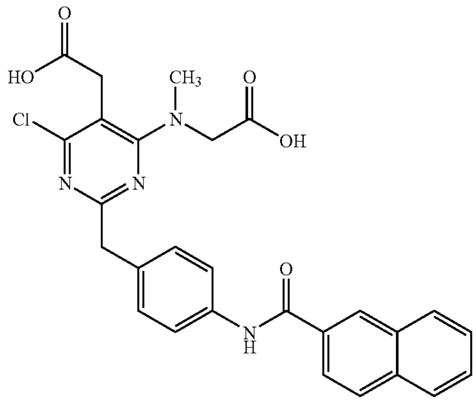 | 518.96 | 518 | 519 | 176 Z | B |
| 3-3 | 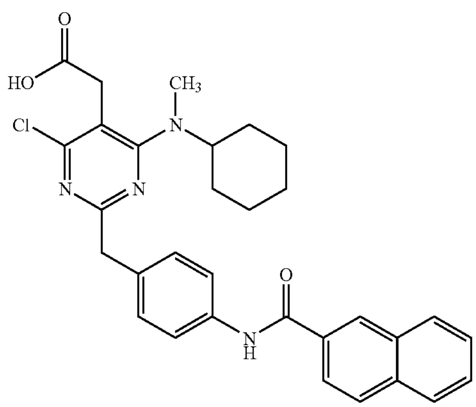 | 543.07 | 542 | 543 | 185 Z | A |
| 3-4 | 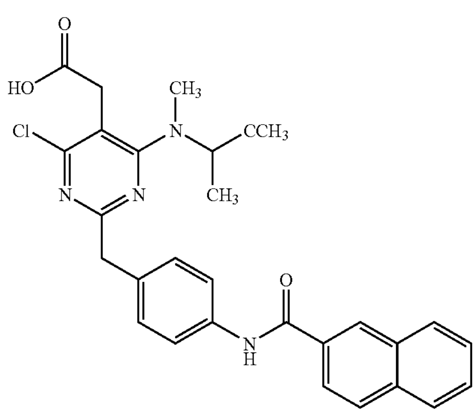 | 503.01 | 502 | 503 | 132 Z | A |

TABLE 3-continued

| Example # | Structure | MW | Exact Mass | MS | mp (° C.) | Activity class |
|---|---|---|---|---|---|---|
| 3-5 | 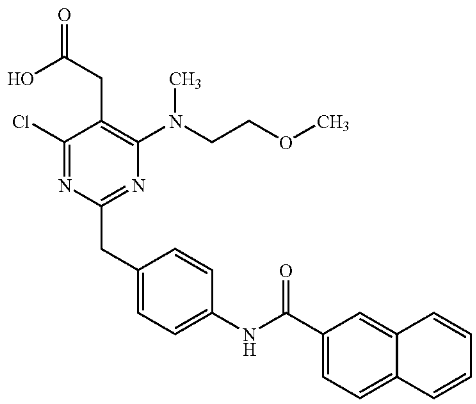 | 519.00 | 518 | 519 | 144 | A |
| 3-6 | 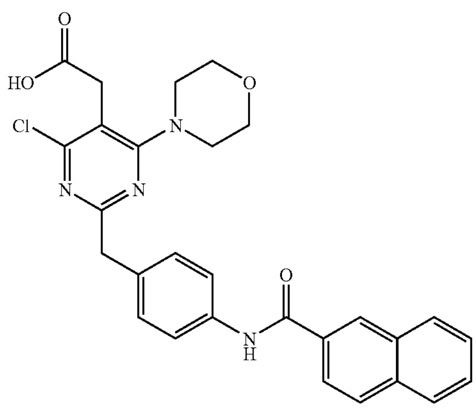 | 516.99 | 516 | 517 | 172 Z | A |
| 3-7 | 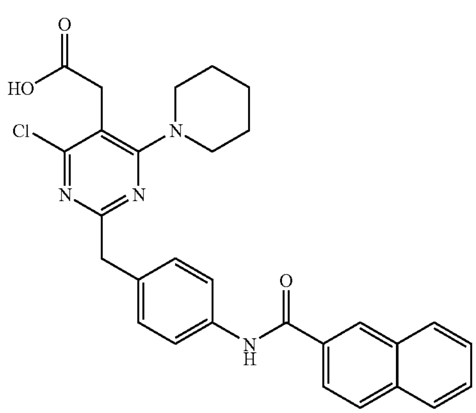 | 515.02 | 514 | 515 | 157 Z | A |

TABLE 3-continued

| Example # | Structure | MW | Exact Mass | MS | mp (° C.) | Activity class |
|---|---|---|---|---|---|---|
| 3-8 | 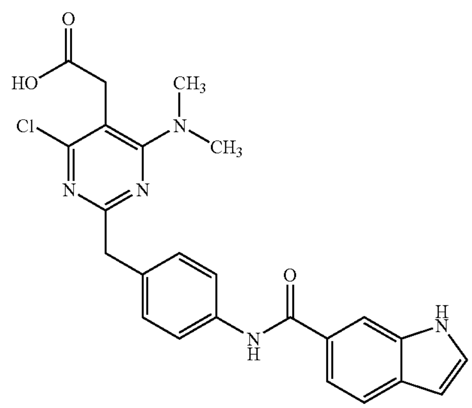 | 463.93 | 463 | 464 | >165 Z | A |
| 3-9 | 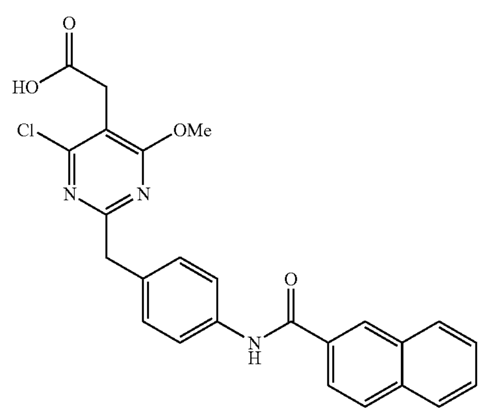 | 461.91 | 461 | 462 | 201 Z | A |
| 3-10 | 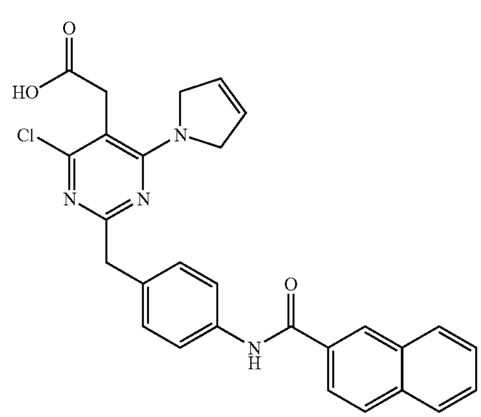 | 498.97 | 498 | 499 | >146 Z | A |

TABLE 3-continued

| Example # | Structure | MW | Exact Mass | MS | mp (°C.) | Activity class |
|---|---|---|---|---|---|---|
| 3-11 | 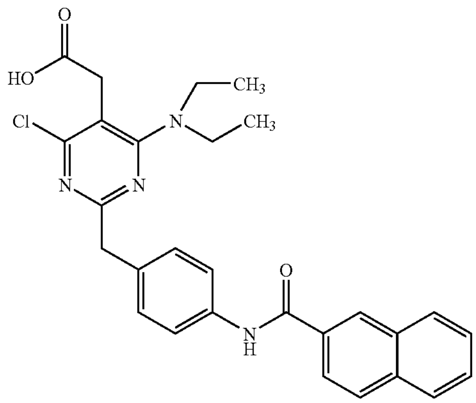 | 503.01 | 502 | 503 | >90 Z | B |
| 3-12 | 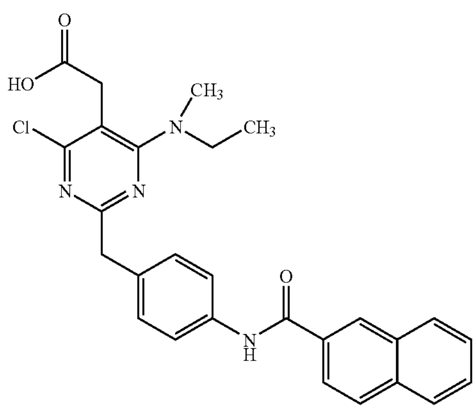 | 488.98 | 488 | 489 | >125 Z | A |
| 3-13 | 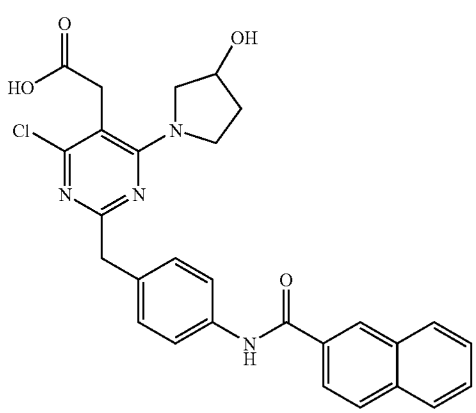 | 516.99 | 516 | 517 | >202 Z | A |

TABLE 3-continued

| Example # | Structure | MW | Exact Mass | MS | mp (°C.) | Activity class |
|---|---|---|---|---|---|---|
| 3-14 | 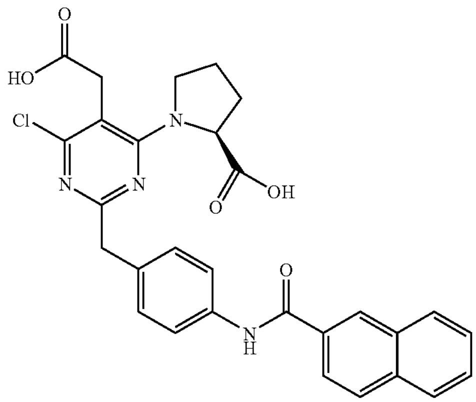 | 545.00 | 544 | 545 | >174 Z | B |
| 3-15 | 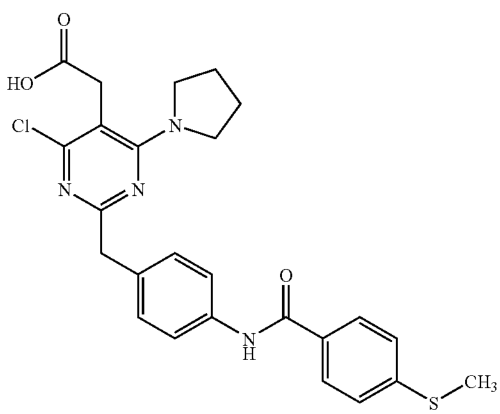 | 497.02 | 496 | 497 | 157 Z | A |
| 3-16 | 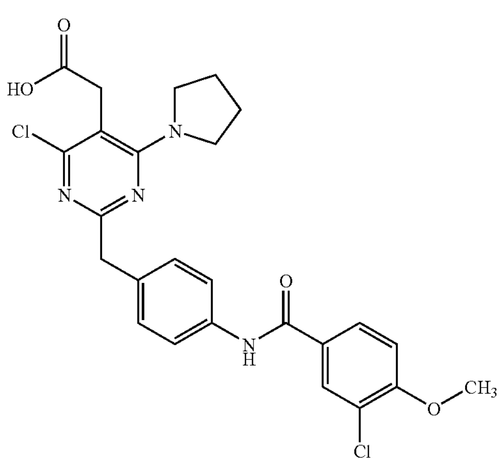 | 515.40 | 514 | 515 | 108 Z | A |

Example 4-1

{2-{4-[(Anilinocarbonyl)amino]benzyl}-4-chloro-6-[[2-(cyclopentylamino)-2-oxoethyl](methyl)amino]pyrimidin-5-yl}acetatic acid

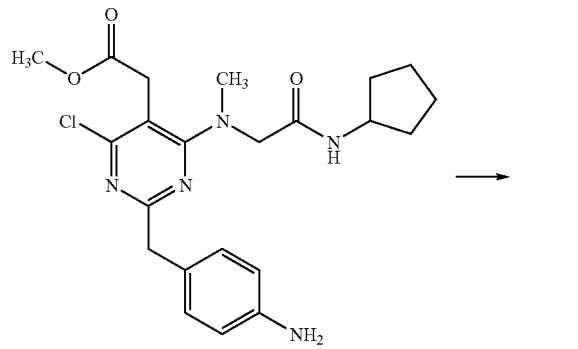

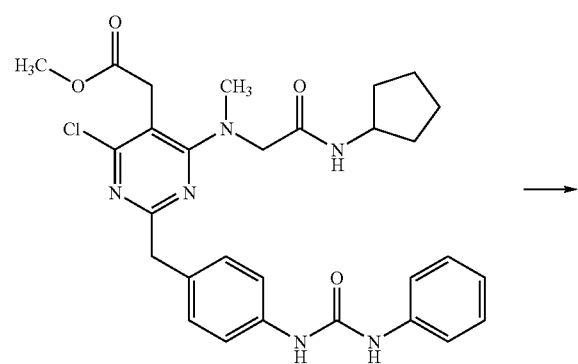

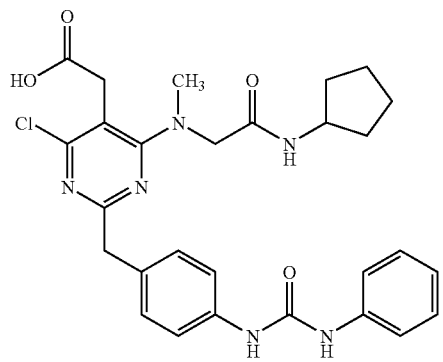

A solution of methyl {2-(4-aminobenzyl)-4-chloro-6-[[2-(cyclopentylamino)-2-oxoethyl](methyl)-amino]pyrimidin-5-yl}acetate (0.050 g, 0.11 mmol) in DMF (2 mL) was treated with phenyl isocyanate (0.022 mL, 0.20 mmol). After stirring at room temperature for 18 hours, EtOAc was added and the organic phase was washed with 8% NaHCO$_3$ and brine, dried over anhydrous Na$_2$SO$_4$, filtered, and concentrated in vacuo. The crude product thus obtained was triturated with CH$_2$Cl$_2$ and diisopropyl ether to give methyl {2-{4-[(anilinocarbonyl)amino]benzyl}-4-chloro-6-[[(2-(cyclopentylamino)-2-oxoethyl](methyl)amino]pyrimidin-5-yl}acetate (0.055 g, 87% yield) as a white powder.

To a solution of methyl {2-{4-[(anilinocarbonyl)amino]benzyl}-4-chloro-6-[[2-(cyclopentyl-amino)-2-oxoethyl](methyl)amino]pyrimidin-5-yl}acetate (0.047 g, 0.083 mmol) in THF (3 mL) was added 1N NaOH (1.5 mL) and the biphasic mixture was stirred at room temperature for 18 hours. Et$_2$O was added and the separated organic layer siphoned off. The remaining aqueous layer was acidified with 6N HCl and the separated solids were collected by suction and rinsed with water and diisopropyl ether. Drying under high vacuum for 5 hours gave methyl {2-{4-[(anilinocarbonyl)amino]benzyl}-4-chloro-6-[[2-(cyclopentylamino)-2-oxoethyl](methyl)amino]pyrimidin-5-yl}acetate (0.026 g, 56% yield) as a white powder.

$^1$H NMR (300 MHz, DMSO-d$_6$) δ: 1.26-1.82 (m, 8H), 3.08 (s, 3H), 3.69 (s, 2H), 3.81 (s, 2H), 3.98 (s, 2H), 4.00-4.18 (m, 1H), 6.95 (t, J=7 Hz, 1H), 7.20 (d, J=9 Hz, 2H), 7.27 (t, J=8 Hz, 2H), 7.35 (d, J=9 Hz, 2H), 7.43 (d, J=8 Hz, 2H), 7.94 (d, J=7 Hz, 1H), 8.61 (d, J=5 Hz, 2H), 12.76 (bs, 1H).

Molecular weight: 551.05

Mass spectrometry: 551

Melting point: >153 Z° C.

Activity class: B

In a similar manner as described in Example 4-1, compounds in Example 4-2 to 4-4 as shown in Table 4 were synthesized.

TABLE 4

| example # | Structure | MW | Exact Mass | MS | mp (° C.) | Activity class |
|---|---|---|---|---|---|---|
| 4-2 | 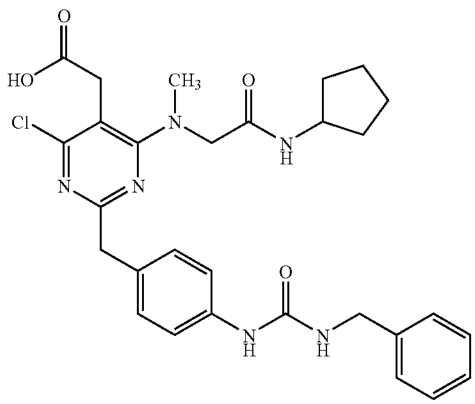 | 565.08 | 564 | 565 | >134 Z | B |
| 4-3 | 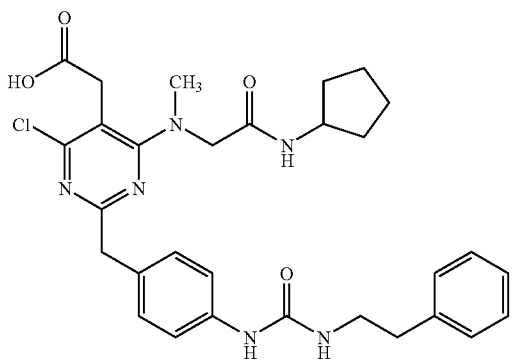 | 579.10 | 578 | 579 | >146 Z | B |
| 4-4 | 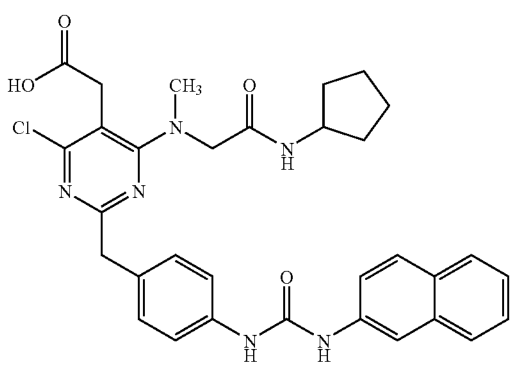 | 601.11 | 600 | 601 | >165 Z | B |
| 4-5 | 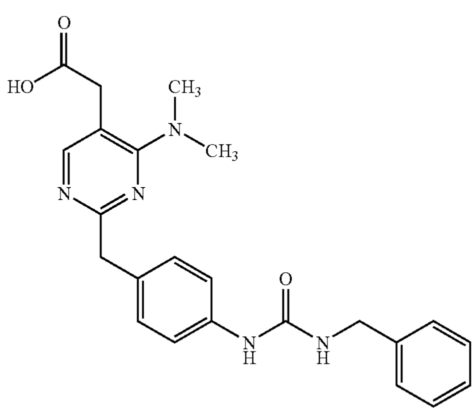 | 419.49 | 220 Z | 419 | 420 | B |

TABLE 4-continued

| example # | Structure | MW | Exact Mass | MS | mp (° C.) | Activity class |
|---|---|---|---|---|---|---|
| 4-6 | 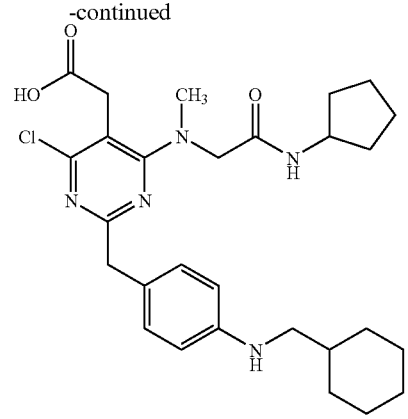 | 433.51 | 88-90 | 433 | 434 | C |

Example 5-1

{4-Chloro-2-{4-[(cyclohexylmethyl)amino]benzyl}-6-[[2-(cyclopentylamino)-2-oxoethyl](methyl)amino]pyrimidin-5-yl}acetic add

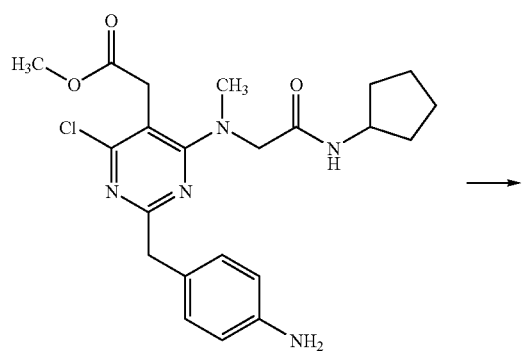

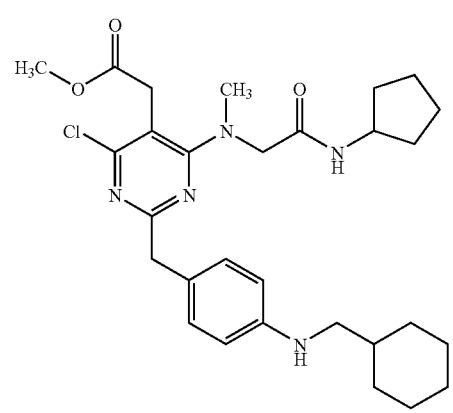

A mixture of methyl {2-(4-aminobenzyl)-4-chloro-6-[[2-(cyclopentylamino)-2-oxoethyl](methyl)amino]pyrimidin-5-yl}acetate (0.150 g, 0.336 mmol), cyclohexanecarbaldehyde (0.042 g, 0.370 mmol), acetic acid (0.019 mL, 0.336 mmol) and sodium triacetoxyborohydride (0.107 g, 0.505 mmol) in 1,2-dichloroethane (3 mL) was stirred overnight at room temperature. Water was then added and the mixture was neutralized with 1N NaOH followed by extraction with dichloromethane. The combined organic extracts was washed sequentially with water and brine, dried over anhydrous MgSO₄, filtered, and concentrated in vacuo. The crude product thus obtained was chromatographed by preparative TLC to give methyl {4-chloro-2-{4-[(cyclohexylmethyl)amino]benzyl}-6-[[2-(cyclopentylamino)-2-oxoethyl](methyl)amino]pyrimidin-5-yl}acetate (0.092 g, 51% yield) as an amorphous solid.

A solution of methyl {4-chloro-2-{4-[(cyclohexylmethyl)amino]benzyl}-6-[[2-(cyclopentyl-amino)-2-oxoethyl](methyl)amino]pyrimidin-5-yl}acetate (0.083 g, 0.15 mmol) in THF (5 mL) was treated with 1N NaOH (2.5 mL) and the resulting mixture was stirred at room temperature for 13 hours. Subsequent to neutralization with 6N HCl, the quenched reaction mixture was evaporated to dryness and the remaining residue dissolved with EtOH. The insoluble inorganic salts were removed by filtration and the filtrate was concentrated in vacuo. The crude product thus obtained was purified with preparative TLC eluting with 15% EtOH in CH$_2$Cl$_2$ to give {4-chloro-2-{4-[(cyclohexylmethyl)amino]benzyl}-6-[[2-(cyclopentylamino)-2-oxoethyl](methyl)amino]-pyrimidin-5-yl}acetic acid (0.023 g, 28% yield) as a clear oil.

$^1$H NMR (300 MHz, CDCl$_3$) δ: 0.85-1.32 (m, 4H), 1.48-1.95 (m, 15H), 2.80-3.05 (m, 7l4), 3.73 (s, 2H), 3.89 (s, 2H), 4.01 (s, 2H), 6.51 (d, J=9 Hz, 2H), 6.69 (d, J=7 Hz, 1H), 7.13 (d, J=7 Hz, 2H)

Molecular weight: 528.10
Mass spectrometry: 528
Activity class: D

In a similar manner as described in Example 5-1, compounds in Example 5-2 to 5-5 as shown in Table 5 were synthesized.

TABLE 5

| example # | Structure | MW | Exact Mass | MS | mp (°C.) | Activity class |
|---|---|---|---|---|---|---|
| 5-2 | 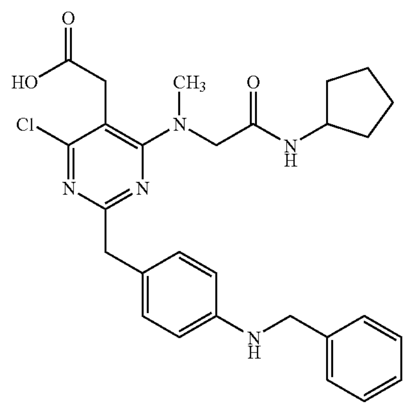 | 522.05 | 521 | 522 | >70 | D |
| 5-3 | 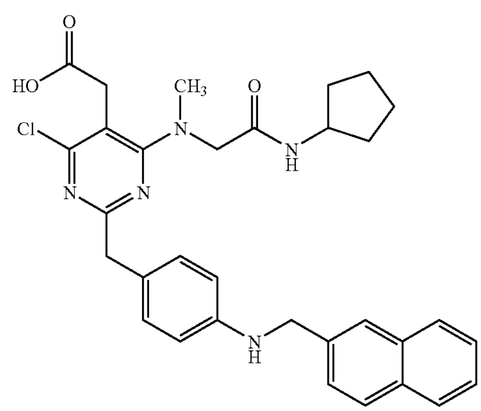 | 572.11 | 571 | 572 | >96 | C |
| 5-4 | 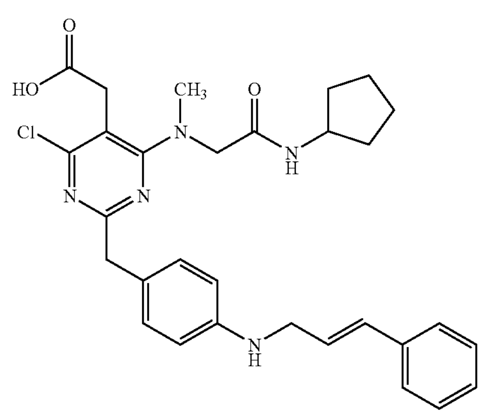 | 548.09 | 547 | 548 | oil | C |

TABLE 5-continued

| example # | Structure | MW | Exact Mass | MS | mp (° C.) | Activity class |
|---|---|---|---|---|---|---|
| 5-5 | 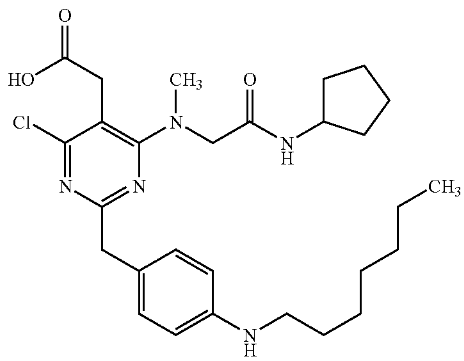 | 530.12 | 529 | 530 | oil | D |

Example 6-1

[4-Chloro-2-{4-[(4-chlorobenzoyl)(methyl)amino]benzyl}-6-(dimethylamino)pyrimidin-5-yl]acetic acid

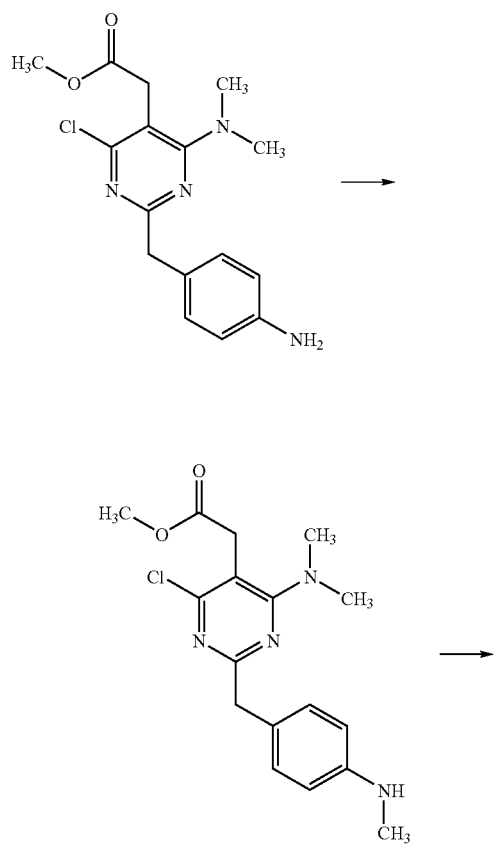

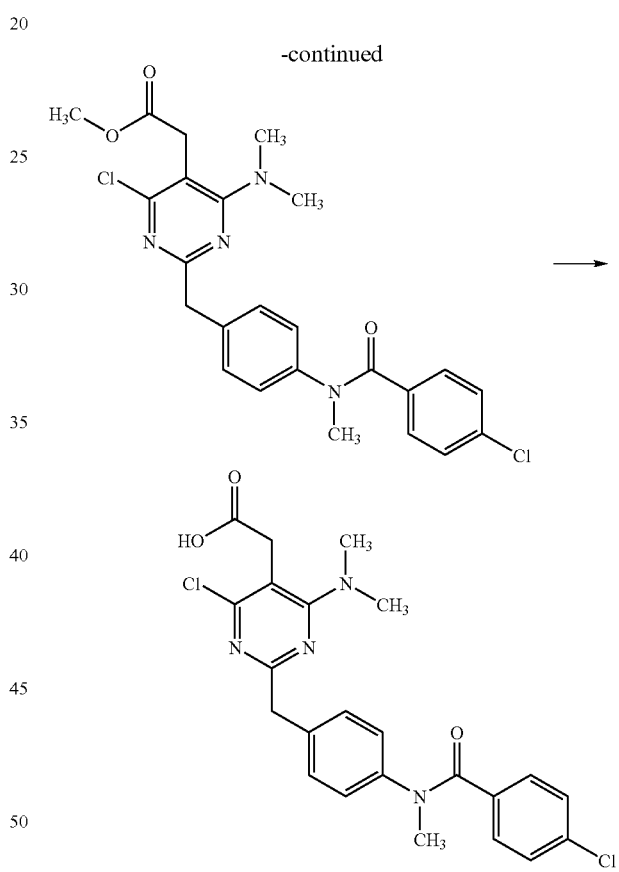

To acetic anhydride (0.48 mL, 5.13 mmol) at 0° C. under Ar atmosphere was added formic acid (0.24 mL, 6.31 mmol) dropwise followed by heating of the mixture at 60° C. for 2 hours. After cooling to room temperature, THF (1 mL) was added followed by a solution of methyl[2-(4-aminobenzyl)-4-chloro-6-(dimethylamino)pyrimidin-5-yl]acetate (0.660 g, 1.97 mmol) in THF (1 ml). This was then stirred for 3 hours and concentrated to dryness. The remaining residue was dissolved in THF and cooled to 0° C. followed by the dropwise addition of borane dimethyl sulfide complex until the vigorous effervescence ceased. The mixture was gently refluxed for 14 hours and then cooled to 0° C. Methanol was added and the mixture was stirred at room temperature for 1 hour followed by the addition of concentrated HCl to pH ~5 and stirring was continued for another 30 minutes. The solvent was evaporated in vacuo, the remaining residue basified with water and 1N NaOH, and the aqueous layer was extracted with Et$_2$O. The combined organic extracts was dried over anhydrous Na$_2$SO$_4$, filtered, and concentrated to dryness to give the crude product which was chromatographed over silica gel eluting with 5% acetone in CH$_2$Cl$_2$ to give methyl {4-chloro-6-(dimethylamino)-2-[4-(methylamino)benzyl]pyrimidin-5-yl}acetate (0.260 g, 38% yield) as a pale yellow oil.

A solution of methyl {4-chloro-6-(dimethylamino)-2-[4-(methylamino)benzyl]pyrimidin-5-yl}acetate (0.080 g, 0.23 mmol), 1-hydroxybenzotriazole (0.043 g, 0.32 mmol), triethylamine (0.11 mL, 0.80 mmol), and 4-chlorobenzoic acid (0.043 g, 0.28 mmol) was treated with WSCI (0.066 g, 0.34 mmol) at room temperature and the reaction mixture was stirred at room temperature for 16 hours. EtOAc was then added and the organic layer was washed sequentially with 0.5N HCl, saturated NaHCO$_3$, and brine, dried over anhydrous Na$_2$SO$_4$, filtered, and concentrated to dryness to give the crude product methyl[4-chloro-2-{4-[(4-chlorobenzoyl)(methyl)amino]benzyl}-6-(dimethylamino)pyrimidin-5-yl]acetate.

This crude methyl[4-chloro-2-{4-[(4-chlorobenzoyl)(methyl)amino]benzyl}-6-(dimethyl-amino)pyrimidin-5-yl]acetate was dissolved in THF (3 mL) and treated with 1N NaOH (2 mL) and stirred at room temperature for 24 hour. Et$_2$O was added and the organic phase was siphoned off. The remaining aqueous layer was acidified with 6N HCl to pH~5 and the separated solids were collected by suction and rinsed with water and diisopropyl ether. Drying under high vacuum at room temperature for 4 hours then gave [4-chloro-2-{4-[(4-chlorobenzoyl)(methyl)amino]-benzyl}-6-(dimethylamino)pyrimidin-5-yl]acetic acid (0.029 g, 27% yield) as a pale yellow powder.

$^1$H NMR (300 MHz, DMSO-d$_6$) δ: 2.50 (s, 3H), 2.98 (s, 6H), 3.65 (s, 2H), 3.88 (s, 21-1), 7.10 (d, J=9 Hz, 2H), 7.20 (d, J=9 Hz, 2H), 7.20-7.27 (bs, 4H), 12.77 (bs, 1H).
Molecular weight: 473.36
Mass spectrometry: 473
Melting point: >68 Z° C.
Activity class: C In a similar manner as described in Example 6-1, compounds in Example 6-2 to 6-3 as shown in Table 6 were synthesized.

TABLE 6

| example # | Structure | MW | Exact Mass | MS | mp (°C.) | Activity class |
|---|---|---|---|---|---|---|
| 6-2 | 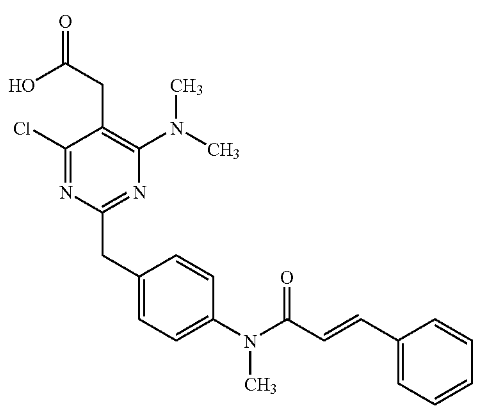 | 464.96 | 464 | 465 | 80 Z | D |
| 6-3 | 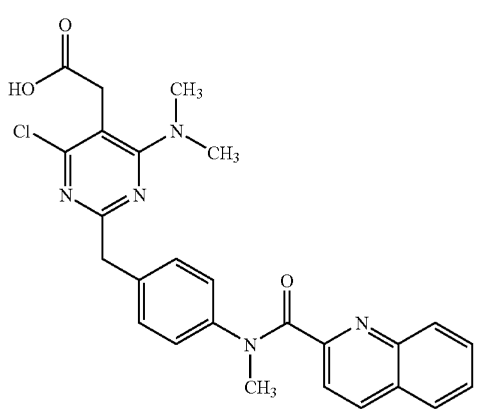 | 489.97 | 489 | 490 | >78 Z | D |

Example 7-1

{4-(Dimethylamino)-6-morpholin-4-yl-2-[4-(2-naphthoylamino)benzyl]pyrimidin-5-yl}acetic acid

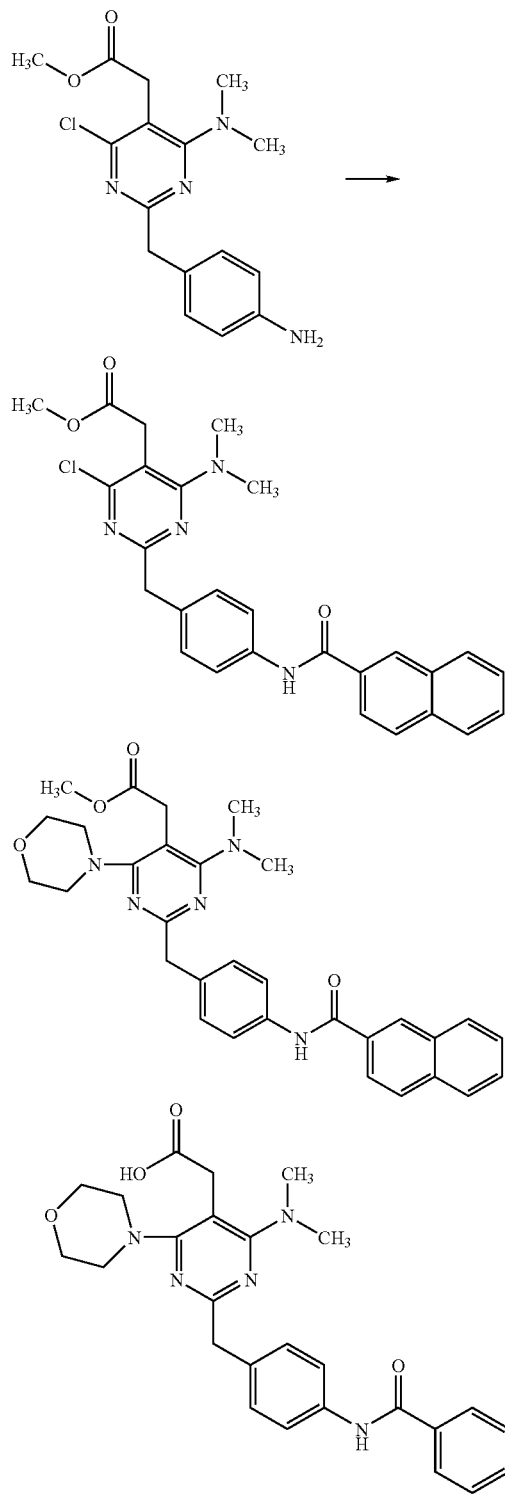

To a mixture of methyl[2-(4-aminobenzyl)-4-chloro-6-(dimethylamino)pyrimidin-5-yl]acetate (0.090 g, 0.30 mmol) and PyBOP (0.187 g, 0.36 mmol) in anhydrous DMF (1 mL) at room temperature was added 2-naphthoic acid (0.062 g, 0.36 mmol). The resulting reaction mixture was stirred at room temperature for 3 hours at which time water was added and the resulting aqueous phase was extracted with EtOAc. The combined organic extracts was sequentially washed with 0.5N HCl, saturated NaHCO₃, and brine, dried over anhydrous MgSO₄, filtered, and concentrated in vacuo to give methyl {4-chloro-6-(dimethylamino)-2-[4-(2-naphthoylamino)benzyl]pyrimidin-5-yl}acetate as a colorless oil.

A mixture of methyl {4-chloro-6-(dimethylamino)-2-[4-(2-naphthoylamino)benzyl]pyrimidin-5-yl}acetate (0.094 g, 0.19 mmol) and morpholine (0.048 mL, 0.55 mmol) in DMPU (2 mL) was heated at 150° C. in a sealed tube for 15 hours. After cooling to room temperature, the reaction mixture was poured into water and extracted with EtOAc. The combined organic extracts was washed sequentially with 1N HCl, saturated NaHCO₃, and brine, dried over anhydrous MgSO₄, filtered, and concentrated in vacuo. The crude product thus obtained was chromatographed over silica gel eluting with 5% EtOAc in CH₂Cl₂ to give methyl {4-(dimethylamino)-6-morpholin-4-yl-2-[4-(2-naphthoylamino)benzyl]pyrimidin-5-yl}acetate (0.096 g, 95% yield) as an oil.

A solution of methyl {4-(dimethylamino)-6-morpholin-4-yl-2-[4-(2-naphthoylamino)benzyl]pyrimidin-5-yl}acetate (0.096 g, 0.18 mmol) in MeOH (2 mL) at room temperature was treated with 1N NaOH (1 mL) and the resulting mixture was heated at 60° C. for 5 hours. After cooling to room temperature, the volatiles were removed under reduced pressure and the remaining aqueous layer was washed with Et₂O and acidified with 1N HCl. The separated solids were collected by suction, rinsed with water, and dried under vacuum to give {4-(dimethylamino)-6-morpholin-4-yl-2-[4-(2-naphthoylamino)benzyl]pyrimidin-5-yl}acetic acid (0.059 g, 64% yield) as a white solid.

$^1$H NMR (300 MHz, DMSO-d₆) δ: 2.90 (s, 6H), 3.17 (m, 4H), 3.43 (s, 3.65 (m, 4H), 3.86 (s, 2H), 7.34 (d, J=9 Hz, 2H), 7.59-7.68 (m, 2H), 7.72 (d, J=9 Hz, 2H), 7.99-8.10 (m, 4H), 8.56 (s, 1H), 10.37 (s, 1H), 12.20 (bs, 1H)

Molecular weight: 525.61
Mass spectrometry: 526
Melting point: 218 Z° C.
Activity class: B

Example 7-2

[4,6-bis(dimethylamino)-2-(4-{[4-(trifluoromethyl)benzoyl]amino}benzyl)pyrimidin-5-yl]acetic acid

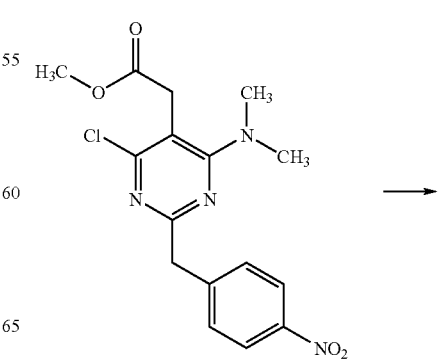

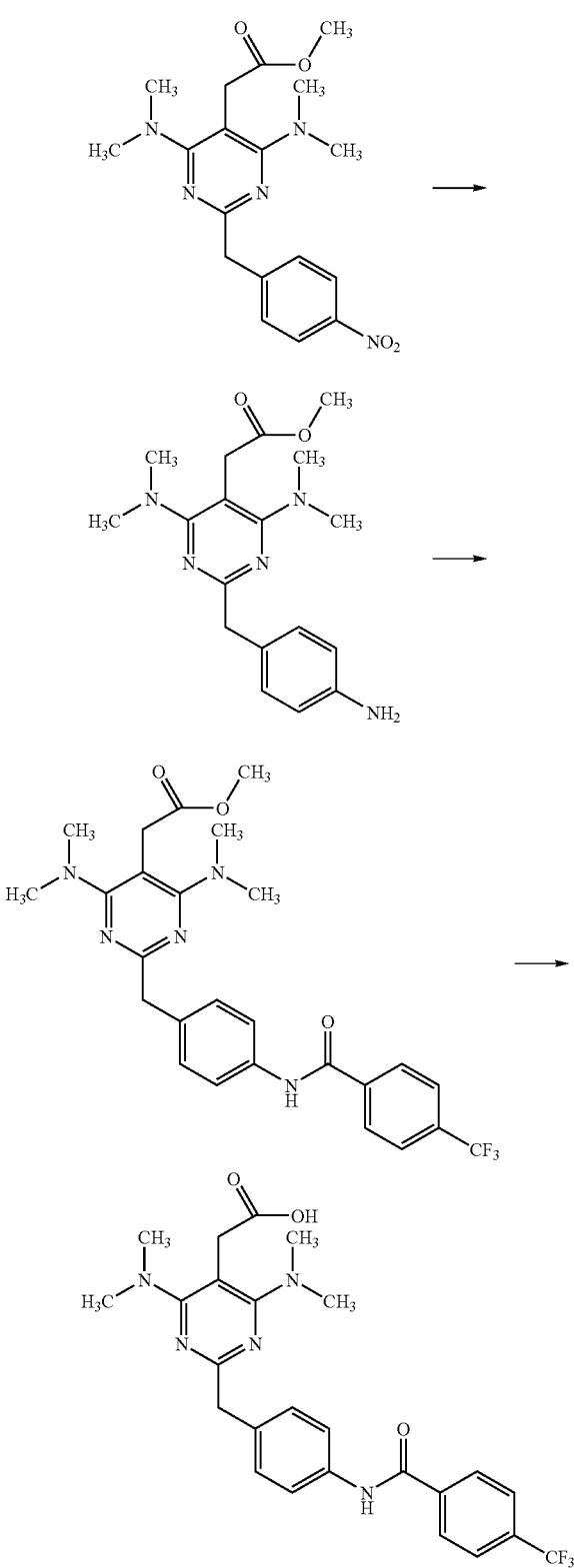

A mixture of methyl[4-chloro-6-(dimethylamino)-2-(4-nitrobenzyl)pyrimidin-5-yl]acetate (7.75 g, 21.25 mmol), dimethylammonium chloride (5.20 g, 63.74 mmol), and N,N-diisopropylethylamine (10.98 g, 84.98 mmol) in DMPU (50 mL) was heated at 150° C. in a sealed tube for 15 hours. After cooling to room temperature, the dark mixture was poured into water and extracted with ethyl acetate. The combined extracts were washed sequentially with water and brine, dried over anhydrous sodium sulfate, filtered, and concentrated to yield the crude product as a dark oil. Chromatographic purification of this crude product over silica gel eluting with 25% ethyl acetate in n-hexane containing 0.1% triethylamine gave methyl[4,6-bis(dimethylamino)-2-(4-nitro-benzyl)pyrimidin-5-yl]acetate (5.44 g, 69%) as a red colored oil.

A solution of methyl[4,6-bis(dimethylamino)-2-(4-nitrobenzyl)pyrimidin-5-yl]acetate (5.00 g, 13.39 mmol) in methanol (150 mL) was treated with palladium on charcoal (10% Pd, 0.50 g) and the resulting black suspension was stirred under a blanket of hydrogen gas at room temperature for 10 hours. The reaction mixture was filtered through a pad of Celite and the filtrate was concentrated in vacuo to give methyl[2-(4-aminobenzyl)-4,6-bis(dimethylamino)pyrimidin-5-yl]acetate (4.53 g, 98%).

A solution of methyl[2-(4-aminobenzyl)-4,6-bis(dimethylamino)pyrimidin-5-yl]acetate (4.00 g, 11.65 mmol) in dichloromethane (120 mL) was treated with 4-trifluoromethylbenzoyl chloride (2.92 g, 13.98 mmol) and triethylamine (3.54 g, 34.94 mmol). After stirring for 1 hour at room temperature, the reaction mixture was partitioned between water and chloroform and the aqueous layer was extracted with chloroform. The combined organic extracts were washed with water and brine, dried over anhydrous sodium sulfate, filtered, and concentrated in vacuo to give the crude product as a yellow colored solid which was recrystallized from methanol to give methyl[4,6-bis(dimethylamino)-2-(4-{[4-(trifluoromethyl)benzoyl]amino}benzyl)pyrimidin-5-yl]acetate (4.34 g, 73%) as a white solid.

A solution of methyl[4,6-bis(dimethylamino)-2-(4-{[4-(trifluoromethyl)benzoyl]amino}-benzyl)pyrimidin-5-yl]acetate (4.34 g, 8.42 mmol) in 20% tetrahydrofuran in methanol (100 mL) was treated with 1N sodium hydroxide solution (25 mL). The resulting mixture was heated at refluxing temperature for 5 hours and then the volatiles were removed by rotary evaporation under vacuum. The remaining aqueous solution was washed with diethyl ether and then neutralized with 1N hydrochloric acid at 0° C. The separated precipitate was collected by suction and rinsed with cold water. Recrystallization from methanol then gave [4,6-bis(dimethylamino)-2-(4-{[4-(trifluoromethyl)benzoyl]amino}benzyl)pyrimidin-5-yl]acetic acid (3.86 g, 81%) as colorless needles.

$^1$H NMR (500 MHz, DMSO-d6): δ 3.29 (s, 12H), 3.44 (s, 2H), 3.83 (s, 2H), 7.33 (d, J=8.2 Hz, 2H), 7.66 (d, J=8.2 Hz, 2H), 7.90 (d, J=8.2 Hz, 2H), 8.13 (d, J=8.2 Hz, 2H), 10.28 (s, 1H), 12.02 (s, 1H).

Molecular weight: 501.51

Mass spectrometry: 502 (M+H)$^+$

Melting point: 200 Z° C.

Activity class: A

In a similar manner as described in Example 7-1 or Example 7-2, compounds in Example 7-3 to 7-30 as shown in Table 7 were synthesized.

Table 7

| example # | Structure | MW | Exact Mass | MS | mp (° C) | Activity class |
|---|---|---|---|---|---|---|
| 7-3 | 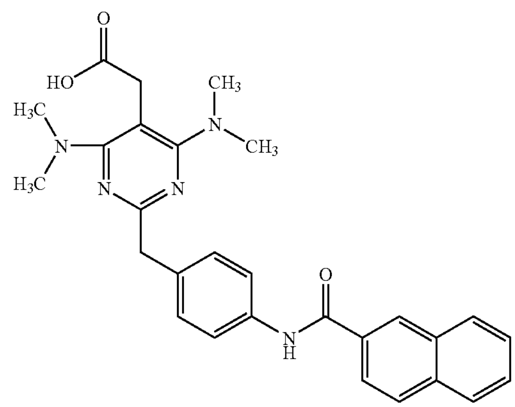 | 483.58 | 483 | 484 | 200 Z | B |
| 7-4 | 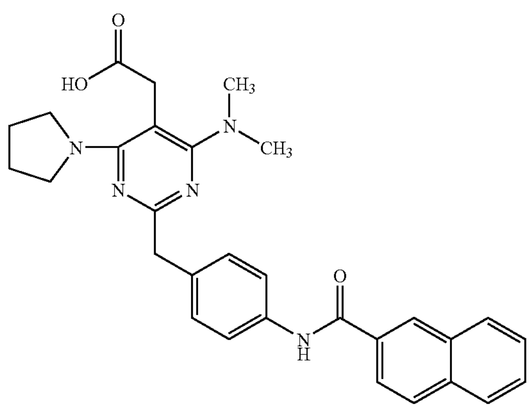 | 509.61 | 509 | 510 | 154 Z | B |
| 7-5 | 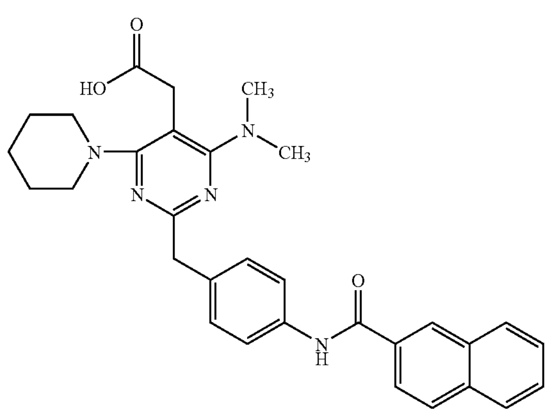 | 523.64 | 523 | 524 | 149 Z | B |

Table 7-continued

| example # | Structure | MW | Exact Mass | MS | mp (° C) | Activity class |
|---|---|---|---|---|---|---|
| 7-6 | 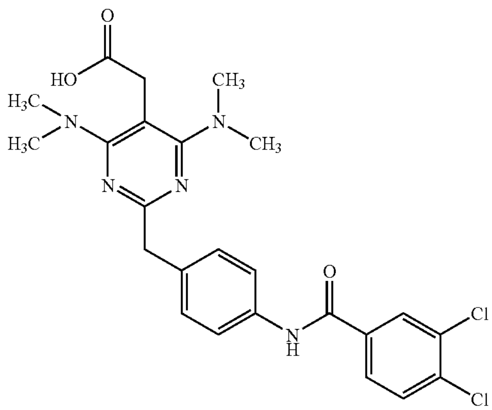 | 502.40 | 501 | 502 | 193 Z | A |
| 7-7 | 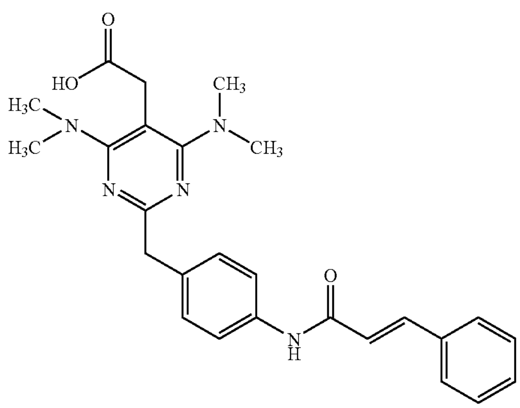 | 459.55 | 459 | 460 | 172 Z | A |
| 7-8 | 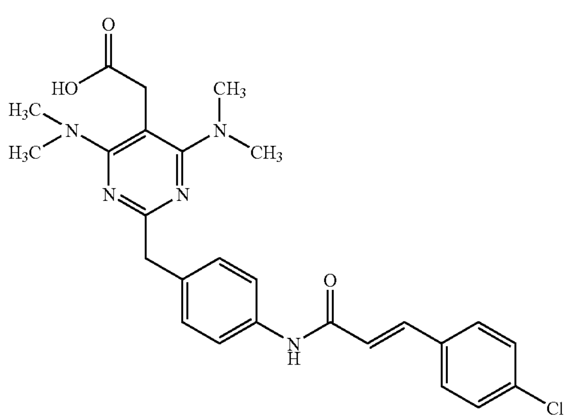 | 494.00 | 493 | 494 | 162 | A |

Table 7-continued
| example # | Structure | MW | Exact Mass | MS | mp (° C) | Activity class |
|---|---|---|---|---|---|---|
| 7-9 | 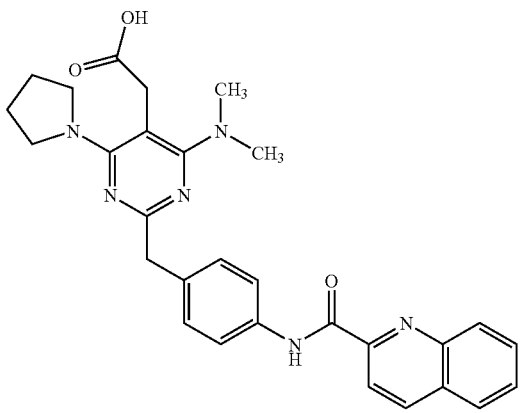 | 510.60 | 510 | 511 | 131-133 | C |
| 7-10 | 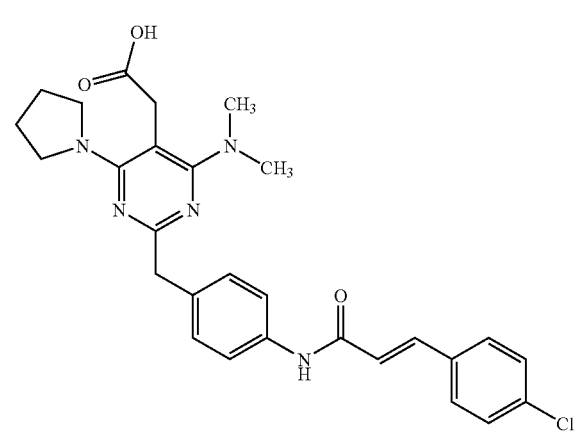 | 520.04 | 520 | 521 | 146-149 | A |
| 7-11 | 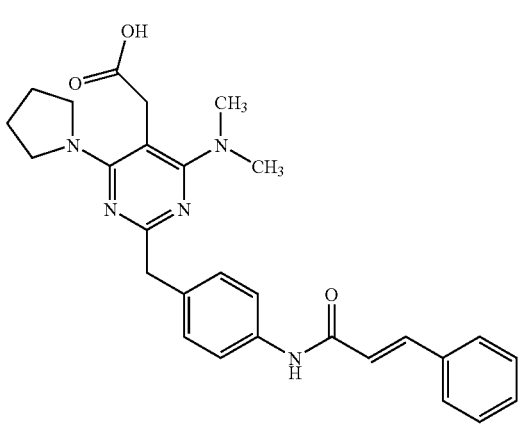 | 485.59 | 485 | 486 | 151-153 | B |

Table 7-continued
| example # | Structure | MW | Exact Mass | MS | mp (° C) | Activity class |
|---|---|---|---|---|---|---|
| 7-12 | 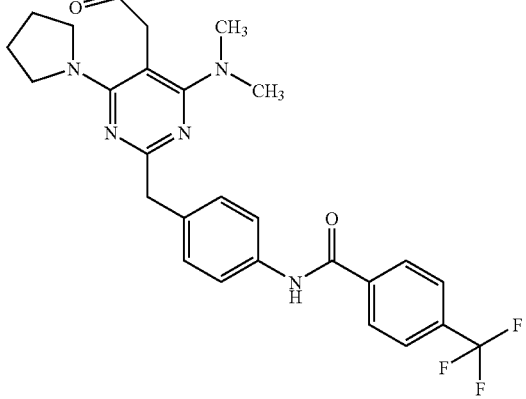 | 527.55 | 527 | 528 | 144-147 | B |
| 7-13 | 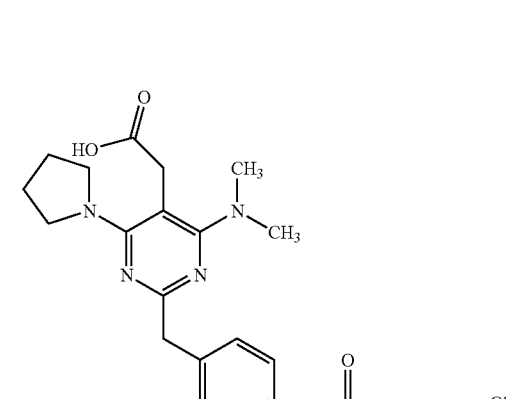 | 528.44 | 528 | 529 | 150-152 | C |
| 7-14 | 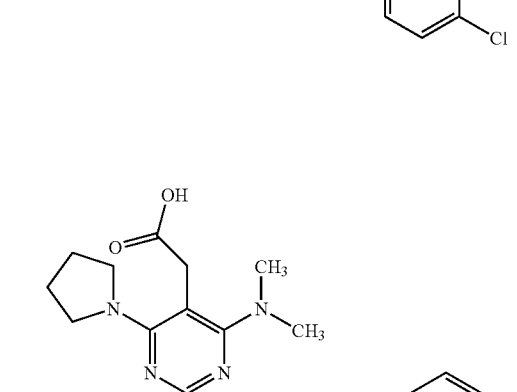 | 535.65 | 535 | 536 | 132-134 | D |

Table 7-continued

| example # | Structure | MW | Exact Mass | MS | mp (° C) | Activity class |
|---|---|---|---|---|---|---|
| 7-15 | 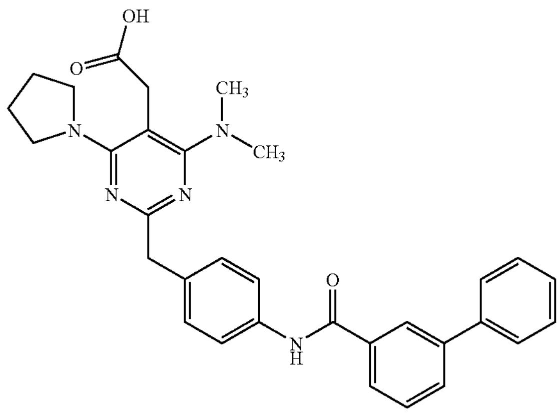 | 535.65 | 535 | 536 | 147-179 | B |
| 7-16 | 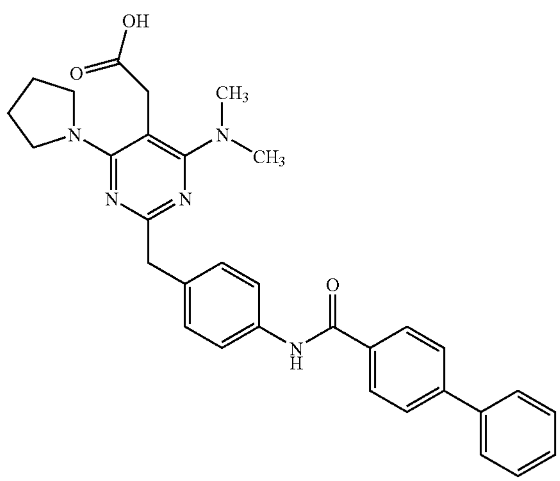 | 535.65 | 535 | 536 | 224-226 | B |
| 7-17 | 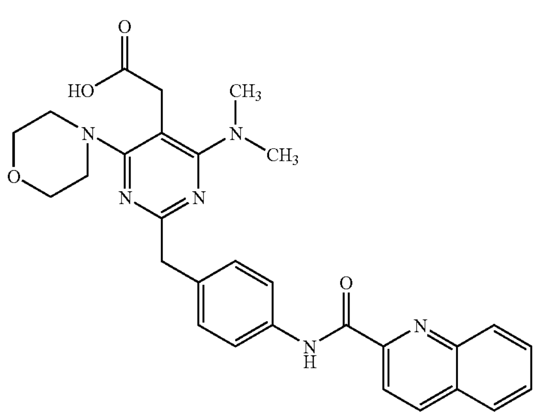 | 526.60 | 526 | 527 | 205-207 | D |

| example # | Structure | MW | Exact Mass | MS | mp (° C) | Activity class |
|---|---|---|---|---|---|---|
| 7-18 | 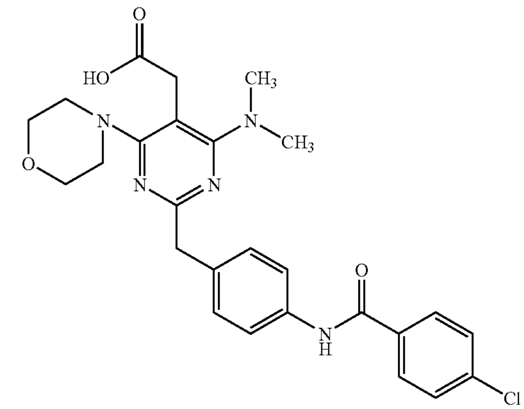 | 510.00 | 509 | 510 | 216-218 z | C |
| 7-19 | 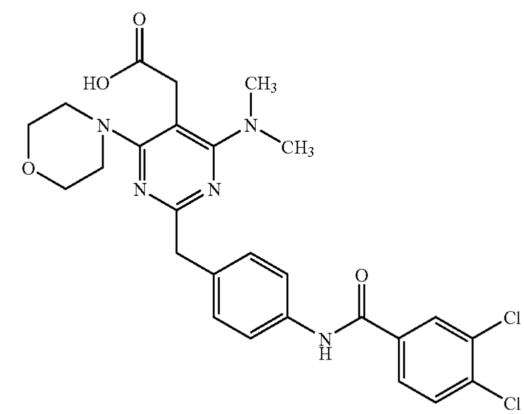 | 544.44 | 543 | 544 | 196-198 | B |
| 7-20 | 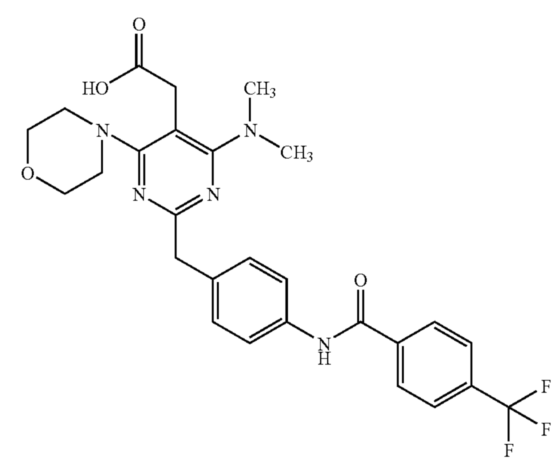 | 543.55 | 543 | 544 | 212-213 z | B |

Table 7-continued

| example # | Structure | MW | Exact Mass | MS | mp (° C) | Activity class |
|---|---|---|---|---|---|---|
| 7-21 | 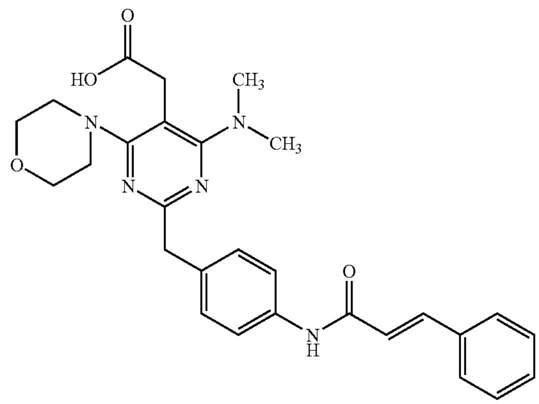 | 501.59 | 501 | 502 | 129-132 | B |
| 7-22 | 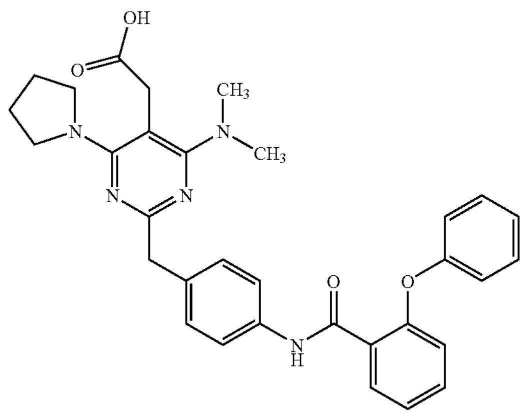 | 551.65 | 551 | 552 | 192-194 | D |
| 7-23 | 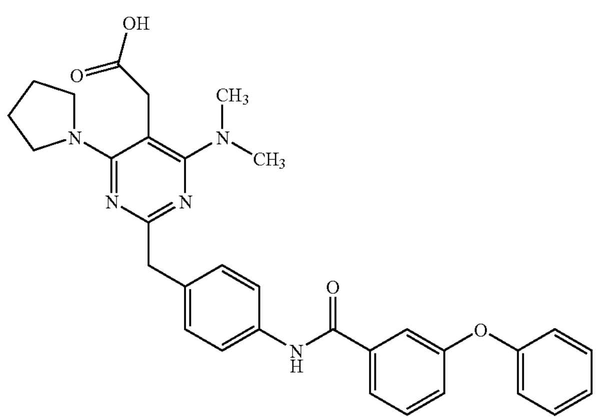 | 551.65 | 551 | 552 | 123-125 | B |

Table 7-continued

| example # | Structure | MW | Exact Mass | MS | mp (° C) | Activity class |
|---|---|---|---|---|---|---|
| 7-24 | 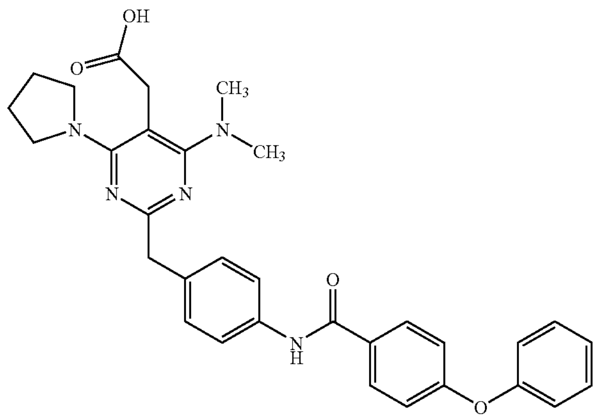 | 551.65 | 551 | 552 | 137-140 | A |
| 7-25 | 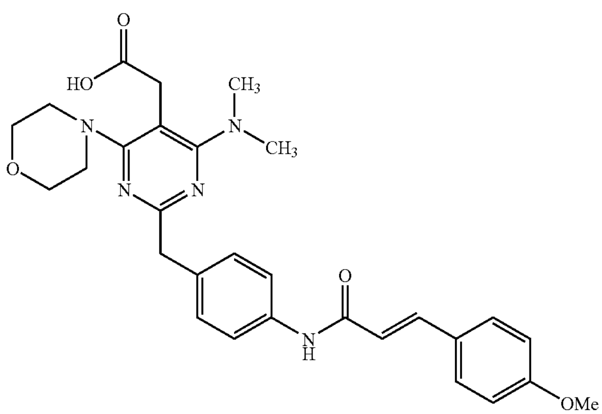 | 531.62 | 531 | 532 | 192-195 z | A |
| 7-26 | 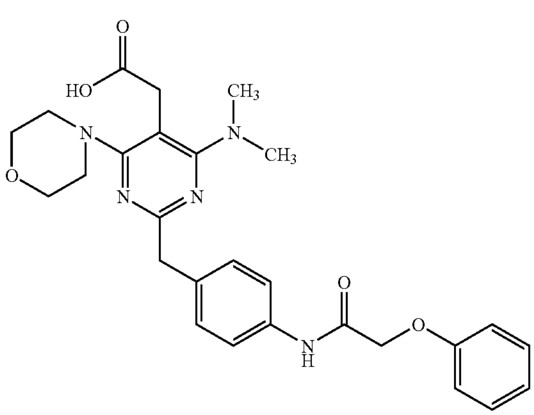 | 505.58 | 505 | 506 | 172-175 | D |

Table 7-continued

| example # | Structure | MW | Exact Mass | MS | mp (° C) | Activity class |
|---|---|---|---|---|---|---|
| 7-27 | 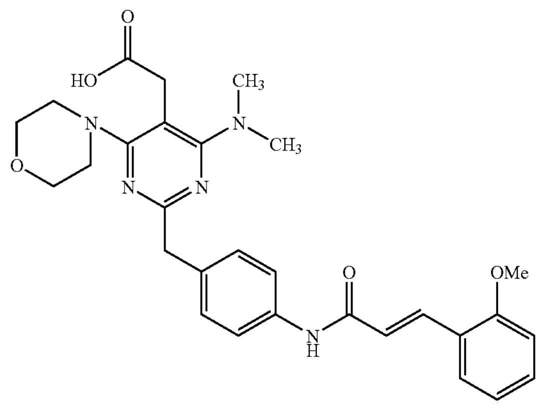 | 531.62 | 531 | 532 | 125-128 | A |
| 7-28 | 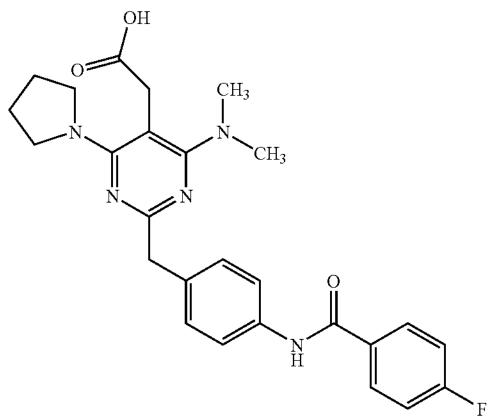 | 477.54 | 477 | 478 | 132-135 | C |
| 7-29 | 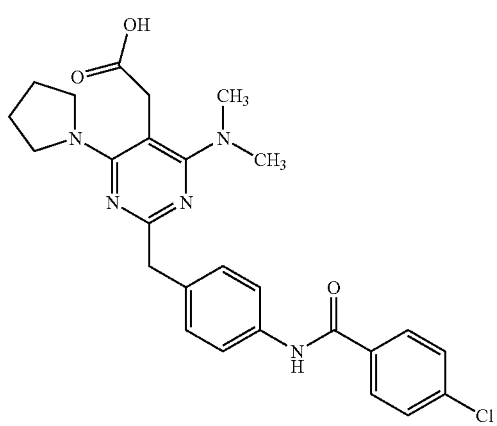 | 494.00 | 493 | 494 | 140-142 | B |

Table 7-continued

| example # | Structure | MW | Exact Mass | MS | mp (° C) | Activity class |
|---|---|---|---|---|---|---|
| 7-30 | 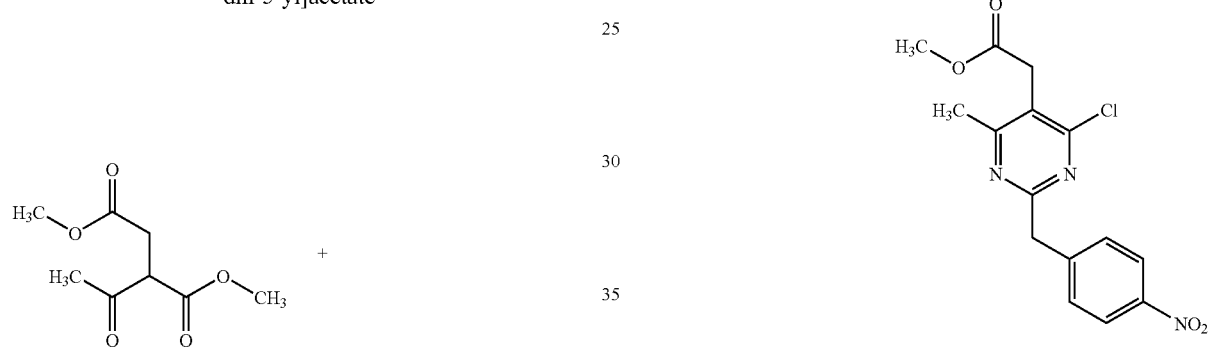 | 493.54 | 493 | 494 | 197-198 | C |

Methyl[4-chloro-6-methyl-2-(4-nitrobenzyl)pyrimidin-5-yl]acetate

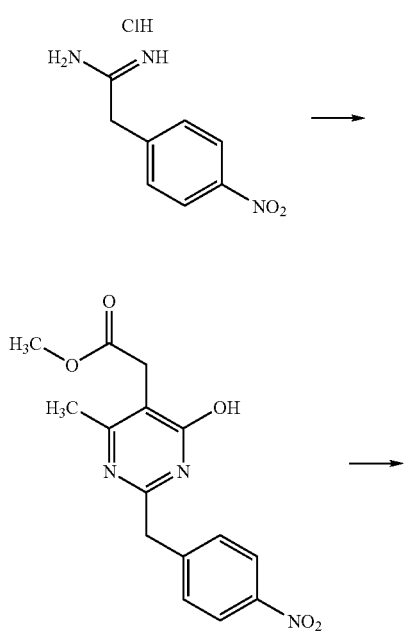

A mixture of 2-(4-nitrophenyl)ethanimidamide hydrochloride (0.22 g, 1.0 mmol), dimethyl acetyl-succinate (0.19 g, 1.0 mmol), and sodium methoxide (0.07 g, 1.3 mmol) in MeOH (10 mL) was refluxed for 15 hours. After cooling to room temperature, the separated solids were collected by suction and added to a pre-formed solution of thionyl chloride (0.65 mL, 8.9 mmol) in MeOH (7.5 mL). The resulting mixture was refluxed for 16 hours and then cooled to room temperature. Acetone was added and the precipitated solids were collected by suction, rinsed with acetone and dried under high vacuum for 4 hours to give methyl[4-hydroxy-6-methyl-2-(4-nitrobenzyl)-pyrimidin-5-yl]acetate (0.12 g, 38% yield) as a white solid.

A solution of methyl[4-hydroxy-6-methyl-2-(4-nitrobenzyl)pyrimidin-5-yl]acetate (1.59 g, 5.0 mmol) and N,N-dimethylaniline (0.56 mL, 4.4 mmol) in FOCl) (2.33 mL, 25 mmol) was refluxed for 14 hours. After cooling to room temperature, the reaction mixture was poured into ice-cold saturated $K_2CO_3$. The resulting aqueous layer was extracted with EtOAc and the combined organic extracts was washed with brine, dried over anhydrous $MgSO_4$, filtered, and concentrated in vacuo. The crude product thus obtained was chromatographed over silica gel eluting with 20% EtOAc in n-hexane to afford methyl[4-chloro-6-methyl-2-(4-nitrobenzyl)pyrimidin-5-yl]acetate (0.54 g, 32% yield) as a white powder.

Example 8-1

{4-Methyl-2-[4-(2-naphthoylamino)benzyl]-6-pyrrolidin-1-ylpyrimidin-5-yl}acetic acid

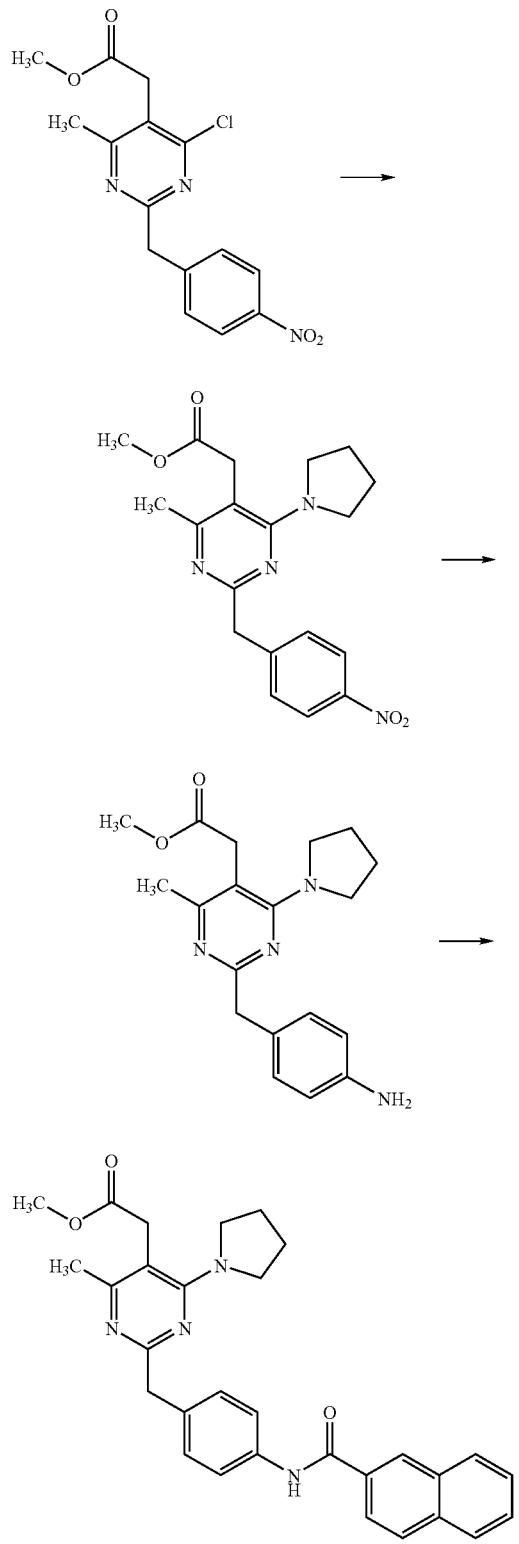

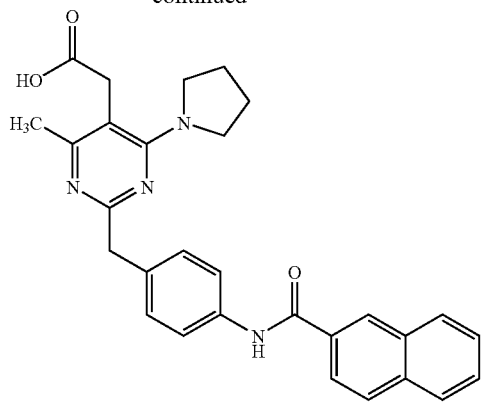

A solution of methyl[4-chloro-6-methyl-2-(4-nitrobenzyl) pyrimidin-5-yl]acetate (0.45 g, 1.3 mmol) and pyrrolidine (0.13 mL, 1.6 mmol) in DMF (10 mL) at room temperature was treated with triethylamine (0.22 mL, 1.6 mmol) and the resulting mixture was stirred at 85° C. for 13 hours. After cooling to room temperature, the reaction mixture was poured into water and extracted with EtOAc. The combined organic extracts was washed with saturated $NaHCO_3$ and brine, dried over anhydrous $MgSO_4$, filtered, and concentrated in vacuo. The crude product thus obtained was chromatographed over silica gel eluting with 50% EtOAc in $CH_2Cl_2$ to give methyl [4-methyl-2-(4-nitrobenzyl)-6-pyrrolidin-1-ylpyrimidin-5-yl]acetate (0.40 g, 80% yield) as a white powder.

To a solution of methyl[4-methyl-2-(4-nitrobenzyl)-6-pyrrolidin-1-ylpyrimidin-5-yl]acetate (0.074 g, 0.20 mmol) in anhydrous THF (2 mL) was added Pd/C (10% Pd, 0.050 g) and the resulting black suspension was stirred under an atmosphere of hydrogen. After 1 hour; the reaction mixture was filtered through Celite and the filtrate was concentrated in vacuo to give methyl[2-(4-aminobenzyl)-4-methyl-6-pyrrolidin-1-ylpyrimidin-5-yl]acetate.

A solution of methyl[2-(4-aminobenzyl)-4-methyl-6-pyrrolidin-1-ylpyrimidin-5-yl]acetate (0.034 g, 0.10 mmol) in THF (1 mL) at room temperature was treated with PyBOP (0.052 g, 0.10 mmol), 2-naphthoic acid (0.019 g, 0.11 mmol), and N,N-diisopropylethylamine (0.017 mL, 0.10 mmol). After stirring at room temperature for 17 hours, the reaction mixture was poured into water and extracted with EtOAc. The combined organic extracts was dried over anhydrous $MgSO_4$, filtered, and concentrated in vacuo. The remaining residue was chromatographed over silica gel eluting with 60% EtOAc in $CH_2Cl_2$ to give methyl {4-methyl-2-[4-(2-naphthoylamino)benzyl]-6-pyrrolidin-1-ylpyrimidin-5-yl}acetate (0.018 g, 36% yield) as a yellow oil.

A solution of methyl {4-methyl-2-[4-(2-naphthoylamino) benzyl]-6-pyrrolidin-1-ylpyrimidin-5-yl}acetate (0.018 g, 0.04 mmol) in THF (1 mL) at room temperature was treated with 1N NaOH (0.5 mL) and the resulting biphasic mixture was stirred at 60° C. for 13 hours. After cooling to room temperature, $Et_2O$ was added and the organic layer siphoned off The remaining aqueous layer was acidified with 6N HCl and the separated solids were collected by suction, rinsed with water, and dried under high vacuum for 4 hours to give (4-methyl-2-[4-(2-naphthoyl-amino)benzyl]-6-pyrrolidin-1-ylpyrimidin-5-yl)acetic acid (0.006 g, 37% yield) as a white solid.

$^1$H NMR (300 MHz, DMSO-$d_6$) δ: 1.86 (bs, 4H), 2.29 (s, 3H), 3.60 (bs, 4H), 3.71 (s, 2H), 3.94 (s, 2H), 7.35 (d, J=8 Hz,

2H), 7.60-7.67 (m, 2H), 7.75 (d, J=8 Hz, 2H), 8.00-8.10 (m, 4H), 8.56 (s, 1H), 10.40 (s, 1H), 12.73 (bs, 1H)
Molecular weight: 480.57
Mass spectrometry: 481
Melting point: 184 Z° C.

Activity class: A

In a similar manner as described in Example 8-1, compounds in Example 8-2 to 8-11 as shown in Table 8 were synthesized.

TABLE 8

| example # | Structure | MW | Exact Mass | MS | mp (° C.) | Activity class |
|---|---|---|---|---|---|---|
| 8-2 | 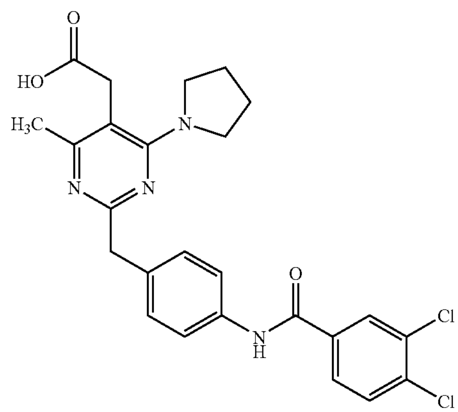 | 499.40 | 498 | 499 | 196 Z | A |
| 8-3 | 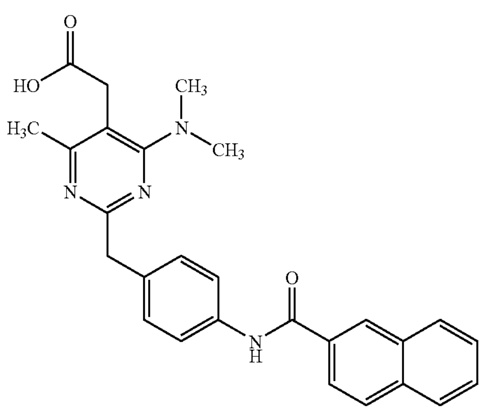 | 454.53 | 454 | 455 | 207 Z | A |
| 8-4 | 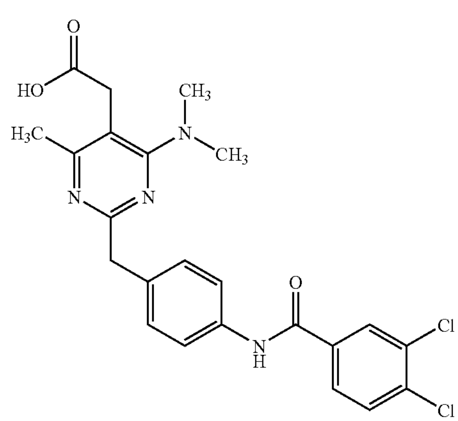 | 473.36 | 472 | 473 | 197 Z | A |

TABLE 8-continued

| example # | Structure | MW | Exact Mass | MS | mp (° C.) | Activity class |
|---|---|---|---|---|---|---|
| 8-5 | 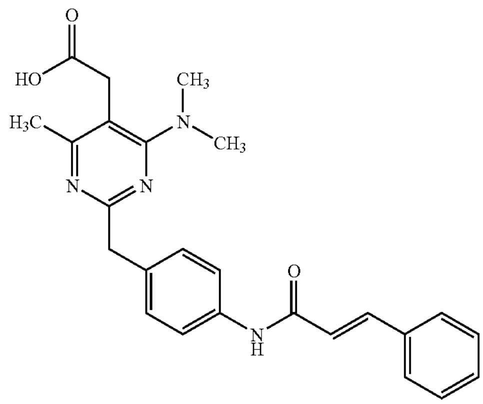 | 430.51 | 430 | 431 | 197 Z | A |
| 8-6 | 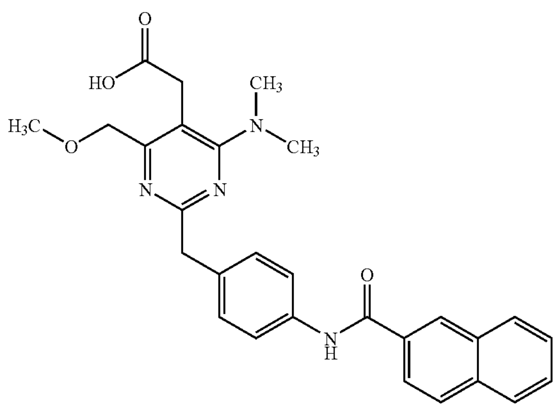 | 484.56 | 484 | 485 | 128-131 | A |
| 8-7 | 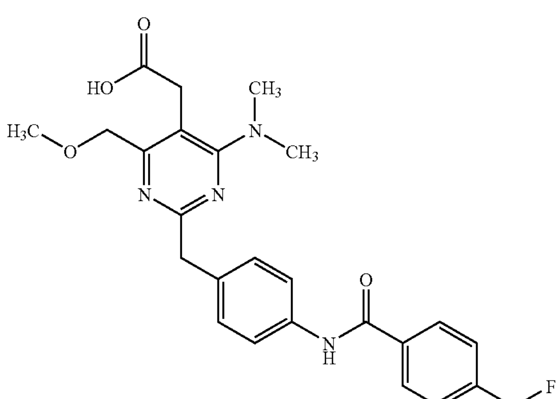 | 502.50 | 502 | 503 | 126-128 | A |

TABLE 8-continued

| example # | Structure | MW | Exact Mass | MS | mp (° C.) | Activity class |
|---|---|---|---|---|---|---|
| 8-8 | 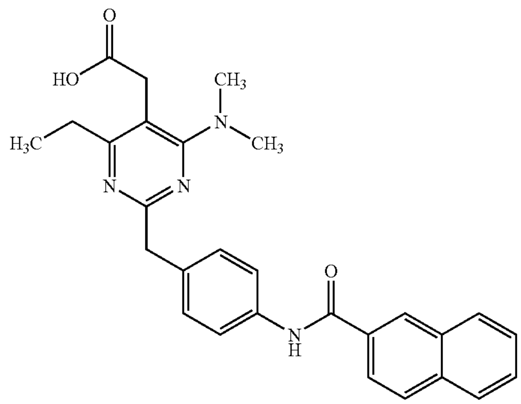 | 468.56 | 468 | 469 | 148-150 | A |
| 8-9 | 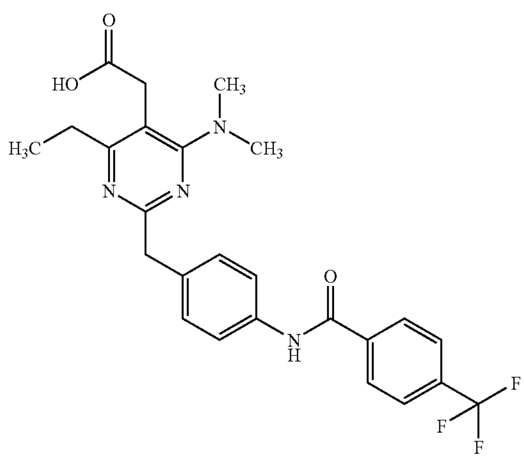 | 486.50 | 486 | 487 | 153-155 | A |
| 8-10 | 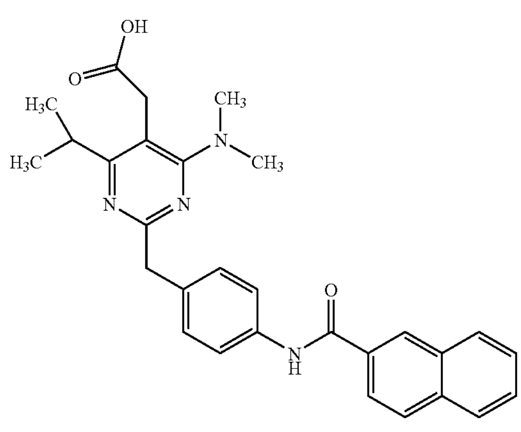 | 482.59 | 482 | 483 | 158-160 | B |

TABLE 8-continued

| example # | Structure | MW | Exact Mass | MS | mp (° C.) | Activity class |
|---|---|---|---|---|---|---|
| 8-11 | 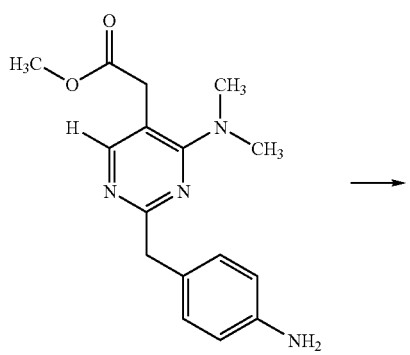 | 500.53 | 500 | 501 | 145-148 | B |

Example 9-1

[2-(4-{[(Benzyloxy)carbonyl]amino}benzyl)-4-(dimethylamino)pyrimidin-5-yl]acetic acid

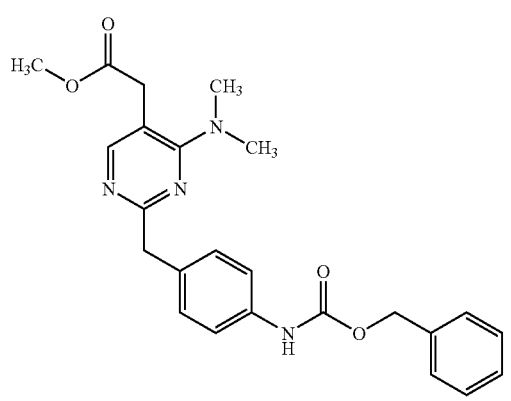

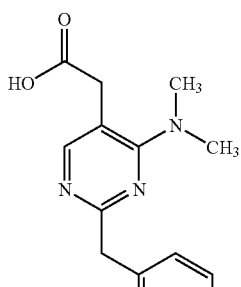

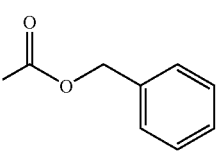

To a mixture of methyl[2-(4-aminobenzyl)-4-(dimethylamino)pyrimidin-5-yl]acetate (1.50 g, 4.99 mmol) in pyridine (1.21 mL) and dichloromethane (20 mL) was added benzyl chloroformate (1.07 mL, 7.49 mmol). After stirring for 14 hours at room temperature, the reaction mixture was concentrated under reduced pressure. The remaining residue was chromatographed on silica gel (NH silica gel, hexane/ethyl acetate 2:1) to give methyl[2-(4-{[(benzyloxy)carbonyl]amino}-benzyl)-4-(dimethylamino)pyrimidin-5-yl]acetate (1.99 g, 92%).

To a mixture of methyl[2-(4-{[(benzyloxy)carbonyl]amino}benzyl)-4-(dimethylamino)pyrimidin-5-yl]acetate (1.51 g, 3.48 mmol) in tetrahydrofuran (8 mL) and methanol (15 mL) was added 1N NaOH aq. (5 mL). The reaction mixture was stirred for 20 hours at room temperature and concentrated under reduced pressure. The residue was neutralized with 1N hydrochloric acid and concentrated under reduced pressure. This residue was dissolved with chloroform/methanol (10:1) and the insolubles were removed by filtration. The filtrate was concentrated under reduced pressure. The residual solid was recrystallized with acetonitrile/ethanol (10:1) to give [2-(4-{[(benzyloxy)carbonyl]amino}benzyl)-4-(dimethylamino)pyrimidin-5-yl]acetic acid (1.14 g, 78%) as a white solid.

$^1$H NMR (500 MHz, DMSO-d6): δ=3.02 (s, 6H), 3.62 (s, 2H), 3.86 (s, 2H), 5.13 (s, 2H), 7.21 (d, J=8.5 Hz, 2H), 7.31-7.42 (m, 7H), 7.94 (s, 1H), 9.64 (s, 1H), 12.5 (s, 1H).

Molecular weight: 420.47
Mass spectrometry: 421 (M+H)$^+$
Melting point: 101-104° C.
Activity class: B Example 9-2

{4-(dimethylamino)-2-[4-({[(4-fluorobenzyl)oxy]carbonyl}amino)benzyl]pyrimidin-5-yl}acetic acid

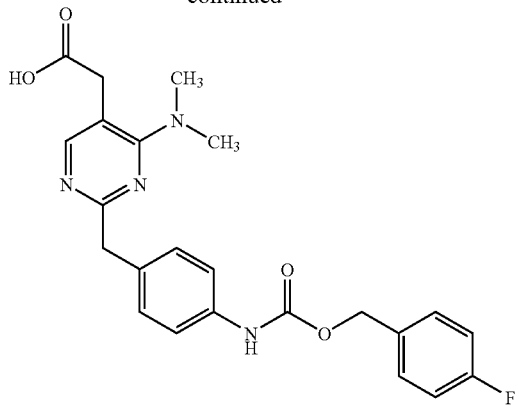

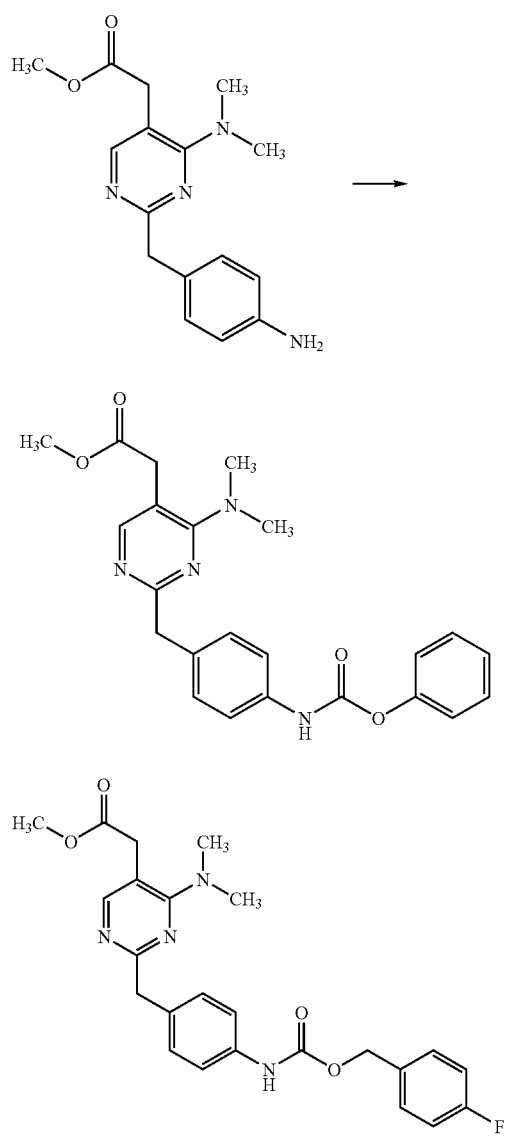

To a mixture of methyl[2-(4-aminobenzyl)-4-(dimethylamino)pyrimidin-5-yl]acetate (400 mg, 1.33 mmol) in pyridine (0.43 mL) and dichloromethane (5 mL) was added phenyl chloroformate (0.25 mL, 2.00 mmol) at 0° C. The reaction mixture was stirred for 15 hours at room temperature at which time it was concentrated under reduced pressure. The crude phenyl carbamate product (i.e. methyl (4-(dimethylamino)-2-{4-[(phenoxycarbonyl)amino]benzyl}pyrimidin-5-yl)acetate) was employed in the next reaction without further purification.

A mixture of methyl (4-(dimethylamino)-2-{4-[(phenoxycarbonyl)amino]benzyl}pyrimidin-5-yl)acetate (100 mg, 0.24 mmol) and 4-fluorobenzyl alcohol (60 mg, 0.48 mmol) in N,N-diisopropylethylamine (0.17 mL, 0.95 mmol) and tetrahydrofuran (2 mL) was refluxed for 24 hours. After cooling to room temperature, the reaction mixture was concentrated under reduced pressure and the remaining residue was purified by preparative TLC chloroform/methanol 30:1) to give methyl {4-(dimethylamino)-2-[4-({[(4-fluorobenzyl)oxy]carbonyl}amino)benzyl]pyrimidin-5-yl}acetate (45 mg, 42%).

To a mixture of methyl {4-(dimethylamino)-2-[4-({[(4-fluorobenzyl)oxy]carbonyl}amino)benzyl]-pyrimidin-5-yl}acetate (45 mg, 0.10 mmol) in tetrahydrofuran (0.5 mL) and methanol (0.5 mL) was added 1N NaOH aq. (0.2 mL). The reaction mixture was stirred for 20 hours at room temperature and concentrated under reduced pressure. The residue was neutralized with 1N hydrochloric acid and concentrated under reduced pressure. This residue was dissolved with chloroform/methanol (10:1) and the insoluble was removed by filtration. The filtrate was concentrated under reduced pressure to give {4-(dimethylamino)-2-[4-({[(4-fluorobenzyl)oxy]carbonyl}amino)benzyl]pyrimidin-5-yl}acetic acid (35 mg, 80%) as a pale yellow solid.

$^1$H NMR (500 MHz, DMSO-d6): δ=3.06 (s, 6H), 3.66 (s, 2H), 3.88 (s, 2H), 5.11 (s, 2H), 7.22 (d, J=8.5 Hz, 4H), 7.36 (d, J=8.5 Hz, 2H), 7.47 (dd, J=8.5, 8.5 Hz, 2H), 7.96 (s, 1H), 9.68 (s, 1H), 12.6 (s, 1H).

Molecular weight: 438.46
Mass spectrometry: 439 (M+H)$^+$
Melting point: 95-97° C.
Activity class: A In a similar manner as described in Example 9-1 or Example 9-2, compounds in Example 9-3 to 9-8 as shown in Table 9 were synthesized.

| example # | Structure | MW | Exact Mass | MS | mp (° C.) | Activity class |
|---|---|---|---|---|---|---|
| 9-3 | 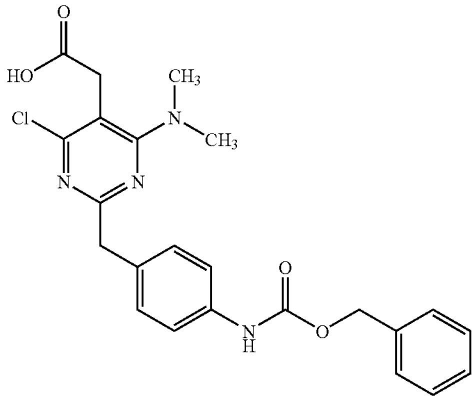 | 454.92 | 454 | 455 | 88-91 | A |
| 9-4 | 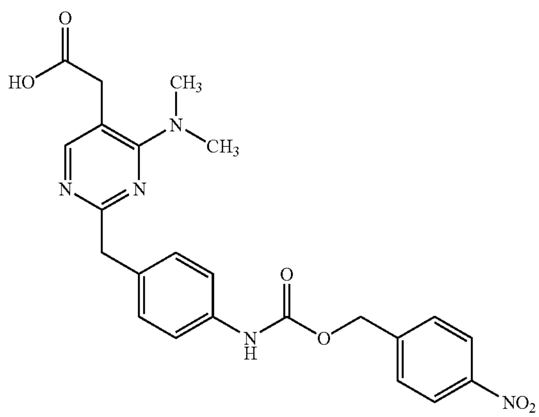 | 465.47 | 465 | 466 | 145 Z | B |
| 9-5 | 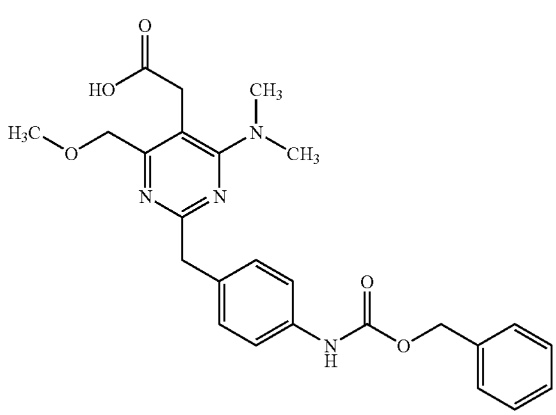 | 464.53 | 464 | 465 | 88-90 | D |

| example # | Structure | MW | Exact Mass | MS | mp (°C.) | Activity class |
|---|---|---|---|---|---|---|
| 9-6 | 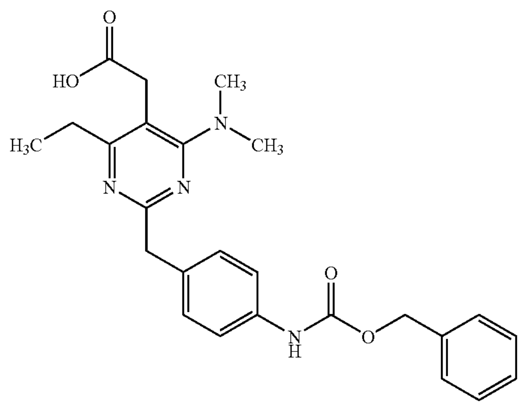 | 448.53 | 448 | 449 | 120-123 | D |
| 9-7 | 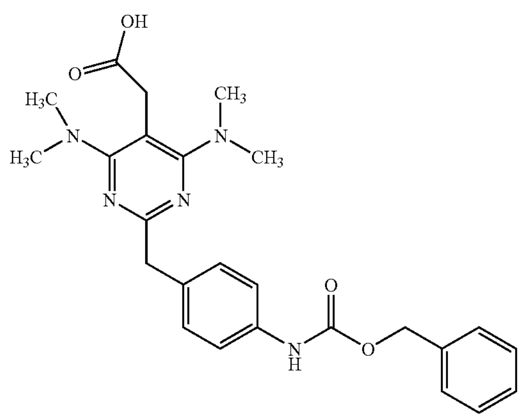 | 463.53 | 463 | 464 | 100 | A |
| 9-8 | 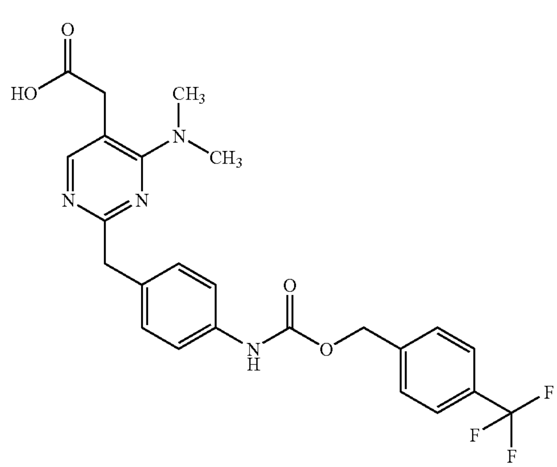 | 488.47 | 488 | 489 | 91-93 | A |

Example 10

{4,6-dichloro-2-[4-(2-naphthoylamino)benzyl]pyrimidin-5-yl}acetic acid

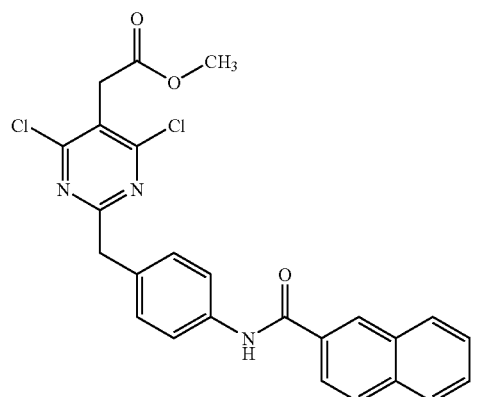

A THF (1.5 mL) solution of methyl {4,6-dichloro-2-[4-(2-naphthoylamino)benzyl]pyrimidin-5-yl}acetate (0.048 g, 0.10 mmol) at room temperature was treated with 1N NaOH (1 mL). After stirring for 16 hours at room temperature, the reaction mixture was poured into water and washed with EtOAc. The aqueous layer was acidified with 1N HCl and back extracted with EtOAc. The combined organic extracts was washed with brine, dried over anhydrous MgSO$_4$, filtered, and concentrated in vacuo. The remaining residue was chromatographed over silica gel eluting with 10% THF in CH$_2$Cl$_2$ containing 0.5% AcOH to give {4,6-dichloro-2-[4-(2-naphthoyl-amino)benzyl]pyrimidin-5-yl}acetic acid (0.007 g, 15% yield) as a white solid.

$^1$H NMR (300 MHz, DMSO-d$_6$) δ: 3.87 (s, 2H), 4.19 (s, 2H), 7.31 (d, J=9 Hz, 2H), 7.59-7.68 (m, 2H), 7.78 (d, J=9 Hz, 2H), 7.97-8.10 (m, 4H), 8.57 (s, 1H), 10.42 (s, 1H), 13.03 (bs, 1H).

Molecular weight: 466.33

Mass spectrometry: 466

Melting point: 230 Z° C.

Activity class: A

Example 11

N-(4-{[5-(2-Amino-2-oxoethyl)-4-chloro-6-(dimethylamino)pyrimidin-2-yl]methyl}phenyl)-2-naphthamide

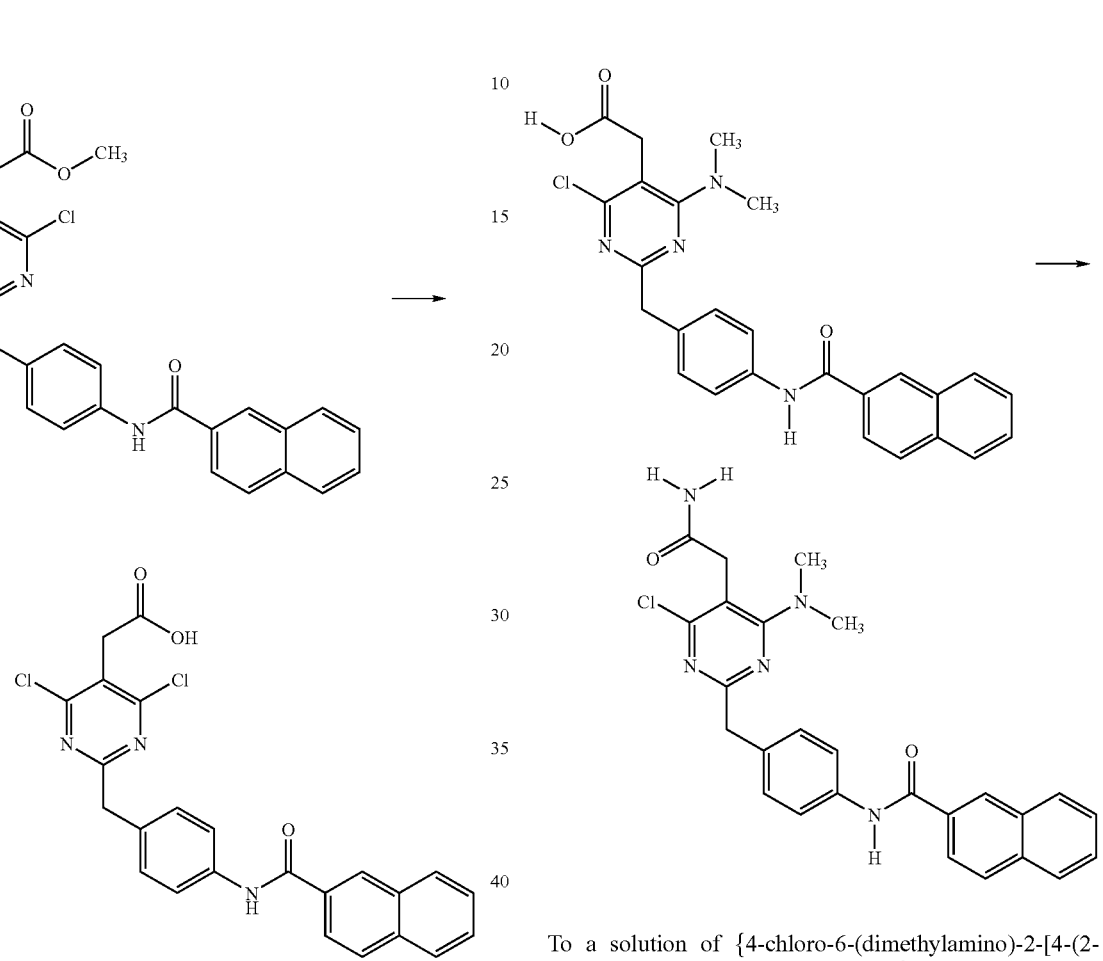

To a solution of {4-chloro-6-(dimethylamino)-2-[4-(2-naphthoylamino)benzyl]pyrimidin-5-yl}acetic acid (0.940 g, 1.98 mmol) in THF (18 mL) was added 1,1'-carbonyldiimidazole (0.353 mg, 2.18 mmol). The reaction mixture was stirred at room temperature for 2 hours followed by the addition of aqueous ammonia solution (28% NH$_3$, 0.94 mL). After stirring for 16 hours at room temperature, the reaction mixture was partitioned between EtOAc and water and the separated organic layer was washed with brine, dried over anhydrous Na$_2$SO$_4$, filtered, and concentrated in vacuo and the remaining residue was passed through a short pad of silica gel. Removal of acidic impurities via PS-carbonate resin then gave N-(4-{[5-(2-amino-2-oxoethyl)-4-chloro-6-(dimethylamino)pyrimidin-2-yl]methyl}phenyl)-2-naphthamide as a white solid (0.670 g, 71%).

$^1$H-NMR (500 MHz, DMSO-d6): δ 3.05 (s, 6H), 3.54 (s, 2H), 3.92 (s, 2H), 7.07 (s, 1H), 7.31 (d, J=8.5 Hz, 2H), 7.57 (s, 1H), 7.62-7.65 (m, 2H), 7.74 (d, J=8.5 Hz, 2H), 8.00-8.06 (m, 3H), 8.07-8.09 (m, 1H), 8.57 (s, 1H), 10.37 (s, 1H)

Molecular weight: 473.96

Mass spectrometry: 474

Melting point: 189-190° C.

Activity class: B

Example 12

N-(4-{[4-Chloro-5-(cyanomethyl)-6-(dimethylamino)pyrimidin-2-yl]methyl}phenyl)-2-naphthamide

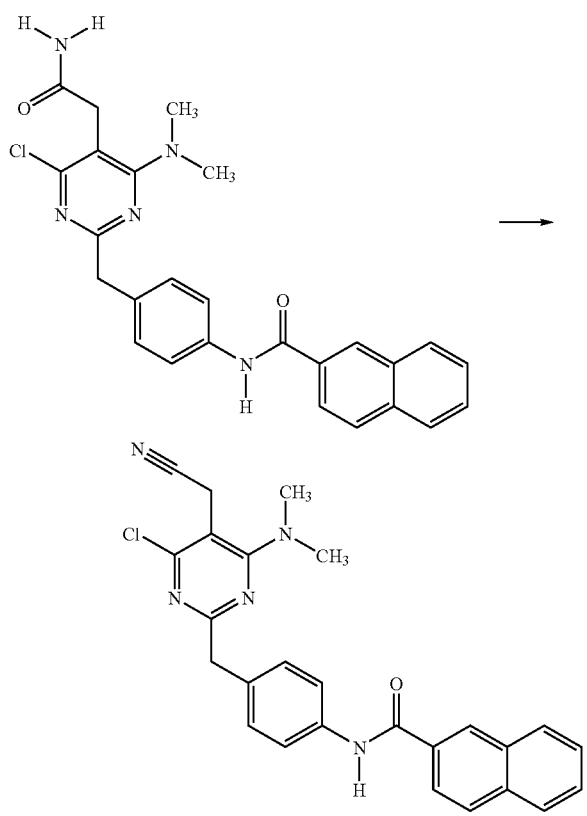

To a solution of N-(4-{([5-(2-amino-2-oxoethyl)-4-chloro-6-(dimethylamino)pyrimidin-2-yl]methyl}phenyl)-2-naphthamide (0.360 g, 0.76 mmol) in pyridine (15 mL) at rt was added trifluoroacetic anhydride (0.161 mL, 1.14 mmol) dropwise and the resulting reaction mixture was stirred at room temperature for 15 hours. The volatiles were removed in vacuo and the remaining residue was partitioned between EtOAc and saturated aqueous ammonium chloride solution. The separated organic layer was washed with brine, dried over anhydrous $Na_2SO_4$, filtered, and concentrated in vacuo. Purification of the resulting crude product by silica gel chromatography eluting with 20% EtOH in $CHCl_3$ gave N-(4-{([4-chloro-5-(cyanomethyl)-6-(dimethylamino)pyrimidin-2-yl]methyl}phenyl)-2-naphthamide as an amorphous solid (0.345 g, 100%).

$^1$H-NMR (500 MHz, DMSO-d6): δ 3.13 (s, 6H), 3.68 (s, 2H), 4.04 (s, 2H), 7.41 (d, J=8.5 Hz, 2H), 7.56-7.63 (m, 4H), 7.90-7.97 (m, 5H), 8.37 (s, 1H)

Molecular weight: 455.95
Mass spectrometry: 456
Melting point: amorphous solid
Activity class: C

Example 13

N-(4-{[4-Chloro-6-(dimethylamino)-5-(1H-tetrazol-5-ylmethyl)pyrimidin-2-yl]methyl}-phenyl)-2-naphthamide

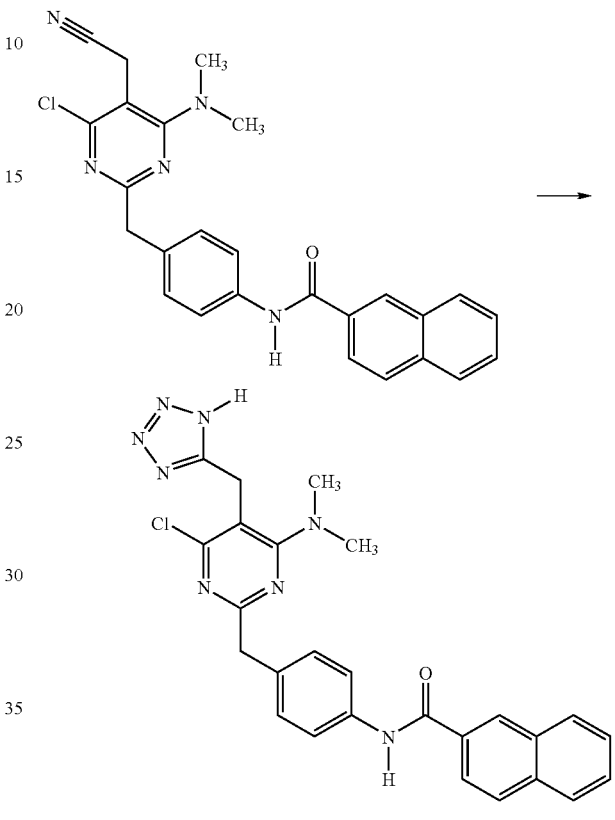

A solution containing N-(4-{[4-chloro-5-(cyanomethyl)-6-(dimethylamino)pyrimidin-2-yl]methyl}phenyl)-2-naphthamide (0.279 g, 0.61 mmol), sodium azide (0.159 g, 2.44 mmol), zinc dibromide (0.345 g, 1.55 mmol), 2-propanol (2.7 mL), water (4 mL), and 1,4-dioxane (5 mL) was heated at reflux for 24 hours. After cooling to room temperature, EtOAc (4 mL) was added and stirring was continued for 2 hours. The resulting mixture was poured into water and the precipitate thus formed was collected by suction, rinsed with water and MeOH, and dried in vacuo to give N-(4-{([4-chloro-6-(dimethylamino)-5-(1H-tetrazol-5-ylmethyl)pyrimidin-2-yl]methyl}-phenyl)-2-naphthamide as a light beige solid (0.095 g, 31%).

$^1$H-NMR (500 MHz, DMSO-d6): δ 2.95 (s, 6H), 3.93 (s, 2H), 4.14 (s, 2H), 7.32 (d, J=8.5 Hz, 2H), 7.16-7.64 (m, 3H), 7.74 (d, J=8.5 Hz, 2H), 8.00-8.03 (m, 3H), 8.07-8.09 (m, 2H), 8.56 (s, 1H)

Molecular weight: 498.97
Mass spectrometry: 499
Melting point: 280z° C.
Activity class: A

The invention claimed is:
1. A method of treating a disorder or disease selected from the group consisting of asthma, allergic rhinitis, atopic dermatitis and allergic conjunctivitis, the method comprising administering to a human or mammal in need of such treat- ment an effective amount of a compound of the formula (I), its tautomeric or stereoisomeric form, or a salt thereof:

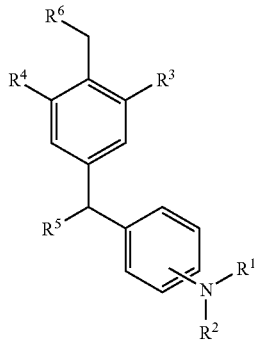
(I)

wherein:
R¹ represents hydrogen,

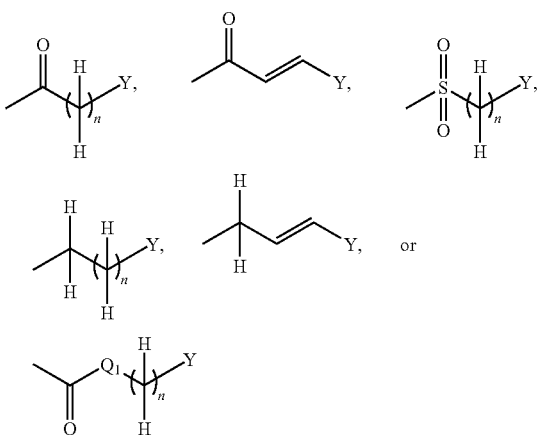

in which
n represents an integer of 0 to 6;
-Q₁- represents —NH—, —N(C₁₋₆ alkyl)-, or —O—;
Y represents hydrogen, C₁₋₆ alkyl, C₃₋₈ cycloalkyl optionally substituted by C₁₋₆ alkyl, C₃₋₈ cycloalkyl fused by benzene, aryl or heteroaryl, wherein said aryl and heteroaryl are optionally substituted at a substitutable position with one or more substituents selected from the group consisting of cyano, halogen, nitro, guanidino, pyrrolyl, sulfamoyl, C₁₋₆ alkylaminosulfonyl, di(C₁₋₆ alkyl)aminosulfonyl, phenyloxy, phenyl, amino, C₁₋₆ alkylamino, di(C₁₋₆ alkyl)amino, C₁₋₆ alkoxycarbonyl, C₁₋₆ alkanoyl, C₁₋₆ alkanoylamino, carbamoyl, C₁₋₆ alkylcarbamoyl, di-(C₁₋₆ alkyl)carbamoyl, C₁₋₆ alkylsulfonyl, C₁₋₆ alkyl optionally substituted by mono-, di-, or tri-halogen, C₁₋₆ alkoxy optionally substituted by mono-, di-, or tri-halogen and C₁₋₆ alkylthio optionally substituted by mono-, di-, or tri-halogen,
or aryl fused by 1,3-dioxolane;
R² represents hydrogen or C₁₋₆ alkyl;
R³ represents halogen, C₁₋₆ alkoxy optionally substituted by mono-, di-, or tri-halogen,

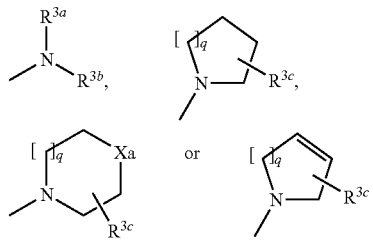

in which
R³ᵃ and R³ᵇ independently represent C₃₋₈ cycloalkyl, or C₁₋₆ alkyl, which C₁₋₆ alkyl is optionally substituted by hydroxy, carboxy, C₃₋₈ cycloalkyl, carbamoyl, C₁₋₆ alkylcarbamoyl, aryl-substituted C₁₋₆ alkylcarbamoyl, di(C₁₋₆ alkyl)carbamoyl, C₃₋₈ cycloalkylcarbamoyl, C₃₋₈ heterocyclylcarbonyl, C₁₋₆ alkylamino, di(C₁₋₆ alkyl)amino or C₁₋₆ alkoxy,
q represents an integer of 1 to 3,
R³ᶜ represents hydrogen, hydroxy, carboxy, or C₁₋₆ alkyl optionally substituted by hydroxy, carboxy or (phenyl-substituted C₁₋₆ alkyl)carbamoyl, and
Xa represents —O—, —S— or —N(R³ᵈ)—
in which
R³ᵈ represents C₁₋₆ alkyl;
R⁴ represents hydrogen, halogen, C₁₋₆ alkoxy, di(C₁₋₆ alkyl)amino or C₁₋₆ alkyl optionally substituted by C₁₋₆ alkoxy, or mono-, di-, or tri-halogen;
R⁵ represents hydrogen or C₁₋₆ alkyl; and
R⁶ represents carboxy, carboxamide, nitrile or tetrazolyl.

2. The method of claim 1, wherein the compound is of the formula (I), its tautomeric or stereoisomeric form, or a salt thereof, wherein:
R¹ represents

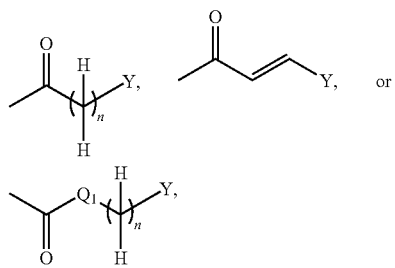

in which
n represents an integer of 0 to 2;
-Q₁- represents —NH—, —N(C₁₋₆ alkyl)-, or —O—;
Y represents C₁₋₆ alkyl, C₃₋₈ cycloalkyl optionally substituted by C₁₋₆ alkyl, C₃₋₈ cycloalkyl fused by benzene selected from the group consisting of indenyl and tetrahydronaphthyl, aryl selected from the group consisting of phenyl and naphthyl, or heteroaryl selected from the group consisting of indolyl, quinolyl, benzofuranyl, furanyl, chromanyl, and pyridyl, wherein said aryl and heteroaryl are optionally substituted at a substitutable position with one or more substituents selected from the group consisting of cyano, halogen, nitro, pyrrolyl, sulfamoyl, C₁₋₆ alkylaminosulfonyl, di(C₁₋₆ alkyl)aminosulfonyl, phenyloxy, phenyl, C₁₋₆ alkylamino, di(C₁₋₆ alkyl)amino, C₁₋₆ alkoxycarbonyl, C₁₋₆ alkanoylamino, carbamoyl, C₁₋₆ alkylcarbamoyl, di-(C₁₋₆ alkyl)carbamoyl, C₁₋₆ alkylsulfonyl, C₁₋₆ alkyl optionally substituted by mono-, di-, or tri-halogen, C₁₋₆ alkoxy optionally substituted by mono-, di-, or tri-halogen and $C_{1-6}$ alkylthio optionally substituted by mono-, di-, or tri-halogen; and $R^2$ represents hydrogen.

3. The method of claim 1, wherein the compound is of the formula (I), its tautomeric or stereoisomeric form, or a salt thereof, wherein $R^3$ represents $C_{1-6}$ alkoxy optionally substituted by mono-, di-, or tri-halogen,

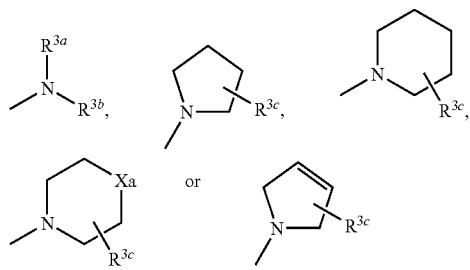

in which $R^{3a}$ and $R^{3b}$ independently represent $C_{1-6}$ alkyl optionally substituted by hydroxy, carboxy, $C_{3-8}$ cycloalkyl, carbamoyl, $C_{1-6}$ alkylcarbamoyl, di($C_{1-6}$alkyl)carbamoyl, $C_{3-8}$ cycloalkylcarbamoyl, $C_{3-8}$ heterocyclocarbonyl, $C_{1-6}$ alkylamino, di($C_{1-6}$ alkyl)amino or $C_{1-6}$ alkoxy;

$R^{3c}$ represents hydrogen, hydroxy, carboxy, or $C_{1-6}$ alkyl optionally substituted by hydroxy, carboxy or (phenyl-substituted $C_{1-6}$ alkyl)carbamoyl; and Xa represents —O—, —S— or —N($R^{3d}$)— in which $R^{3d}$ represents $C_{1-6}$ alkyl.

4. The method of claim 1, wherein the compound is of the formula (I-i), its tautomeric or stereoisomeric form, or a salt thereof:

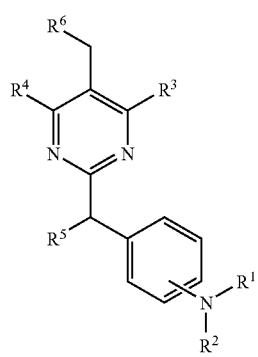

(I-i)

wherein:

$R^1$ represents

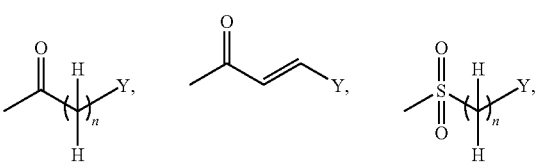

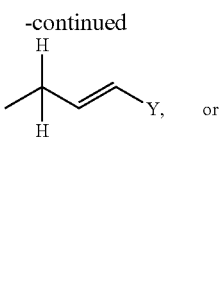

in which n represents an integer of 0 to 2;

$-Q_1-$ represents —NH—, —N($C_{1-6}$ alkyl)- or —O—;

Y represents phenyl, naphthyl, indolyl, quinolyl, benzofuranyl, furanyl or pyridyl, wherein said phenyl, naphthyl, indolyl, quinolyl, benzofuranyl, furanyl and pyridyl are optionally substituted at a substitutable position with one or two substituents selected from the group consisting of cyano, halogen, nitro, phenyloxy, phenyl, $C_{1-6}$ alkyl optionally substituted by mono-, di-, or tri-halogen, $C_{1-6}$ alkoxy optionally substituted by mono-, di-, or tri-halogen and $C_{1-6}$ alkylthio optionally substituted by mono-, di-, or tri-halogen;

$R^2$ represents hydrogen or $C_{1-6}$ alkyl;

$R^3$ represents

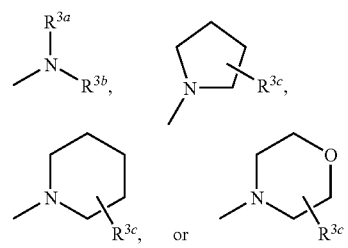

in which $R^{3a}$ and $R^{3b}$ independently represent $C_{3-8}$ cycloalkyl, or $C_{1-6}$ alkyl optionally substituted by $C_{3-8}$ cycloalkyl, carbamoyl, $C_{1-6}$ alkylcarbamoyl, phenyl-substituted $C_{1-6}$ alkylcarbamoyl, di($C_{1-6}$ alkyl)carbamoyl, $C_{3-8}$ cycloalkylcarbamoyl, $C_{3-8}$ heterocyclocarbonyl, $C_{1-6}$ alkylamino, di($C_{1-6}$ alkylamino or $C_{1-6}$ alkoxy; and $R^{3c}$ represents hydrogen, hydroxy, carboxy, or $C_{1-6}$ alkyl optionally substituted by hydroxy, carboxy or (phenyl-substituted $C_{1-6}$ alkyl)carbamoyl;

$R^4$ represents hydrogen, chloro, bromo, $C_{1-6}$ alkoxy, di($C_{1-6}$alkyl)amino or $C_{1-6}$ alkyl optionally substituted by $C_{1-6}$ alkoxy;

$R^5$ represents hydrogen, or methyl; and $R^6$ represents carboxy or tetrazolyl.

5. The method of claim 1, wherein the compound is selected from the group consisting of:

{4-chloro-6-(dimethylamino)-2-[4-(2-naphthoylamino)benzyl]-5-pyrimidinyl}acetic acid;

{4-chloro-6-{methyl[2-oxo-2-(1-pyrrolidinyl)ethyl]amino}-2-[4-(2-naphthoylamino)benzyl]-5-pyrimidinyl}acetic acid;

{4-chloro-6-[[2-(isopropylamino)-2-oxoethyl](methyl)amino]-2-[4-(2-naphthoylamino)benzyl]-5-pyrimidinyl}acetic acid;

{4-chloro-6-[[2-(cyclohexylamino)-2-oxoethyl](methyl)amino]-2-[4-(2-naphthoylamino)benzyl]-5-pyrimidinyl}acetic acid;
{2-[4-(benzoylamino)benzyl]-4-chloro-6-[[2-(cyclopentylamino)-2-oxoethyl](methyl)amino]-5-pyrimidinyl}acetic acid;
{4-chloro-2-{4-[(cyclohexylacetyl)amino]benzyl}-6-[[2-(cyclopentylamino)-2-oxoethyl](methyl)amino]-5-pyrimidinyl}acetic acid;
(4-chloro-6-[[2-(cyclopentylamino)-2-oxoethyl](methyl)amino]-2-{4-[(3-phenylpropanoyl)amino]benzyl}-5-pyrimidinyl)acetic acid;
[4-chloro-6-[[2-(cyclopentylamino)-2-oxoethyl](methyl)amino]-2-(4-{[(4-methylphenyl)acetyl]amino}benzyl)-5-pyrimidinyl]acetic acid;
(4-chloro-6-[[2-(cyclopentylamino)-2-oxoethyl](methyl)amino]-2-{4[(2-quinolinylcarbonyl)amino]benzyl}-5-pyrimidinyl)acetic acid;
[4-chloro-6-[[2-(cyclopentylamino)-2-oxoethyl](methyl)amino]-2-(4-{[(2E)-3-phenyl-2-propenoyl]amino}benzyl)-5-pyrimidinyl]acetic acid;
{4-chloro-2-{4-[(4-chlorobenzoyl)amino]benzyl}-6-6-[[2-(cyclopentylamino)-2-oxoethyl](methyl)amino]-5-pyrimidinyl}acetic acid;
{4-chloro-6-[[2-(cyclopentylamino)-2-oxoethyl](methyl)amino]-2-{4-[(3,4-dichlorobenzoyl)amino]benzyl}-5-pyrimidinyl}acetic acid;
{4-chloro-6-[[2-(cyclopentylamino)-2-oxoethyl](methyl)amino]-2-{4-[(4-methoxybenzoyl)amino]benzyl}-5-pyrimidinyl}acetic acid;
{4-chloro-6-[[2-(cyclopentylamino)-2-oxoethyl](methyl)amino]-2-{4-[(4-methylbenzoyl)amino]benzyl}-5-pyrimidinyl}acetic acid;
{4-chloro-6-[[2-(cyclopentylamino)-2-oxoethyl](methyl)amino]-2-[4-(1-naphthoylamino)benzyl]-5-pyrimidinyl}acetic acid;
{2-{4-[(benzofuran-2-ylcarbonyl)amino]benzyl}-4-chloro-6-[[2-(cyclopentylamino)-2-oxoethyl](methyl)amino]-5-pyrimidinyl}acetic acid;
{4-chloro-6-[[2-(cyclopentylamino)-2-oxoethyl](methyl)amino]-2-{4-[(1H-indol-2-ylcarbonyl)amino]benzyl}-5-pyrimidinyl}acetic acid;
{4-chloro-2-{4-[(4-cyanobenzoyl)amino]benzyl}-6-[[2-(cyclopentylamino)-2-oxoethyl](methyl)amino]-5-pyrimidinyl}acetic acid;
{4-chloro-6-[[2-(cyclopentylamino)-2-oxoethyl](methyl)amino]-2-{4-[(2,3-dihydro-1H-inden-2-ylacetyl)amino]benzyl}-5-pyrimidinyl}acetic acid;
[4-chloro-6-[[2-(cyclopentylamino)-2-oxoethyl](methyl)amino]-2-(4-{[(3-phenoxyphenyl)acetyl]amino}benzyl)-5-pyrimidinyl]acetic acid;
[4-chloro-6-[[2-(cyclopentylamino)-2-oxoethyl](methyl)amino]-2-(4-{[(4-phenoxyphenyl)acetyl]amino}benzyl)-5-pyrimidinyl]acetic acid;
(4-chloro-6-(dimethylamino)-2-{4-[(2-quinolinylcarbonyl)amino]benzyl}-5-pyrimidinyl)acetic acid;
[4-chloro-6-(dimethylamino)-2-(4-{[(2E)-3-phenyl-2-propenoyl]amino}benzyl)-5-pyrimidinyl]acetic acid;
[4-chloro-2-{4-[(3,4-dichlorobenzoyl)amino]benzyl}-6-(dimethylamino)-5-pyrimidinyl]acetic acid;
[4-chloro-2-{4-[(4-chlorobenzoyl)amino]benzyl}-6-(dimethylamino)-5-pyrimidinyl]acetic acid;
(4-chloro-6-(dimethylamino)-2-{4-[(4-methoxybenzoyl)amino]benzyl}-5-pyrimidinyl)acetic acid;
[4-chloro-6-(dimethylamino)-2-(4-{[4-(dimethylamino)benzoyl]amino}benzyl)-5-pyrimidinyl]acetic acid;
[4-chloro-2-{4-[(3,4-dimethoxybenzoyl)amino]benzyl}-6-(dimethylamino)-5-pyrimidinyl]acetic acid;
[4-chloro-6-(dimethylamino)-2-(4-{[4-(trifluoromethyl)benzoyl]amino}benzyl)-5-pyrimidinyl]acetic acid;
[4-chloro-2-(4-{[(2E)-3-(4-chlorophenyl)-2-propenoyl]amino}benzyl)-6-(dimethylamino)-5-pyrimidinyl]acetic acid;
[2-{4-[(4-bromobenzoyl)amino]benzyl}-4-chloro-6-(dimethylamino)-5-pyrimidinyl]acetic acid;
[4-chloro-2-{4-[(2,5-dichlorobenzoyl)amino]benzyl}-6-(dimethylamino)-5-pyrimidinyl]acetic acid;
[4-chloro-2-{4-[(3,4-difluorobenzoyl)amino]benzyl}-6-(dimethylamino)-5-pyrimidinyl]acetic acid;
[4-chloro-2-{4-[(3,5-dichlorobenzoyl)amino]benzyl}-6-(dimethylamino)-5-pyrimidinyl]acetic acid;
[4-chloro-2-{4-[(3-chlorobenzoyl)amino]benzyl}-6-(dimethylamino)-5-pyrimidinyl]acetic acid;
(4-chloro-6-(dimethylamino)-2-{4-[(3-methoxybenzoyl)amino]benzyl}-5-pyrimidinyl)acetic acid;
{4-chloro-6-(dimethylamino)-2-[3-(2-naphthoylamino)benzyl]-5-pyrimidinyl}acetic acid;
[2-(4-{[(4-tert-butylcyclohexyl)carbonyl]amino}benzyl)-4-chloro-6-(dimethylamino)-5-pyrimidinyl]acetic acid;
[4-chloro-2-{4-[(4-nitrobenzoyl)amino]benzyl}-6-(1-pyrrolidinyl)-5-pyrimidinyl]acetic acid;
[2-(4-{[4-(acetylamino)benzoyl]amino}benzyl)-4-chloro-6-(1-pyrrolidinyl)-5-pyrimidinyl]acetic acid;
[4-chloro-2-{4-[(4-phenoxybenzoyl)amino]benzyl}-6-(1-pyrrolidinyl)-5-pyrimidinyl]acetic acid;
[4-chloro-2-{4-[(4-isopropoxybenzoyl)amino]benzyl}-6-(1-pyrrolidinyl)-5-pyrimidinyl]acetic acid;
[4-chloro-6-(1-pyrrolidinyl)-2-(4-{[4-(1H-pyrrol-1-yl)benzoyl]amino}benzyl)-5-pyrimidinyl]acetic acid;
[4-chloro-2-{4-[(4-methoxy-3-nitrobenzoyl)amino]benzyl}-6-(1-pyrrolidinyl)-5-pyrimidinyl]acetic acid;
[4-chloro-2-{4-[(4-methoxy-3,5-dimethylbenzoyl)amino]benzyl}-6-(1-pyrrolidinyl)-5-pyrimidinyl]acetic acid;
[4-chloro-2-(4-{[(2E)-3-phenyl-2-propenoyl]amino}benzyl)-6-(1-pyrrolidinyl)-5-pyrimidinyl]acetic acid;
[4-chloro-2-{4-[(3,4-dichlorobenzoyl)amino]benzyl}-6-(1-pyrrolidinyl)-5-pyrimidinyl]acetic acid;
{4-chloro-6-[[2-(cyclopentylamino)-2-oxoethyl](methyl)amino]-2-[4-(2-naphthoylamino)benzyl]-5-pyrimidinyl}acetic acid;
(4-chloro-2-{4-[(4-chlorobenzoyl)amino]benzyl}-6-pyrrolidin-1-ylpyrimidin-5-yl)acetic acid;
[4-chloro-6-pyrrolidin-1-yl-2-(4-{[4-(trifluoromethyl)benzoyl]amino}benzyl)pyrimidin-5-yl]acetic acid;
[4-chloro-2-(4-{[(2E)-3-(4-chlorophenyl)prop-2-enoyl]amino}benzyl)-6-pyrrolidin-1-ylpyrimidin-5-yl]acetic acid;
{4-chloro-6-[(2-hydroxyethyl)(methyl)amino]-2-[4-(2-naphthoylamino)benzyl]pyrimidin-5-yl}acetic acid;
[4-chloro-2-(4-{[(2S)-3,4-dihydro-2H-chromen-2-ylcarbonyl]amino}benzyl)-6-(dimethylamino)pyrimidin-5-yl]acetic acid;
{4-chloro-6-(dimethylamino)-2-[4-({(2E)-3-[4-(trifluoromethyl)phenyl]prop-2-enoyl}amino)benzyl]pyrimidin-5-yl}acetic acid;
{4-(dimethylamino)-2-[4-(2-naphthoylamino)benzyl]-5-pyrimidinyl}acetic acid;
{4-[[2-(cyclopentylamino)-2-oxoethyl](methyl)amino]-2-[4-(2-naphthoylamino)benzyl]-5-pyrimidinyl}acetic acid;
{4-{methyl[2-oxo-2-(1-pyrrolidinyl)ethyl]amino}-2-[4-(2-naphthoylamino)benzyl]-5-pyrimidinyl}acetic acid;

{2-[4-(benzoylamino)benzyl]-4-[[2-(cyclopentylamino)-2-oxoethyl](methyl)amino]-5-pyrimidinyl}acetic acid;
[4-[[2-(cyclopentylamino)-2-oxoethyl](methyl)amino]-2-(4-{[(2E)-3-phenyl-2-propenoyl]amino}benzyl)-5-pyrimidinyl]acetic acid;
[2-{4-[(4-chlorobenzoyl)amino]benzyl}-4-(dimethylamino)-5-pyrimidinyl]acetic acid;
(4-(dimethylamino)-2-{4-[(4-methoxybenzoyl)amino]benzyl}-5-pyrimidinyl)acetic acid;
[2-{4-[(3,4-dichlorobenzoyl)amino]benzyl}-4-(dimethylamino)-5-pyrimidinyl]acetic acid;
(4-(dimethylamino)-2-{4-[(2-quinolinylcarbonyl)amino]benzyl}-5-pyrimidinyl)acetic acid;
[4-(dimethylamino)-2-(4-{[(2E)-3-phenyl-2-propenoyl]amino}benzyl)-5-pyrimidinyl]acetic acid;
[2-(4-{[(2E)-3-(4-chlorophenyl)-2-propenoyl]amino}benzyl)-4-(dimethylamino)-5-pyrimidinyl]acetic acid;
[4-(dimethylamino)-2-(4-{[4-(trifluoromethyl)benzoyl]amino}benzyl)-5-pyrimidinyl]acetic acid;
(4-(dimethylamino)-2-{4-[(3-methoxybenzoyl)amino]benzyl}-5-pyrimidinyl)acetic acid;
[2-{4-[(3-chlorobenozyl)amino]benzyl}-4-(dimethylamino)-5-pyrimidinyl]acetic acid;
[2-{4-[(4-bromobenzoyl)amino]benzyl}-4-(dimethylamino)-5-pyrimidinyl]acetic acid;
{4-(dimethylamino)-2-[4-({(2E)-3-[4-(trifluoromethyl)phenyl]prop-2-enoyl}amino)benzyl]pyrimidin-5-yl}acetic acid;
(4-(dimethylamino)-2-{1-[4-(2-naphthoylamino)phenyl]ethyl}pyrimidin-5-yl)acetic acid;
[4-(dimethylamino)-2-(4-1[4-(trifluoromethoxy)benzoyl]amino)benzyl)pyrimidin-5-yl]acetic acid;
(4-(dimethylamino)-2-{4-[(4-fluorobenzoyl)amino]benzyl}pyrimidin-5-yl)acetic acid;
[2-(1-{4-[(3,4-dichlorobenzoyl)amino]phenyl}ethyl)-4-(dimethylamino)pyrimidin-5-yl]acetic acid;
{4-(dimethylamino)-2-[1-(4-{[4-(trifluoromethyl)benzoyl]amino}phenyl)ethyl]pyrimidin-5-yl}acetic acid;
{4-(dimethylamino)-2-[1-(4-{[(2E)-3-phenylprop-2-enoyl]amino}phenyl)ethyl]pyrimidin-5-yl}acetic acid;
[4-(dimethylamino)-2-(1-{4-[(quinolin-2-ylcarbonyl)amino]phenyl}ethyl)pyrimidin-5-yl]acetic acid;
[2-(1-{4-[(4-chlorobenzoyl)amino]phenyl}ethyl)-4-(dimethylamino)pyrimidin-5-yl]acetic acid;
[4-(dimethylamino)-2-(1-{4-[(4-fluorobenzoyl)amino]phenyl}ethyl)pyrimidin-5-yl]acetic acid;
(4-pyrrolidin-1-yl-2-{4-[(quinolin-2-ylcarbonyl)amino]benzyl}pyrimidin-5-yl)acetic acid;
(2-{4-[(4-chlorobenzoyl)amino]benzyl}-4-pyrrolidin-1-ylpyrimidin-5-yl)acetic acid;
(2-{4-[(4-fluorobenzoyl)amino]benzyl}-4-pyrrolidin-1-ylpyrimidin-5-yl)acetic acid;
[4-pyrrolidin-1-yl-2-(4-{[4-(trifluoromethyl)benzoyl]amino}benzyl)pyrimidin-5-yl]acetic acid;
{2-[4-(2-naphthoylamino)benzyl]-4-pyrrolidin-1-ylpyrimidin-5-yl}acetic acid;
sodium (2-{4-[(3-methylbutanoyl)amino]benzyl}-4-pyrrolidin-1-ylpyrimidin-5-yl)acetate;
(2-{4-[(3,3-dimethylbutanoyl)amino]benzyl}-4-pyrrolidin-1-ylpyrimidin-5-yl)acetic acid;
[4-chloro-2-[4-(2-naphthoylamino)benzyl]-6-(1-pyrrolidinyl)-5-pyrimidinyl]acetic acid;
N-{5-(carboxymethyl)-6-chloro-2-[4-(2-naphthoylamino)benzyl]-4-pyrimidinyl}-N-methylglycine;
{4-chloro-6-[cyclohexyl(methyl)amino]-2-[4-(2-naphthoylamino)benzyl]-5-pyrimidinyl}acetic acid;
{4-chloro-6-[isopropyl(methyl)amino]-2-[4-(2-naphthoylamino)benzyl]-5-pyrimidinyl}acetic acid;
{4-chloro-6-[(2-methoxyethyl)(methyl)amino]-2-[4-(2-naphthoylamino)benzyl]-5-pyrimidinyl}acetic acid;
{4-chloro-6-(4-morpholinyl)-2-[4-(2-naphthoylamino)benzyl]-5-pyrimidinyl}acetic acid;
[4-chloro-2-[4-(2-naphthoylamino)benzyl]-6-(1-piperidinyl)-5-pyrimidinyl]acetic acid;
(4-chloro-6-(dimethylamino)-2-{4-[(1H-indol-6-ylcarbonyl)amino]benzyl}-5-pyrimidinyl)acetic acid;
{4-chloro-6-methoxy-2-[4-(2-naphthoylamino)benzyl]-5-pyrimidinyl}acetic acid;
{4-chloro-6-(2,5-dihydro-1H-pyrrol-1-yl)-2-[4-(2-naphthoylamino)benzyl]-5-pyrimidinyl}acetic acid;
{4-chloro-6-(diethylamino)-2-[4-(2-naphthoylamino)benzyl]-5-pyrimidinyl}acetic acid;
{4-chloro-6-[ethyl(methyl)amino]-2-[4-(2-naphthoylamino)benzyl]-5-pyrimidinyl}acetic acid;
{4-chloro-6-(3-hydroxy-1-pyrrolidinyl)-2-[4-(2-naphthoylamino)benzyl]-5-pyrimidinyl}acetic acid;
1-{5-(carboxymethyl)-6-chloro-2-[4-(2-naphthoylamino)benzyl]-4-pyrimidinyl}-L-proline;
[4-chloro-2-(4-{[(4-(methylthio)benzoyl]amino}benzyl)-6-(1-pyrrolidinyl)-5-pyrimidinyl]acetic acid;
[4-chloro-2-{4-[(3-chloro-4-methoxybenzoyl)amino]benzyl}-6-(1-pyrrolidinyl)-5-pyrimidinyl]acetic acid;
{2-{4-[(anilinocarbonyl)amino]benzyl}-4-chloro-6-[[2-(cyclopentylamino)-2-oxoethyl](methyl)amino]-5-pyrimidinyl}acetic acid;
{2-(4-{[(benzylamino)carbonyl]amino}benzyl)-4-chloro-6-[[2-(cyclopentylamino)-2-oxoethyl](methyl)amino]-5-pyrimidinyl}acetic acid;
{4-chloro-6-[[2-(cyclopentylamino)-2-oxoethyl](methyl)amino]-2-[4-({[(2-phenylethyl)amino]carbonyl}amino)benzyl]-5-pyrimidinyl}acetic acid;
[4-chloro-6-[[2-(cyclopentylamino)-2-oxoethyl](methyl)amino]-2-(4-{[(2-naphthylamino)carbonyl]amino}benzyl)-5-pyrimidinyl]acetic acid;
[2-(4-{[(benzylamino)carbonyl]amino}benzyl)-4-(dimethylamino)pyrimidin-5-yl]acetic acid;
[2-[4-({[benzyl(methyl)amino]carbonyl}amino)benzyl]-4-(dimethylamino)pyrimidin-5-yl]acetic acid;
{4-(dimethylamino)-6-(4-morpholinyl)-2-[4-(2-naphthoylamino)benzyl]-5-pyrimidinyl}acetic acid;
[4,6-bis(dimethylamino)-2-(4-{[4-(trifluoromethyl)benzoyl]amino}benzyl)pyrimidin-5-yl]acetic acid;
{4,6-bis(dimethylamino)-2-[4-(2-naphthoylamino)benzyl]-5-pyrimidinyl}acetic acid;
[4-(dimethylamino)-2-[4-(2-naphthoylamino)benzyl]-6-(1-pyrrolidinyl)-5-pyrimidinyl]acetic acid;
[4-(dimethylamino)-2-[4-(2-naphthoylamino)benzyl]-6-(1-piperidinyl)-5-pyrimidinyl]acetic acid;
[2-{4-[(3,4-dichlorobenzoyl)amino]benzyl}-4,6-bis(dimethylamino)pyrimidin-5-yl]acetic acid;
[4,6-bis(dimethylamino)-2-(4-{[(2E)-3-phenylprop-2-enoyl]amino}benzyl)pyrimidin-5-yl]acetic acid;
[2-(4-{[(2E)-3-(4-chlorophenyl)prop-2-enoyl]amino}benzyl)-4,6-bis(dimethylamino)pyrimidin-5-yl]acetic acid;
[2-(4-{[(2E)-3-(4-chlorophenyl)prop-2-enoyl]amino}benzyl)-4-(dimethylamino)-6-pyrrolidin-1-ylpyrimidin-5-yl]acetic acid;
[4-(dimethylamino)-2-(4-{[(2E)-3-phenylprop-2-enoyl]amino}benzyl)-6-pyrrolidin-1-ylpyrimidin-5-yl]acetic acid;
[4-(dimethylamino)-6-pyrrolidin-1-yl-2-(4-{[4-(trifluoromethyl)benzoyl]amino}benzyl)pyrimidin-5-yl]acetic acid;

[2-{4-[(biphenyl-3-ylcarbonyl)amino]benzyl}-4-(dimethylamino)-6-pyrrolidin-1-ylpyrimidin-5-yl]acetic acid;
[2-{4-[(biphenyl-4-ylcarbonyl)amino]benzyl}-4-(dimethylamino)-6-pyrrolidin-1ylpyrimidin-5-yl]acetic acid;
[2-{4-[(3,4-dichlorobenzoyl)amino]benzyl}-4-(dimethylamino)-6-morpholin-4-ylpyrimidin-5-yl]acetic acid;
[4-(dimethylamino)-6-morpholin-4-yl-2-(4-{[4-(trifluoromethyl)benzoyl]amino}benzyl)pyrimidin-5-yl]acetic acid;
[4-(dimethylamino)-6-morpholin-4-yl-2-(4-{[(2E)-2-phenylprop-2-enoyl]amino}benzyl)pyrimidin-5-yl]acetic acid;
(4-dimethylamino)-2-{4-[(3-phenoxybenzoyl)amino]benzyl}-6-pyrrolidin-1-ylpyrimidin-5-yl)acetic acid;
(4-(dimethylamino)-2-{4-[(4-phenoxybenzoyl)amino]benzyl}-6-pyrrolidin-1-ylpyrimidin-5-yl)acetic acid;
[4-(dimethylamino)-2-(4-{[(2E)-3-(4-methoxyphenyl)prop-2-enoyl]amino}benzyl)-6-morpholin-4-ylpyrimidin-5-yl]acetic acid;
[4-(dimethylamino)-2-(4-{[(2E)-3-(2-methoxyphenyl)prop-2-enoyl]amino}benzyl)-6-morpholin-4-ylpyrimidin-5-yl]acetic acid;
[2-{4-[(4-chlorobenzoyl)amino]benzyl}-4-(dimethylamino)-6-pyrrolidin-1-yl pyrimidin-5-yl]acetic acid;
[4-methyl-2-[4-(2-naphthoylamino)benzyl]-6-(1-pyrrolidinyl)-5-pyrimidinyl]acetic acid;
[2-{4-[(3,4-dichlorobenzoyl)amino]benzyl}-4-methyl-6-(1-pyrrolidinyl)-5-pyrimidinyl]acetic acid;
{4-(dimethylamino)-6-methyl-2-[4-(2-naphthoylamino)benzyl]pyrimidin-5-yl}acetic acid;
[2-{4-[(3,4-dichlorobenzoyl)amino]benzyl}-4-(dimethylamino)-6-methylpyrimidin-5-yl]acetic acid;
[4-(dimethylamino)-6-methyl-2-(4-{[(2E)-3-phenylprop-2-enoyl]amino}benzyl)pyrimidin-5-yl]acetic acid;
{4-(dimethylamino)-6-(methoxymethyl)-2-[4-(2-naphthoylamino)benzyl]pyrimidin-5-yl}acetic acid;
[4-(dimethylamino)-6-(methoxymethyl)-2-(4-{[4-(trifluoromethyl)benzoyl]amino}benzyl)pyrimidin-5-yl]acetic acid;
{4-(dimethylamino)-6-ethyl-2-[4-(2-naphthoylamino)benzyl]pyrimidin-5-yl}acetic acid;
[4-(dimethylamino)-6-ethyl-2-(4-{[4-(trifluoromethyl)benzoyl]amino}benzyl)pyrimidin-5-yl]acetic acid;
{4-(dimethylamino)-6-isopropyl-2-[4-(2-naphthoylamino)benzyl]pyrimidin-5-yl}acetic acid;
[4-(dimethylamino)-6-isopropyl-2-(4-{[4-(trifluoromethyl)benzoyl]amino}benzyl)pyrimidin-5-yl]acetic acid;
[2-(4-{[(benzyloxy)carbonyl]amino}benzyl)-4-(dimethylamino)pyrimidin-5-yl]acetic acid;
{4-(dimethylamino)-2-[4-({[(4-fluorobenzyl)oxy]carbonyl}amino)benzyl]pyrimidin-5-yl}acetic acid;
[2-(4-{[(benzyloxy)carbonyl]amino}benzyl)-4-chloro-6-(dimethylamino)pyrimidin-5-yl]acetic acid;
{4-(dimethylamino)-2-[4-({[(4-nitrobenzyl)oxy]carbonyl}amino)benzyl]pyrimidin-5-yl}acetic acid;
{4,6-dichloro-2-[4-(2-naphthoylamino)benzyl]pyrimidin-5-yl}acetic acid;
N-(4-{[5-(2-amino-2-oxoethyl)-4-chloro-6-(dimethylamino)pyrimidin-2-yl]methyl}phenyl)-2-naphthamide;
N-(4-{[4-chloro-6-(dimethylamino)-5-(1H-tetrazol-5-ylmethyl)pyrimidin-2-yl]methyl}phenyl)-2-naphthamide;
[2-(4-{[(benzyloxy)carbonyl]amino}benzyl)-4-(dimethylamino)pyrimidin-5-yl]acetic acid;
{4-(dimethylamino)-2-[4-({[(4-fluorobenzyl)oxy]carbonyl}amino)benzyl]pyrimidin-5-yl}acetic acid;
[2-(4-{[(benzyloxy)carbonyl]amino}benzyl)-4-chloro-6-(dimethylamino)pyrimidin-5-yl]acetic acid;
{4-(dimethylamino)-2-[4-({[(4-nitrobenzyl)oxy]carbonyl}amino)benzyl]pyrimidin-5-yl}acetic acid;
[2-(4-{[(benzyloxy)carbonyl]amino}benzyl)-4-(dimethylamino)-6-(methoxymethyl)-pyrimidin-5-yl]acetic acid;
[2-(4-{[(benzyloxy)carbonyl]amino}benzyl)-4-(dimethylamino)-6-ethyl-pyrimidin-5-yl]acetic acid;
[4,6-bis(dimethylamino)-2-(4-{[(benzyloxy)carbonyl]amino}benzyl)pyrimidin-5-yl]acetic acid;
(4-(dimethylamino)-2-{4-[({[4-(trifluoromethyl)benzyl]oxy}carbonyl)amino]benzyl}pyrimidin-5-yl)acetic acid;
{2-[4-([furan-2-ylcarbonyl]amino)benzyl]-4-chloro-6-[[2-(cyclopentylamino)-2-oxoethyl](methyl)amino]pyrimidin-5-yl}acetic acid;
{2-(4-hexanamidobenzyl)-4-chloro-6-[[2-(cyclopentylamino)-2-oxoethyl](methyl)amino]-pyrimidin-5-yl}acetic acid;
{2-(2-[3-{2-(biphenyl-4-yl)acetamido}benzyl])-4-chloro-6-[[2-(cyclopentylamino)-2-oxoethyl](methyl)amino]-pyrimidin-5-yl}acetic acid;
2-{2-(3-[2-(benzo[d][1,3]dioxol-5-yl)acetamido]benzyl)-4-chloro-6-([2-(cyclopentylamino)-2-oxoethyl](methyl)amino)pyrimidin-5-yl}acetic acid;
2-{4-chloro-2-[3-(4-sulfamoylbenzamido)benzyl]-6-(dimethylamino)-pyrimidin-5-yl}acetic acid;
2-{4-chloro-2-[3-(2,3-dichlorobenzamido)benzyl]-6-(dimethylamino)-pyrimidin-5-yl}acetic acid;
[4-(dimethylamino)-2-[3-(3,4-dimethoxybenzamido)benzyl]-pyrimidin-5-yl]acetic acid;
2-{2-[3-(2-cyclopropylacetamido)benzyl]-4-(pyrrolidin-1-yl)pyrimidin-5-yl}acetic acid;
2-[2-(3-butylamidobenzyl)-4-(pyrrolidin-1-yl)pyrimidin-5-yl]acetic acid;
2-{2-[3-({[benzyl(methyl)amino]carbonyl}amino)benzyl]-4-(dimethylamino)pyrimidin-5-yl}acetic acid;
{2-(4-hexanamidobenzyl)-4-chloro-6-[[2-(cyclopentylamino)-2-oxoethyl](methyl)amino]-pyrimidin-5-yl}acetic acid;
2-{4-chloro-[2-(4-[(2E)-3-phenyl-propenyl]amino)benzyl]-6-[[2-(cyclopentylamino)-2-oxoethyl](methyl)amino]pyrimidin-5-yl}acetic acid;
[4-chloro-2-{4-[(4-chlorobenzoyl)(methyl)amino]benzyl}-6-(dimethylamino)pyrimidin-5-yl]acetic acid;
2-{4-(dimethylamino)-6-(pyrrolidin-1-yl)-2-(4-{[(quinolin-2-yl)carbonyl]amino}benzyl)pyrimidin-5-yl}acetic acid;
2-{2-[4-(3,4-dichlorobenzamido)benzyl]-4-(dimethylamino)-6-(pyrrolidin-1-yl)pyrimidin-5-yl}acetic acid;
[2-{4-[(4-chlorobenzoyl)amino]benzyl}-4-(dimethylamino)-6-(morpholin-4-yl)pyrimidin-5-yl]acetic acid;
2-{2-[4-(4-fluorobenzamido)benzyl]-4-(dimethylamino)-6-(pyrrolidin-1-yl)pyrimidin-5-yl}acetic acid;
[2-{4-[(4-fluorobenzoyl)amino]benzyl}-4-(dimethylamino)-6-(morpholin-4-yl)pyrimidin-5-yl]acetic acid; and
N-(4-{[4-chloro-5-(cyanomethyl)-6-(dimethylamino)pyrimidin-2-yl]methyl}phenyl)-2-naphthamide.

6. A method of treating a disorder or disease selected from the group consisting of asthma, allergic rhinitis, atopic dermatitis and allergic conjunctivitis, the method comprising administering to a human or mammal in need of such treatment an effective amount of the compound of the formula

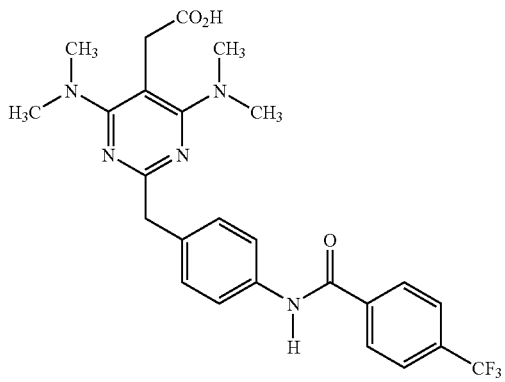

its tautomeric form, or a salt thereof.

7. A method of treating a disorder or disease selected from the group consisting of asthma, allergic rhinitis, atopic dermatitis and allergic conjunctivitis, the method comprising administering to a human or mammal in need of such treatment a pharmaceutical composition an effective amount of the compound of the formula

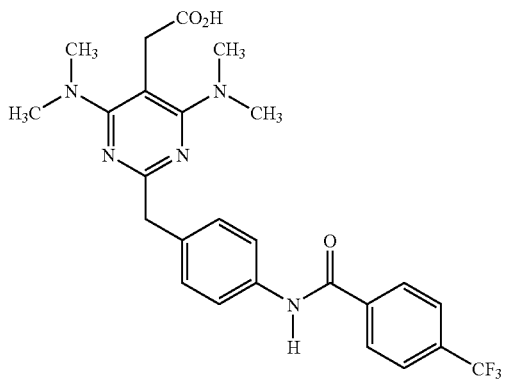

its tautomeric form, or a salt thereof, and one or more pharmaceutically acceptable excipients.

8. The method of claim 7, wherein the one or more excipients is a carrier, a diluent, a flavoring agent, a sweetener, a lubricant, a solubilizer, a suspension agent, a binder, a tablet disintegrating agent or an encapsulating material.

9. A method of treating a disorder or disease selected from the group consisting of asthma, allergic rhinitis, atopic dermatitis and allergic conjunctivitis, the method comprising administering to a human or mammal in need of such treatment a pharmaceutical composition comprising a pharmaceutically acceptable salt of the compound of the formula

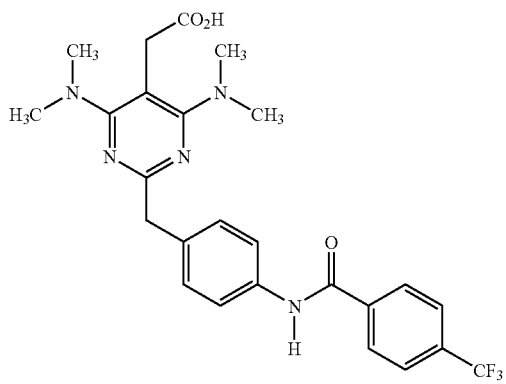

and one or more pharmaceutically acceptable excipients.

10. The method of claim 9, wherein the one or more excipients is a carrier, a diluent, a flavoring agent, a sweetener, a lubricant, a solubilizer, a suspension agent, a binder, a tablet disintegrating agent or an encapsulating material.

11. The method of claim 1, wherein the disease or disorder is asthma or allergic rhinitis.

12. The method of claim 6, wherein the disease or disorder is asthma or allergic rhinitis.

13. The method of claim 7, wherein the disease or disorder is asthma or allergic rhinitis.

14. The method of claim 9, wherein the disease or disorder is asthma or allergic rhinitis.

* * * * *

UNITED STATES PATENT AND TRADEMARK OFFICE
CERTIFICATE OF CORRECTION

PATENT NO.       : 7,960,393 B2
APPLICATION NO.  : 12/868663
DATED            : June 14, 2011
INVENTOR(S)      : Ly et al.

Page 1 of 1

It is certified that error appears in the above-identified patent and that said Letters Patent is hereby corrected as shown below:

In the Title page, item (63); under the title Related U.S. Application Data, "Apr. 14, 2002" should be replaced with --Apr. 14, 2004--.

Signed and Sealed this
Twenty-sixth Day of July, 2011

David J. Kappos
*Director of the United States Patent and Trademark Office*